United States Patent
Inoue et al.

(10) Patent No.: US 10,718,781 B2
(45) Date of Patent: Jul. 21, 2020

(54) METHOD FOR IDENTIFYING EPITOPE ON PROTEIN

(71) Applicant: Chugai Seiyaku Kabushiki Kaisha, Gotemba-shi, Shizuoka (JP)

(72) Inventors: Tomoaki Inoue, Gotemba (JP); Shunsuke Ito, Gotemba (JP); Nobuo Sekiguchi, Gotemba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 144 days.

(21) Appl. No.: 15/326,295

(22) PCT Filed: Jul. 13, 2015

(86) PCT No.: PCT/JP2015/070072
§ 371 (c)(1),
(2) Date: Jan. 13, 2017

(87) PCT Pub. No.: WO2016/010002
PCT Pub. Date: Jan. 21, 2016

(65) Prior Publication Data
US 2017/0219607 A1 Aug. 3, 2017

(30) Foreign Application Priority Data
Jul. 14, 2014 (JP) .................. 2014-144217

(51) Int. Cl.
G01N 33/53 (2006.01)
G01N 33/68 (2006.01)
(Continued)

(52) U.S. Cl.
CPC ......... *G01N 33/6872* (2013.01); *A61K 38/00* (2013.01); *C07K 7/00* (2013.01);
(Continued)

(58) Field of Classification Search
None
See application file for complete search history.

(56) References Cited

U.S. PATENT DOCUMENTS

| 2006/0251664 A1 | 11/2006 | Kropshofer et al. |
| 2009/0246869 A1 | 10/2009 | Tseng et al. |

(Continued)

FOREIGN PATENT DOCUMENTS

| EP | 1 826 217 A1 | 8/2007 |
| JP | 2006-300945 | 11/2006 |

(Continued)

OTHER PUBLICATIONS

Google translation of JP2006300945A (Year: 2018).*

(Continued)

*Primary Examiner* — M Franco G Salvoza
(74) *Attorney, Agent, or Firm* — Nixon & Vanderhye P.C.

(57) ABSTRACT

In one aspect, the present invention provides, for example, an improved method for identifying an epitope on a protein, comprising the following steps: (A) contacting a major histocompatibility complex (MHC molecule)-expressing cell differentiated from a stem cell or a progenitor cell derived therefrom with a target protein; (B) isolating a complex of a peptide contained in the target protein and the MHC molecule from the MHC molecule-expressing cell; and (C) eluting the peptide from the complex and identifying the peptide.

7 Claims, 35 Drawing Sheets

Specification includes a Sequence Listing.

(51) Int. Cl.
  A61K 38/00 (2006.01)
  C12P 21/02 (2006.01)
  C07K 7/00 (2006.01)
  C07K 14/00 (2006.01)
  C12Q 1/02 (2006.01)
  C12N 5/10 (2006.01)
  C07K 14/415 (2006.01)
  C07K 14/755 (2006.01)
  C07K 16/24 (2006.01)

(52) U.S. Cl.
  CPC ............ *C07K 14/00* (2013.01); *C07K 14/415* (2013.01); *C07K 14/755* (2013.01); *C07K 16/241* (2013.01); *C12N 5/10* (2013.01); *C12P 21/02* (2013.01); *C12Q 1/02* (2013.01); *C07K 2317/24* (2013.01)

(56) References Cited

U.S. PATENT DOCUMENTS

| | | |
|---|---|---|
| 2010/0322931 A1 | 12/2010 | Harding et al. |
| 2013/0195818 A1 | 8/2013 | Senju |
| 2013/0330822 A1 | 12/2013 | Nekahata et al. |

FOREIGN PATENT DOCUMENTS

| | | |
|---|---|---|
| JP | 2011-515100 | 5/2011 |
| JP | 2012-530496 | 12/2012 |
| JP | 2014-506447 | 3/2014 |
| WO | WO 2012/043651 A1 | 4/2012 |
| WO | WO 2012/115276 A1 | 8/2012 |

OTHER PUBLICATIONS

Berges et al., "A cell line model for the differentiation of human dendritic cells," Biochemical and Biophysical Research Communications 333: 896-907 (Year: 2005).*

International Search Report for International Application No. PCT/JP2015/070072, Japan Patent Office, Japan, dated Oct. 13, 2015, 10 pages.

Kropshofer, H. and Singer, T., "Overview of Cell-Based Tools for Pre-Clinical Assessment of Immunogenicity of Biotherapeutics," *Journal of Immunotoxicology* 3:131-136, Informa Healthcare, Switzerland (2006).

Senju, S., "Anti-Cancer Therapy with Pluipotent Stem Cell-Derived Dendritic Cells," *Biotherapy* 24(2):87-94, (2010).

Senju, S., "Saisei Iryo hyo no Genjo to Shinpo-ES Saibo, iPS Saibo to Taisei Kansaibo no Rinsho eno Oyo-6. Tanosei Saibo Yurai no Jujo Saibo o Mochiita Men'eki Ryoho," *Hematology Frontier* 19(11):1685-1692 (2009).

Senju, S., "Establishment of pluripotent stem cell-derived dendritic cells for clinical application," *The Japanese Journal of Clinical Hematology* 51(11):1668-1673 (2010).

Yanagimachi, M. D., et al., "Robust and Highly-Efficient Differentiation of Functional Monocytic Cells from Human Pluripotent Stem Cells under Serum- and Feeder Cell-Free Conditions," PLOS One 8(4):1-9 e59243 (2013).

Iwamoto, H., et al., "Antitumor immune response of dendritic cells (DCs) expressing tumor-associated antigens derived from induced pluripotent stem cells: In comparison to bone marrow-derived DCs," *International Journal of Cancer* 134:332-341, Wiley-Liss, United States (2014).

Karle, A. C., et al., "Nitration of the Pollen Allergen Bet v 1.0101 Enhances the Presentation of Bet v 1-Derived Peptides by HLA-DR on Human Dendritic Cells," *PLos One* 7:e31483, 9 pages, Public Library of Science, United States (2012).

Mutschlechner, S., et al, "Naturally processed T cell-activating peptides of the major birch pollen allergen," *J Allergy Clin Innnunol* 125:711-718, American Academy of Allergy, Asthma & Immunology, United States (2010).

Niwa, A., et al., "A Novel Serum-Free Monolayer Culture for Orderly Hematopoietic Differentiation of Human Pluripotent Cells via Mesodermal Progenitors," *PLos One* 6:e22261, 11 pages, Public Library of Science, Untied States (2011).

Rombach-Riegraf, V., et al., "Aggregation of Human Recombinant Monoclonal Antibodies Influences the Capacity of Dendritic Cells to Stimulate Adaptive T-Cell Responses In Vitro," *PLos One* 9:e86322, 17 pages, Public Library of Science, United States (2014).

Senju, S., et al., "Generation of dendritic cells and macrophages from human induced pluripotent stem cells aiming at cell therapy," *Gene Therapy* 18:874-883, Macmillan Publishers Limited, England (2011).

Van Haren, S.D., et al., "HLA-DR-presented Peptide Repertoires Derived From Human Monocyte-derived Dendritic Cells Pulsed With Blood Coagulation Factor VIII," *Molecular & Cellular Proteomics* 10:10.6, 12 pages, The American Society for Biochemistry and Molecular Biology Inc., United States (2011).

* cited by examiner

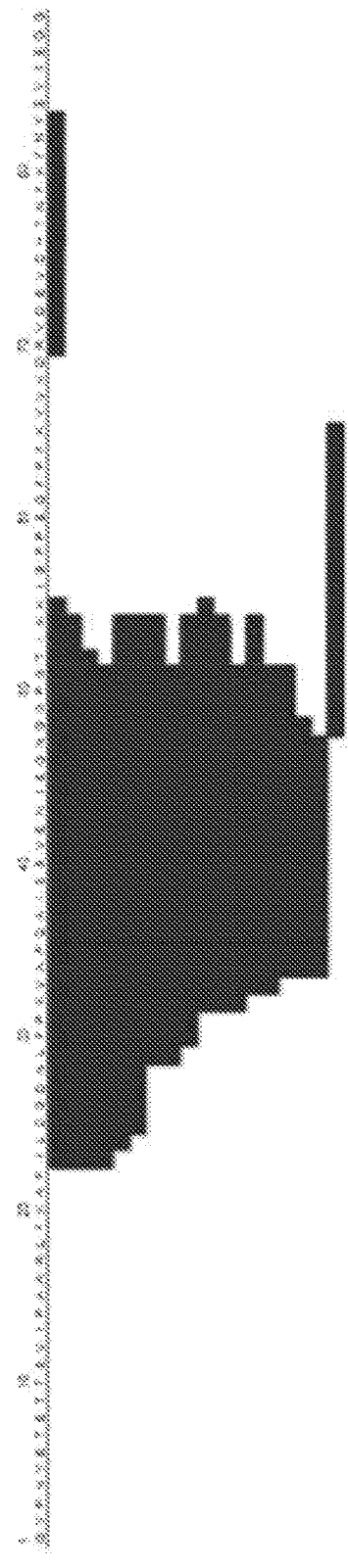
Figure 7A
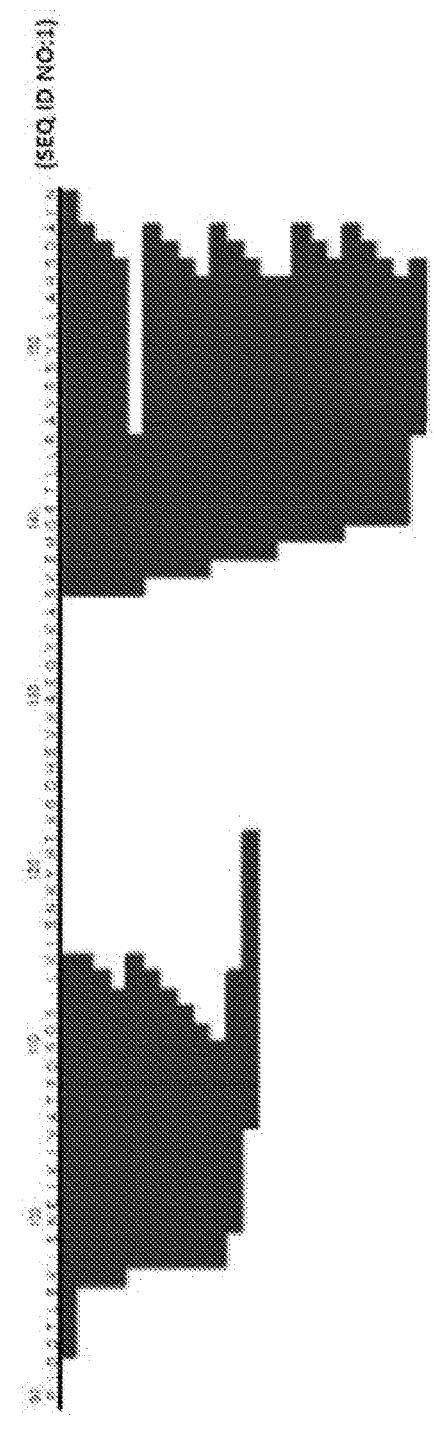
Figure 7B

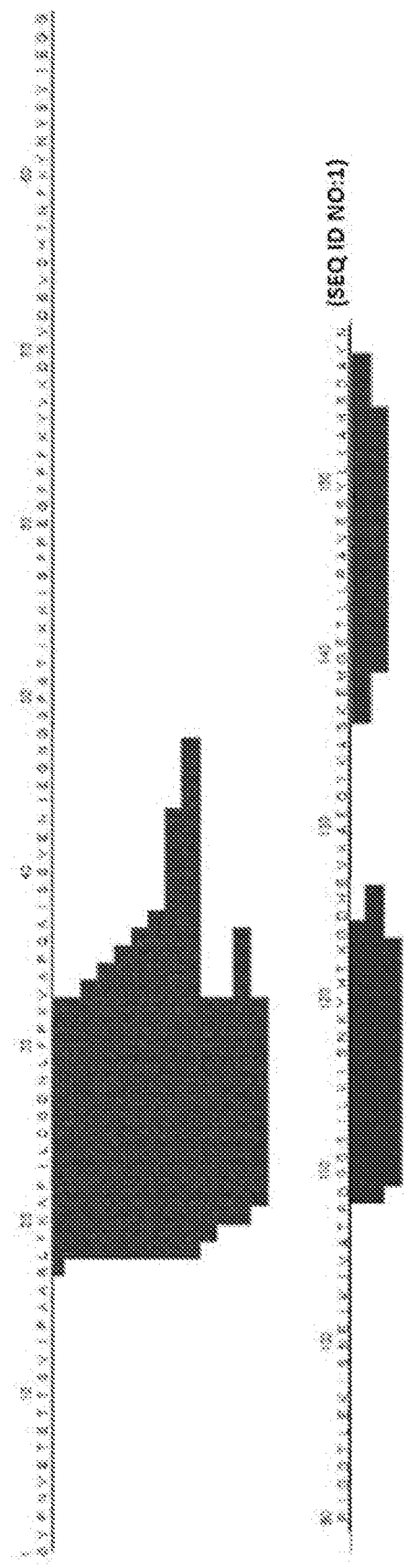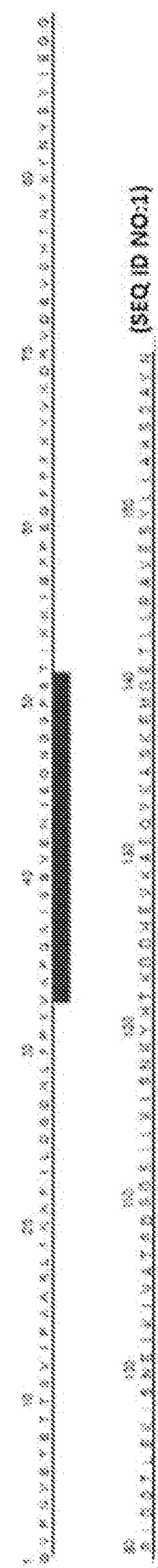
Figure 8A
Figure 8B

Figure 9A

Infliximab H chain

(SEQ ID NO:254)

Infliximab L chain

(SEQ ID NO:255)

Figure 9B

Infliximab H chain

(SEQ ID NO:254)

Infliximab L chain

No peptide (SEQ ID NO: 255)

Figure 10A

```
      10                    20                    30                    40                    50                    60                    70                    80                    90
ATRRYYLGAVELSHDYWQSDLGELPVQARFPPRRVPKSFPFNTSVYYKKTLFVEEFDHLFNIAKPRPPWMGLLGPTIQAEVYDTVVITLKKMASHPVSLH 100                   110                   120                   130                   140                   150                   160                   170                   180
AVGVSYWKASEGAEYQDQTSQREKEDDKVPPGGSHTYVMQVLKEMGPMASQPLCLTYSYLSHVDLVKDLMSGLIGALLVCREGSLAKEKTDLMKFLLLF 190                   200                   210                   220                   230                   240                   250                   260                   270
AVEDEGKEMMSETKMSLMQQRDAASARAMPKMMTYMQYVMRSLPGLLGCHRKSVYMKVLGMGTIPEVMRIFLEGMTFLVRMMQASLEISPITPLIAQTL
```

Figure 10C

```
       610                620                630                640                650                660                670                680                690
GVQLEDPEFGASNIMHSIINGYVFDSLQLEVCLHEVAVWYILSIGAQTDFLSVFFSGYTFKHKMVYEDTLLFPFSGETVPMSMENPGLMLLGCHNSQFRN 700                710                720                730                740                750                760                770                780
RGMTALLKVSSCCKNTGDYYEDSYEDISAYLLSKNNAIEPRSFSQNSRHPSTRQYQFNATTIPENDIEKTDPWFAHRTPMPKIQNVSSSDLLMLLRQSPT 790                800                810                820                830                840                850                860                870                880
PHGLSLSDLQRAKYETFSDDPSPGAIDSMNSLSEMTHFRPQLHMSODMYFTPEESGLQLRLNEKLGTTAATELKKLQFKVSSTSMNLISTIPSDNLAAGTQ
```

Figure 10E

```
      1200        1210        1220        1230        1240        1250        1260        1270        1280        1290
KKETLIQENVYLPQINTVTGIKNFMKNLFLLSTRQNVEGSYEGAYAPVLQDFRSLNDSTNRTIKKHTAHFSKKGEEENLEGLGNQIKQIVEKYACTTRLSP 1300        1310        1320        1330        1340        1350        1360        1370        1380        1390
NISQQNFVTQRSKRALKQFRLPLEETELEKRIIVDDTSTQWSKNMKHLTPSILTQIQYNEKEKQAITQSPLSDCLTRSHSIPQANRSPLPIAKVSSFPSI 1400        1410        1420        1430        1440        1450        1460        1470        1480        1490
RPIYLTRVLFQQNSSHLPAASYRKKDSGVQESSHFLQGAKKNNLSLAILTLEMTGQDRRBYGSLGTSATHGVIYKKVENTVLPKPDLPKTSGKVELLPKVH
```

U.S. Application No. 15/326,295
REPLACEMENT SHEET
5/12

Figure 11

```
         10        20        30        40        50        60        70        80
IPAVPEGPHIATYGDKWLDAKSIWTGKPIGAGPKDNGGAGGYKGVDKPPESQMTGGGNTPLFRSGRSCGRGELKGTKPEADEGEPYVYILRQMEEP
100       120       130       140       150       160       170       180
IAPYMEDLSGMAFGAMAMAKKCGEQKLRSEAGELELQFRRRVKGKYPEGTKVYIFMVEKGSMPMYLALLVKYVNGDGDYYAVOIRS
```
(SEQ ID NO:113)

Figure 14A  Donor 484_Bet v1a addition condition

```
  1 QVFNYETETTSVIPAARLFKAFILDGDNLFPKVAPQAISSVENIEGNGGPGTIKKISFPEGFPFKYVKDRVDEVDHTNFKYNYSVIEGG
 91 PIGDTLEKISNEIKIVATPDGGSILKISNKYHTKGDHEVKAEQVKASKEMGETLLRAVESYLLAHSDAYN  (SEQ ID NO:1)
```

Figure 14B  Donor 484_Bet v1a non-addition condition

```
  1 QVFNYETETTSVIPAARLFKAEILDGDNLFPKVAPQAISSVENIEGNGGPGTIKKISFPEGFPEKYVKDRVDEVDHTNFKYNYSVIEGG
No peptide
 91 PIGDTLEKISNEIKIVATPDGGSILKISNKYHTKGDHEVKAEQVKASKEMGETLLRAVESYLLAHSDAYN  (SEQ ID NO:1)
```

Figure 15A  Donor 554_Bet v1a addition condition

```
  1                          20                        40                        60                        80
  G V F N Y E T E T T S V I P A A R L F K A F I L D G D N L F P K V A P Q A I S S V E N I E G N G G P G T I L K I S F P E G F P F K Y V K D R V D E V D H T N F K Y N Y S V I E G G 90                        100                      120                      140
  P I G D T L E K I S N E I K I V A T P D G G S I L K I S N K Y H T K G D H E V K A E Q V K A S K E M G E T L L R A V E S Y L L A H S D A Y N   (SEQ ID NO:1)
```

Figure 15B  Donor 554_Bet v1a non-addition condition

```
  1                          20                        40                        60                        80
  G V F N Y E T E T T S V I P A A R L F K A F I L D G D N L F P K V A P Q A I S S V E N I E G N G G P G T I K K I S F P E G F P F K Y V K D R V D E V D H T N F K Y N Y S V I E G G 90                        100                      120                      140
  P I G D T L E K I S N E I K I V A T P D G G S I L K I S N K Y H T K G D H E V K A E Q V K A S K E M G E T L L R A V E S Y L L A H S D A Y N   (SEQ ID NO:1)
```

Figure 16A  Donor 558_Bet v1a addition condition

GVFNYETETTSVIPAARLFKAFILDGDNLFPKVAPQAISSVENIEGNGGPGTIKKISFPEGFPFKYVKDRVDEVDHTNFKYNYSVIEGG (SEQ ID NO:1)

PLGGTLLRKISNEIKLVATPDGGSILKISNKYHTKGDMEVKAEQVKASKEMGETLLRAVESYLLAHSDAYN (SEQ ID NO:1)

Figure 16B  Donor 558_Bet v1a non-addition condition

GVFNYETETTSVIPAARLFKAFILDGDNLFPKVAPQAISSVENIEGNGGPGTIKKISFPEGFPFKYVKDRVDEVDHTNFKYNYSVIEGG (SEQ ID NO:1)

PLGGTLLRKISNEIKLVATPDGGSILKISNKYHTKGDMEVKAEQVKASKEMGETLLRAVESYLLAHSDAYN (SEQ ID NO:1)

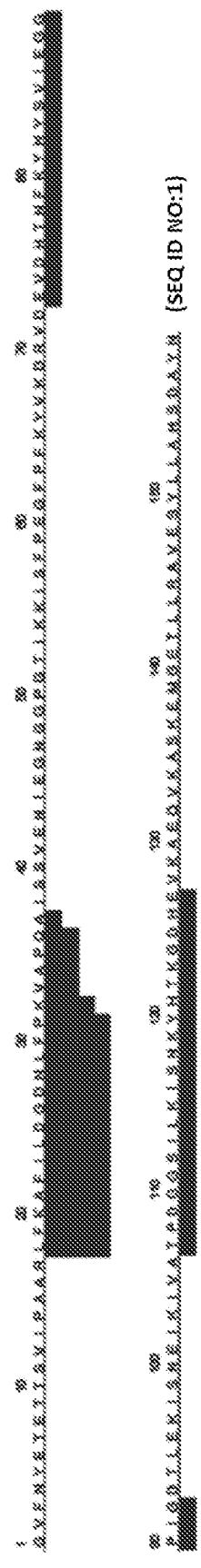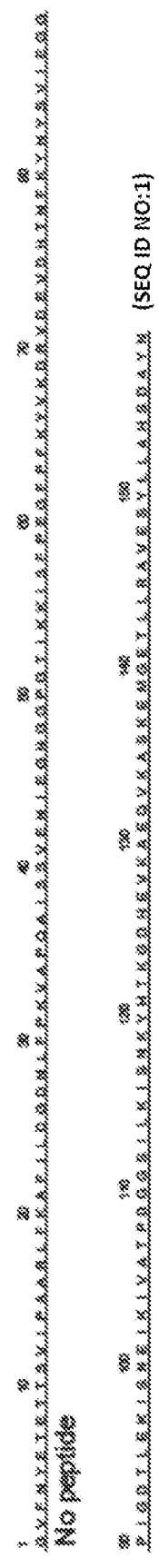
Figure 17A  Donor 560_Bet v1a addition condition
Figure 17B  Donor 560_Bet v1a non-addition condition

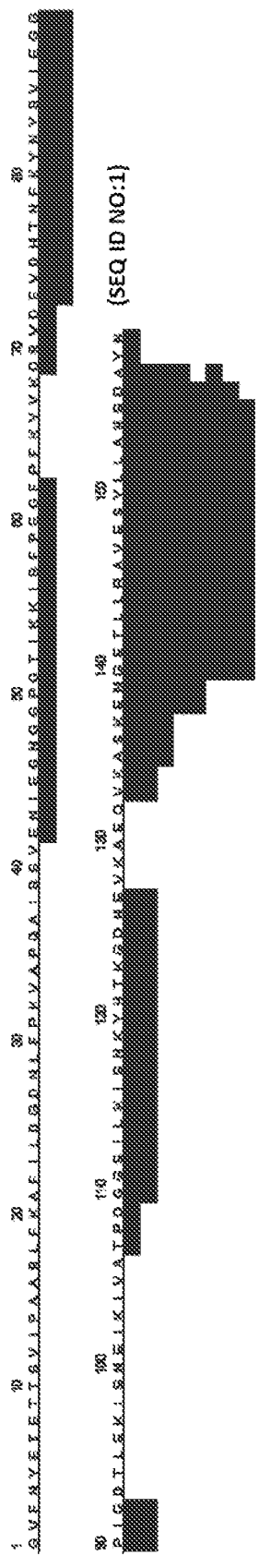

Figure 19A  Donor 565_Bet v1a addition condition

GVFNYETETTSVIPAARLFKAFILDGDNLFPKVAPQAISSVENIEGNGGPGTIKKISFPEGFPFKYVKDRVDEVDHTNFKYNYSVIEGG
PLGDTLEKISNEIKIVATPDGGSILKISNKYHTKGDMEVKAEQVKASKEMGETLLRAVESYLLAHSDAYN (SEQ ID NO:1)

Figure 19B  Donor 565_Bet v1a non-addition condition

GVFNYETETTSVIPAARLFKAFILDGDNLFPKVAPQAISSVENIEGNGGPGTIKKISFPEGFPFKYVKDRVDEVDHTNFKYNYSVIEGG
PLGDTLEKISNEIKIVATPDGGSILKISNKYHTKGDMEVKAEQVKASKEMGETLLRAVESYLLAHSDAYN (SEQ ID NO:1)

Figure 20A  Donor 566_Bet v1a addition condition

GVFNYETETTSVIPAARLFKAFILDGDNLFPKVAPQAISSVENIEGNGGPGTIKKISFPEGFPFKYVKDRVDEVDHTNFKKYNYSVIEGG
PLGDTLEKISNEIKIVATPDGGSILKISNKYHTKGDHEVKAEQVKASKEMGETLLRAVESYLLAHSDAYN  (SEQ ID NO:1)

Figure 20B  Donor 566_Bet v1a non-addition condition

GVFNYETETTSVIPAARLFKAFILDGDNLFPKVAPQAISSVENIEGNGGPGTIKKISFPEGFPFKYVKDRVDEVDHTNFKKYNYSVIEGG
No peptide
PLGDTLEKISNEIKIVATPDGGSILKISNKYHTKGDHEVKA

METHOD FOR IDENTIFYING EPITOPE ON PROTEIN

CROSS-REFERENCE TO RELATED APPLICATION

This application is a U.S. National Phase of PCT Application No. PCT/JP2015/070072, filed Jul. 13, 2015, which claims priority to Japanese Patent Application No. 2014-144217, filed Jul. 14, 2014, each of which is incorporated herein by reference.

REFERENCE TO SEQUENCE LISTING SUBMITTED ELECTRONICALLY

The content of the electronically submitted sequence listing (Name: Sequence_Listing.txt; Size: 85,742 bytes; and Date of Creation: Jan. 12, 2017) filed with the application is incorporated herein by reference in its entirety.

TECHNICAL FIELD

In one aspect, the present invention relates to, for example, a method for identifying a protein having immunogenicity, and also relates to, for example, a method for identifying an epitope that may play a causative role in the induction of immunogenicity.

BACKGROUND ART

In recent years, many bio-pharmaceuticals (antibody drugs, biologics, hormones, proteins, etc.) have contributed to medical innovation. However, immunogenicity possessed by these bio-pharmaceuticals is controversial, for example, from the viewpoint of efficacy and safety. In general, a property of an antigen that induces antibody production or cell-mediated immunity is called immunogenicity. The bio-pharmaceuticals can act as antigens to induce antibody production in the bodies of patients. In such a case, neutralizing antibodies against the bio-pharmaceuticals are produced, sometimes resulting in the reduced efficiency of treatment. Alternatively, allergic response, leaching reaction, infusion reaction, or the like may be caused. Alternatively, antibodies that cause autoimmune diseases or the like due to the neutralization of endogenous self-proteins may be produced in response to the bio-pharmaceuticals.

For the process of antibody production, it is important that an antigen is presented on a major histocompatibility complex (also referred to as a MHC molecule) present on the cell surface of an antigen-presenting cell (APC) (this is called "antigen presentation"). A MHC I molecule (class I) and a MHC II molecule (class II) are known as MHC molecules involved in the antigen presentation. For example, the MHC I molecule acts on killer T cells (CD8-positive T cells), and the MHC II molecule acts on helper T cells (CD4-positive T cells). The MHC I molecule acts on endogenous antigens in autologous cells, while the MHC II molecule acts on foreign antigens. Thus, antigen-antibody reaction or the like can be caused, for example, against cancer antigens produced in cancer cells, through antigen presentation mediated by the MHC I molecule. On the other hand, antigen-antibody reaction or the like can be caused against foreign antigens such as the bio-pharmaceuticals, or toxins through antigen presentation mediated by the MHC II molecule.

More specifically, in the case of the event mediated by the MHC I molecule, endogenous proteins in autologous cells are decomposed into smaller peptides by proteasome. Subsequently, each peptide binds to the MHC I molecule synthesized in the vesicle to form a complex. Then, the complex is delivered to the cell surface so that the peptide is presented as an epitope on the MHC I molecule.

On the other hand, in the case of the event mediated by the MHC II molecule, foreign proteins are first taken up into antigen-presenting cells by endocytosis. Subsequently, the taken-up proteins are decomposed into smaller peptides by lysosome. Then, each peptide binds to the MHC II molecule to form a complex. Then, the complex is delivered to the cell surface so that the peptide is presented as an epitope on the MCH II molecule. Subsequently, a T cell receptor on a helper T cell can bind to the antigen-presenting cell via the peptide.

However, these pathways are not definitive, and even foreign antigens may be processed by the MHC I molecule-mediated antigen presentation pathway (this is called "cross-priming").

In order to circumvent the immunogenicity of antibody drugs, etc., research has been conducted on the identification of peptide sequences presented on MHC molecules. This permits the prediction of the immunogenicity of proteins or peptides intended to be administered to organisms. Furthermore, epitopes can be modified by site-directed mutagenesis for the purpose of producing non-immunogenic proteins, for example, on the basis of information on epitope sequences. A method using a prediction algorithm in silico and T cell proliferation assay (e.g., the measurement of the ability of helper T cells to proliferate by the uptake of tritium-labeled thymidine) are known as methods for identifying peptide sequences. However, it has been difficult to predict an epitope sequence, for example, only from the binding affinity between an epitope candidate peptide and a MHC molecule. Accordingly, there has been a demand for more accurately predicting an epitope that may play a causative role in the induction of immunogenicity by directly identifying the sequence of a peptide presented on a MHC molecule.

Methods have been developed which involve contacting an antigen-presenting cell such as a dendritic cell (DC) with a protein to induce antigen presentation, allowing a MHC molecule on the cell to present a peptide derived from the protein, then separating and purifying a complex of the MHC molecule and the peptide, then eluting the peptide, and directly identifying the sequence of the peptide by use of liquid chromatography mass spectrometry (LC/MS) or the like (Patent Literature 1, Patent Literature 2, and Non Patent Literature 1). These methods are called MAPPs (MHC-associated peptide proteomics).

CITATION LIST

Patent Literature

Patent Literature 1: European Patent Application Publication No. 1715343
Patent Literature 2: European Patent Application Publication No. 1826217

Non Patent Literature

Non Patent Literature 1: Kropshofer, H, et al., J. Immunotoxicol., 3, 131, 2006

SUMMARY OF INVENTION

Technical Problem

In one aspect, in the method of Patent Literature 1, human peripheral blood mononuclear cells (PBMCs) separated by blood collection from a human are used as primary cells, and dendritic cells obtained by the induction of differentiation of monocytes further separated from these PBMCs are utilized as antigen-presenting cells. However, the monocytes are present only at approximately 10% of PBMCs and are also limited by the number of divisions. Therefore, there is a limitation on the number of cells that can be obtained. Furthermore, since MHC molecule allotypes may vary among different donors, it is impossible to constantly obtain a desired MHC molecule allotype. Thus, peptides to be identified by MAPPs may also vary. Since each component in blood also fluctuates depending on the states of patients, it is impossible to constantly isolate PBMCs under the same conditions. Accordingly, there has been demand for stably securing a plurality of antigen-presenting cells having diverse MHC molecule allotypes.

In an alternative aspect, serum is added for inducing the differentiation of monocytes into dendritic cells in many cases. Therefore, peptide sequences derived from proteins in the serum might also be detected.

In an alternative aspect, at present, there is also a limitation on the amount of PBMCs that can be obtained. Therefore, PBMCs derived from a plurality of donors are often pooled and used as bulks. Thus, it has not been easy to determine which peptide among identified peptides is involved in the induction of immunogenicity in a certain patient.

Solution to Problem

The present inventors have conducted diligent studies and consequently completed the present invention by, surprisingly, solving some or all of the problems described above, by the application of an antigen-presenting cell (specifically, a major histocompatibility complex (MHC molecule)-expressing cell) differentiated from a stem cell or a progenitor cell derived therefrom to MAPPs.

Specifically, the present invention provides the following exemplary aspects:

[1] A method for identifying an epitope on a protein, comprising the following steps:
(A) contacting a major histocompatibility complex (MHC molecule)-expressing cell differentiated from a stem cell or a progenitor cell derived therefrom with a target protein;
(B) isolating a complex of a peptide contained in the target protein and the MHC molecule from the MHC molecule-expressing cell; and
(C) eluting the peptide from the complex and identifying the peptide.

[2] The method according to [1], further comprising the following step:
(D) testing whether or not the identified peptide is an epitope that induces immunogenicity.

[3] The method according to [1] or [2], wherein the stem cell is selected from the group consisting of an induced pluripotent stem cell (iPS cell), an embryonic stem cell (ES cell), a nuclear transfer ES cell (ntES cell), an embryonic germ stem cell (EG cell), and an adult stem cell.

[4] The method according to any one of [1] to [3], wherein the MHC molecule is a MHC II molecule.

[5] The method according to [4], wherein the MHC II molecule is HLA-DR, HLA-DQ, or HLA-DP.

[6] The method according to any one of [1] to [5], wherein the MHC molecule-expressing cell further expresses at least one of CD80, CD86, CD206, and CD209.

[7] The method according to [6], wherein the MHC molecule-expressing cell expresses all of CD80, CD86, CD206, and CD209.

[8] The method according to any one of [1] to [7], wherein the MHC molecule-expressing cell is a dendritic cell.

[9] The method according to any one of [1] to [8], wherein the MHC molecule-expressing cell expresses one or more MHC molecule allotypes in a subject intended to receive the target protein.

[10] The method according to any one of [1] to [9], wherein the step (A) is performed under serum-free conditions.

[11] The method according to any one of [1] to [10], wherein
the dendritic cell is produced by a method comprising the following steps:
(a) differentiating the stem cell or the progenitor cell derived therefrom into a mesodermal progenitor cell;
(b) differentiating the mesodermal progenitor cell into a monocyte; and
(c) differentiating the monocyte into an immature dendritic cell, and optionally further stimulating the immature dendritic cell to obtain a mature dendritic cell, wherein
among the steps (a) to (c), at least the step (c) employs a serum-free medium.

[12] The method according to [11], wherein the step (b) comprises the step of differentiating the mesodermal progenitor cell into the monocyte in a serum-free medium containing a granulocyte macrophage colony-stimulating factor (GM-CSF) and a macrophage colony-stimulating factor (M-C SF).

[13] The method according to [11] or [12], wherein
the step (c) comprises the step of:
(c1) differentiating the monocyte into the immature dendritic cell in a serum-free medium containing a granulocyte macrophage colony-stimulating factor (GM-C SF) and interleukin 4 (IL-4), and optionally comprises the step of:
(c2) contacting the immature dendritic cell with an immunogen and optionally an inflammatory cytokine to induce the mature dendritic cell.

[14] The method according to any one of [8] to [13], wherein the dendritic cell is an immature dendritic cell, and the immature dendritic cell is contacted with a target protein having immunogenicity to induce the mature dendritic cell.

[15] The method according to any one of [1] to [14], wherein the target protein is at least one selected from the group consisting of cytokines, chemokines, growth factors, antibodies, enzymes, structural proteins, hormones, and fragments of any of these proteins.

[16] A method for producing a protein with reduced or eliminated immunogenicity, comprising the following steps:
(1) identifying an epitope on a protein according to a method according to any one of [1] to [15];
(2) modifying the epitope to reduce or eliminate the binding of the epitope to a MHC molecule; and
(3) producing a protein having the modified epitope.

[17] A protein obtainable according to a method according to [16].

[18] A method for predicting whether or not a protein has immunogenicity in a subject, comprising the steps of:
(I) providing a cell expressing one or more MHC molecule allotypes in the subject intended to receive the target protein, wherein the cell is differentiated from a stem cell or a progenitor cell derived therefrom;
(II) contacting the "cell expressing one or more MHC molecule allotypes" with the target protein;

(III) isolating a complex of a peptide contained in the target protein and the MHC molecule from the "cell expressing one or more MHC molecule allotypes";

(IV) eluting the peptide from the complex and identifying the peptide; and (V) optionally testing whether or not the identified peptide is an epitope that induces immunogenicity, wherein when the identified peptide is an epitope that induces immunogenicity, this indicates that the target protein has immunogenicity in the subject.

[19] The method according to [18], wherein one or more cells expressing one or more MHC molecule allotypes in the subject are provided such that all sets of MHC molecule allotypes carried by the subject are contained therein.

[20] The method according to [18] or [19], wherein the stem cell is an induced pluripotent stem cell (iPS cell) derived from the subject.

[21] A composition for the treatment and/or prevention of a disease related to a protein, in a subject, comprising the protein as an active ingredient, wherein the subject is selected from subjects predicted to be free from the immunogenicity of the protein according to a method according to any one of [18] to [20].

[22] Use of a stem cell or a progenitor cell derived therefrom, or a MHC molecule-expressing cell differentiated from the stem cell or the progenitor cell in a method according to any one of [1] to [16] and [18] to [20].

[23] A method for producing a dendritic cell from a stem cell or a progenitor cell derived therefrom, comprising the following steps:

(a') differentiating the stem cell or the progenitor cell derived therefrom into a mesodermal progenitor cell;

(b') differentiating the mesodermal progenitor cell into a monocyte in a serum-free medium containing a granulocyte macrophage colony-stimulating factor (GM-C SF) and a macrophage colony-stimulating factor (M-CSF); and (c') differentiating the monocyte into an immature dendritic cell in a serum-free medium, and optionally further stimulating the immature dendritic cell to obtain a mature dendritic cell.

[24] The method according to [23], wherein the step (c') comprises the step of:

(c1') differentiating the monocyte into the immature dendritic cell in a serum-free medium containing a granulocyte macrophage colony-stimulating factor (GM-C SF) and interleukin 4 (IL-4), and optionally comprise the step of:

(c2') contacting the immature dendritic cell with an immunogen and optionally an inflammatory cytokine to induce the mature dendritic cell.

[25] A dendritic cell obtainable by a method according to [23] or [24].

[26] The dendritic cell according to [25], wherein the dendritic cell further expresses at least one of CD80, CD86, CD206, and CD209 in addition to the MHC II molecule.

[27] The dendritic cell according to [26], wherein the dendritic cell expresses all of CD80, CD86, CD206, and CD209.

[28] A cell composition comprising a dendritic cell according to any one of [25] to [27].

[29] Those skilled in the art should understand that one of or any combination of two or more of the aspects described above is also included in the present invention unless a technical contradiction arises on the basis of the technical common sense of those skilled in the art.

Advantageous Effects of Invention

In one aspect, for example, antigen-presenting cells having diverse MHC molecule allotypes can be stably secured by providing a plurality of stem cells expressing different MHC molecule allotypes. Thus, combined analysis to predict whether or not desired proteins have immunogenicity in patients, which has not been easy to accomplish so far, can be conducted by providing one or more antigen-presenting cells expressing one or more, preferably all, of MHC molecule allotypes carried by patients.

In an alternative aspect, it is suggested that a system of the present invention using stem cells or progenitor cells derived therefrom as starting materials of antigen-presenting cells for MAPPs is more highly sensitive than a system using PBMCs as such starting materials.

In an alternative aspect, stem cells are not limited by the number of cell divisions, and methods for proliferation and maintenance thereof have already been established. Therefore, antigen-presenting cells expressing necessary MHC molecule allotypes can be produced and supplied stably in large amounts. Thus, the present invention is also excellent from the viewpoint of production cost and convenience.

In an alternative aspect, the possibility of detecting peptide sequences derived from proteins in serum can be circumvented by using a serum-free medium during the course of differentiation of stem cells into antigen-presenting cells.

BRIEF DESCRIPTION OF DRAWINGS

FIG. 7A and FIG. 7B. FIG. 7A shows results of analyzing the amino acid sequences of peptides detected by exposure to Bet v1a in MAPPs using dendritic cell-like cells derived from human iPS cells (Tic line) FIG. 7B shows results of analyzing the amino acid sequence of peptides detected both under Bet v1a non-treatment conditions and by exposure to Bet v1a. The amino acid sequence of Bet v1a is also shown. In the amino acid sequence of Bet v1a, peptides were detected at four roughly divided sites.

FIG. 8A and FIG. 8B. FIG. 8A shows results of analyzing the amino acid sequences of peptides detected by exposure to Bet v1a in MAPPs using dendritic cell-like cells derived from human iPS cells (201B7 line) FIG. 8B shows results of analyzing the amino acid sequence of peptides detected both under Bet v1a non-treatment conditions and by exposure to Bet v1a. The amino acid sequence of Bet v1a is also shown. In the amino acid sequence of Bet v1a, peptides were detected at three roughly divided sites.

FIG. 9A shows results of analyzing the amino acid sequences of peptides detected by exposure to infliximab in MAPPs using dendritic cell-like cells derived from human iPS cells (Tic line). The amino acid sequences of H and L chains of infliximab are also each shown.

FIG. 9B shows results of analyzing the amino acid sequences of peptides detected both under infliximab non-treatment conditions and by exposure to infliximab in MAPPs using dendritic cell-like cells derived from human iPS cells (Tic line). The amino acid sequences of H and L chains of infliximab are also each shown.

FIGS. 10A-10H. FIG. 10A and FIGS. 10B-10H show results of analyzing the amino acid sequences of peptides detected by exposure to recombinant human Factor VIII (SEQ ID NO: 112) in MAPPs using dendritic cell-like cells derived from human iPS cells (Tic line).

FIG. 10B shows a sequel of FIG. 10A.
FIG. 10C shows a sequel of FIG. 10B.
FIG. 10D shows a sequel of FIG. 10C.
FIG. 10E shows a sequel of FIG. 10D.
FIG. 10F shows a sequel of FIG. 10E
FIG. 10G shows a sequel of FIG. 10F.
FIG. 10H shows a sequel of FIG. 10G.

FIG. 11 shows results of analyzing the amino acid sequences of peptides detected by exposure to Phl p1 in MAPPs using dendritic cell-like cells derived from human iPS cells (Tic line).

FIG. 14A and FIG. 14B. FIG. 14A shows results of analyzing the amino acid sequences of peptides detected under Bet v1a addition conditions in MAPPs using dendritic cells derived from human donor PBMC. FIG. 14B shows results of analyzing the amino acid sequences of peptides detected under Bet v1a non-addition conditions (control) in MAPPs using dendritic cells derived from human donor PBMC.

FIG. 15A and FIG. 15B. FIG. 15A shows results of analyzing the amino acid sequences of peptides detected under Bet v1a addition conditions in MAPPs using dendritic cells derived from human donor PBMC. FIG. 15B shows results of analyzing the amino acid sequences of peptides detected under Bet v1a non-addition conditions (control) in MAPPs using dendritic cells derived from human donor PBMC.

FIG. 16A and FIG. 16B. FIG. 16A shows results of analyzing the amino acid sequences of peptides detected under Bet v1a addition conditions in MAPPs using dendritic cells derived from human donor PBMC. FIG. 16B shows results of analyzing the amino acid sequences of peptides detected under Bet v1a non-addition conditions (control) in MAPPs using dendritic cells derived from human donor PBMC.

FIG. 17A and FIG. 17B. FIG. 17A shows results of analyzing the amino acid sequences of peptides detected under Bet v1a addition conditions in MAPPs using dendritic cells derived from human donor PBMC. FIG. 17B shows results of analyzing the amino acid sequences of peptides detected under Bet v1a non-addition conditions (control) in MAPPs using dendritic cells derived from human donor PBMC.

FIG. 18A and FIG. 18B. FIG. 8A shows results of analyzing the amino acid sequences of peptides detected under Bet v1a addition conditions in MAPPs using dendritic cells derived from human donor PBMC. FIG. 18B shows results of analyzing the amino acid sequences of peptides detected under Bet v1a non-addition conditions (control) in MAPPs using dendritic cells derived from human donor PBMC.

FIG. 19A and FIG. 19B. FIG. 19A shows results of analyzing the amino acid sequences of peptides detected under Bet v1a addition conditions in MAPPs using dendritic cells derived from human donor PBMC. FIG. 19B shows results of analyzing the amino acid sequences of peptides detected under Bet v1a non-addition conditions (control) in MAPPs using dendritic cells derived from human donor PBMC.

FIG. 20A and FIG. 20B. FIG. 20A shows results of analyzing the amino acid sequences of peptides detected under Bet v1a addition conditions in MAPPs using dendritic cells derived from human donor PBMC. FIG. 20B shows results of analyzing the amino acid sequences of peptides detected under Bet v1a non-addition conditions (control) in MAPPs using dendritic cells derived from human donor PBMC.

FIG. 21A and FIG. 21B show results of comparing the amino acid sequences of peptides detected under Bet v1a (SEQ ID NO:1) addition conditions between use of dendritic cell-like cells derived from human iPS cells and use of dendritic cells derived from PBMCs.

FIG. 21B shows a sequel of FIG. 21A.

DESCRIPTION OF EMBODIMENTS

Figure 1:
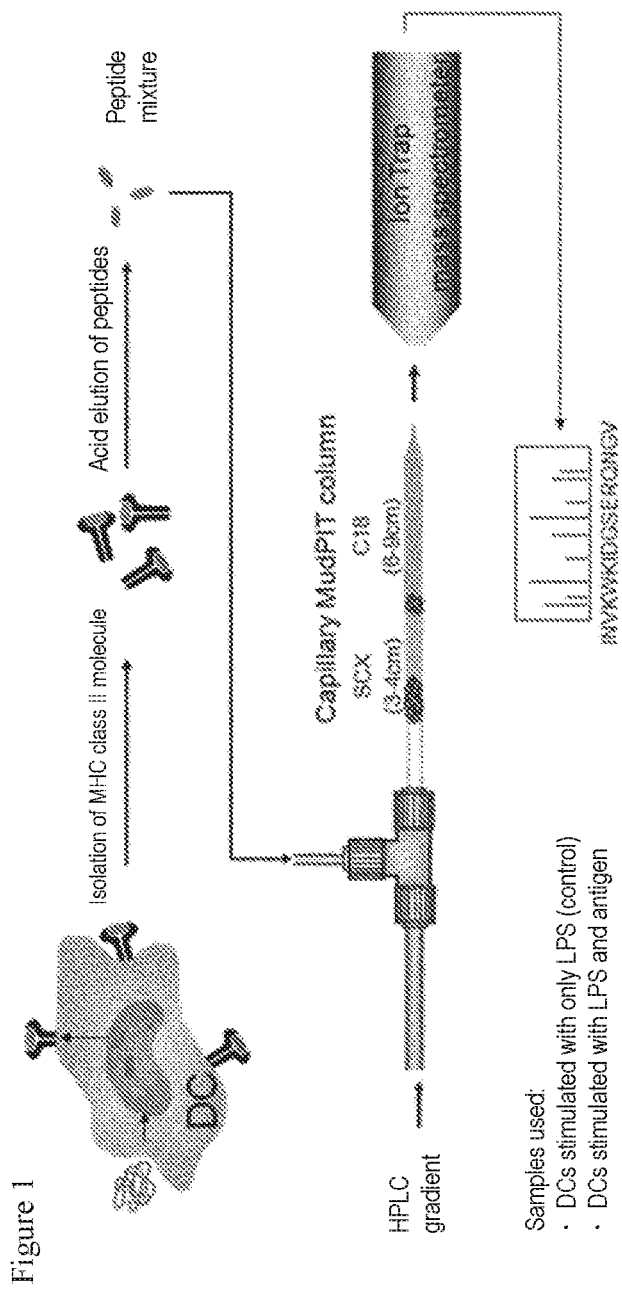
FIG. 1 shows one example of the outline of a technique using MHC II molecules among techniques of MAPPs (MHC-associated peptide proteomics). In the diagram, DC refers to a dendritic cell.

Hereinafter, preferred embodiments of the present invention will be described.

In the present specification, the protein may be, for example, a natural protein, a recombinant protein, or a synthetic peptide prepared by artificially bonding amino acids. It is understood that the protein may be one protein or a mixture of a plurality of different proteins. The protein may contain a non-natural amino acid. The protein may also be glycosylated, for example, when produced in vivo. The protein is preferably a protein (e.g., an antibody and a hormone) related to treatment or prevention for an animal (preferably a human). In one embodiment, the protein may be one or more, preferably one, selected from the group consisting of cytokines, chemokines, growth factors, antibodies, enzymes, structural proteins, hormones, and fragments of any of these proteins.

The protein is not particularly limited by the length of its amino acid sequence as long as the protein forms a complex with a MHC molecule for antigen presentation after being taken up into a cell and decomposed, after being taken up into a cell but not decomposed, or after being produced in a cell and decomposed. The protein may be a peptide itself that forms a complex with a MHC molecule for antigen presentation.

In the present specification, the epitope refers to a particular structural unit of an antigen to be recognized and bound by an antibody. The epitope is a minimum unit for antigenicity and is also called antigenic determinant.

In the present specification, the differentiation may refer to a state or an aspect, etc., in which an individual cell or a cell population, etc., which has been originally single or identical cell(s), is altered to acquire a complicated or distinct structure and/or function. The differentiation may be used interchangeably with the induction of differentiation, for example, and includes a state in which the induction of differentiation has been started, a state in which the induction of differentiation is ongoing, a state in which the induction of differentiation has been terminated, etc. It is understood that the differentiation should further encompass a state in which a cell or a cell population whose induction of differentiation has been terminated is proliferating, etc. In this context, the induction may mean that a certain cell or cell population, etc., is encouraged to differentiate structurally and/or functionally into another cell or cell population, etc. The induction is not particularly limited as long as the differentiation can be achieved.

In the present specification, the stem cell means a pluripotent stem cell and is not particularly limited as long as the stem cell is a cell having pluripotent differentiation and the ability to self-renew. Examples of the stem cell include induced pluripotent stem cells (iPS cells), embryonic stem cells (ES cells), nuclear transfer ES cells (ntES cells), embryonic germ stem cells (EG cells), and adult stem cells (WO2012/115276). These stem cells are preferably derived from a mammal and more preferably derived from a human.

The ES cell is an embryo-derived stem cell that is derived from, for example, the inner cell mass of a blastocyst, which is an embryo after an 8-cell stage of a fertilized egg and morula. The ES cell can be established by isolating the inner cell mass from the blastocyst of a fertilized egg of a subject animal and culturing the inner cell mass on a feeder of fibroblasts, and methods for establishment and maintenance thereof are known in the art (e.g., U.S. Pat. No. 5,843,780). The ES cell may be selected by real-time PCR by using, for example, the expression of a gene marker such as alkaline phosphatase, OCT-3/4, or NANOG gene as an index. Particularly, the human ES cell may be selected by using the expression of a gene marker such as OCT-3/4, NANOG, FBX15, FGF4, REX1, or ECAD gene as an index (E. Kroon et al., (2008), Nat. Biotechnol., 26: 443-452).

In one aspect, in view of ethical problems that may arise in association with the destroying of fertilized eggs or embryos, which may be potential human beings, for example, redundant embryos determined to be discarded among cryopreserved embryos that have not been brought back to mothers in fertility treatment based on external fertilization may be utilized as embryos for use in the preparation of human ES cells, or embryos that have stopped growing during development in the external fertilization process may be utilized as such embryos. Alternatively, unfertilized eggs may be utilized which lack the innate ability to grow into humans by themselves and are based on parthenogenesis in terms of cell division and growth. Alternatively, only single blastomeres of embryos at a cleavage stage prior to a blastocyst stage may be used to prepare ES cells without impairing the ability of the embryos to develop and without destroying fertilized eggs (Chung Y, Klimanskaya I, Becker S, Marh J, Lu S J, Johnson J, Meisner L, Lanza R. (2006). Nature 439: 216-219; Klimanskaya I, Chung Y, Becker S, Lu S J, Lanza R. (2006). Nature 444: 481-485; and Chung Y, Klimanskaya I, Becker S, Li T, Maserati M, Lu S J, Zdravkovic T, Ilic D, Genbacev O, Fisher S, Krtolica A, Lanza R. (2008). Cell Stem Cell 2: 113-117.). Alternatively, the ES cell may be prepared from a human embryo that has stopped developing (Zhang X, Stojkovic P, Przyborski S, Cooke M, Armstrong L, Lako M, Stojkovic M. (2006). Stem Cells 24: 2669-2676.).

The iPS cell is a somatic cell-derived artificial stem cell that has properties substantially equivalent to the ES cell, for example, pluripotent differentiation and the ability to self-renew, and can be prepared by introducing a particular reprogramming factor in a DNA or protein form into a somatic cell (K. Takahashi and S. Yamanaka (2006) Cell, 126: 663-676; K. Takahashi et al. (2007), Cell, 131: 861-872; J. Yu et al. (2007), Science, 318: 1917-1920; Nakagawa, M. et al., Nat. Biotechnol. 26: 101-106 (2008); and WO2007/069666). (In this context, the somatic cell may refer to every animal cell (preferably a mammalian cell including a human cell) except for germ-line cells and pluripotent stem cells.)

The reprogramming factor may be a gene specifically expressed in ES cells, a gene product or non-cording RNA thereof, a gene that plays an important role in maintaining the undifferentiation of ES cells, a gene product or non-cording RNA thereof, or a low-molecular compound. Examples of the reprogramming factors may include OCT3/4, SOX2, SOX1, SOX3, SOX15, SOX17, KLF4, KLF2, c-MYC, N-MYC, L-MYC, NANOG, LIN28, FBX15, ERAS, ECAT15-2, TCLL, beta-catenin, LIN28B, SALL1, SALL4, ESRRB, NR5A2, and TBX3. These reprogramming factors may be used alone or in combination. Examples of the combination of the reprogramming factors can include the following combinations:

(i) OCT gene, KLF gene, SOX gene, and MYC gene;
(ii) OCT gene, SOX gene, NANOG gene, and LIN28 gene;
(iii) OCT gene, KLF gene, SOX gene, MYC gene, hTERT gene, and SV40 large T gene; and
(iv) OCT gene, KLF gene, and SOX gene.

Alternatively, for example, combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, and WO2012/115276 may be used as combinations of the reprogramming factors. Examples of the reprogramming factor or a factor promoting reprogramming may include MEK inhibitors, DNA methyl transferase inhibitors, histone deacetylase (HDAC) inhibitors, histone methyl transferase inhibitors, and p53 inhibitors, which are inhibitors generally known to those skilled in the art. The reprogramming factor may be introduced into a somatic cell according to a method generally known to those skilled in the art, for example, a calcium phosphate method, lipofection, or microinjection, optionally using a vector (e.g., a viral vector, a plasmid vector, and an artificial chromosome vector) or the like. For example, a DMEM, DMEM/F12, or DME medium containing 10 to 15% FBS (which may further appropriately contain a leukemia inhibitory factor (LIF), penicillin/streptomycin, puromycin, L-glutamine, nonessential amino acids, β-mercaptoethanol, etc.), or a commercially available medium generally known to those skilled in the art may be appropriately used as a medium for the induction of the iPS cell.

The culture of the iPS cell may be appropriately set according to the composition of the medium, etc. For example, somatic cells are contacted with the reprogramming factor and cultured for approximately 4 to 7 days using a DMEM or DMEM/F12 medium containing 10% FBS at 37° C. in the presence of 5% $CO_2$. Then, the cells are reseeded onto feeder cells (e.g., mitomycin C-treated STO cells and SNL cells). Approximately 10 days after the contact of somatic cells with the reprogramming factor, the cells are cultured in a medium for primate ES cell culture containing a basic fibroblast growth factor (bFGF). Approximately 30 to approximately 45 days after the contact, or thereafter, an iPS-like colony may appear. Alternatively, the cells are cultured on feeder cells (e.g., mitomycin C-treated STO cells and SNL cells) in a DMEM medium containing 10% FBS (which may further appropriately contain LIF, penicillin/streptomycin, puromycin, L-glutamine, nonessential amino acids, β-mercaptoethanol, etc.) at 37° C. in the presence of 5% $CO_2$. Approximately 25 to approximately 30 days later, or thereafter, an iPS-like colony may appear. Instead of the feeder cells, somatic cells themselves to be reprogrammed may be used, or extracellular matrix or Matrigel (Becton, Dickinson and Company (BD)) may be used. Alternatively, the culture may be performed using a serum-free medium (Sun N, et al., (2009), Proc Natl Acad Sci USA. 106: 15720-15725).

The iPS cell may be selected according to the shape of the formed colony (e.g., whether to obtain a cell mass having a nearly spherical shape). Alternatively, in the case of introducing, as a marker gene, a drug resistance gene to be expressed in conjunction with a gene (e.g., alkaline phosphatase, OCT3/4, and NANOG genes) that is expressed by the reprogramming of somatic cells, the cells can be cultured in a medium containing the corresponding drug to select the established iPS cell. When the marker gene is a fluorescent protein gene, the iPS cell can also be selected by observation under a fluorescence microscope. Alternatively, the iPS cell may be determined by culturing the cells in vitro by a differentiation method known in the art and using their ability to differentiate into desired cells as an index. Alternatively, the iPS cell may be determined by subcutaneously transplanting the cells into an immunodeficient mouse and analyzing tumor tissues formed after a lapse of a predetermined period to confirm that teratomas made up of a mixture of various tissues are formed. Alternatively, the iPS cell may be determined by confirming that a marker gene specifically expressed in ES cells is expressed. Alternatively, the iPS cell may be determined by detecting a genome-wide gene expression pattern using a microarray or the like to confirm that the cells have an expression pattern highly correlating with that of ES cells.

Alternatively, established iPS cells may be furnished and used.

The ntES cell is a clone embryo-derived ES cell prepared by a nuclear transfer technique and has substantially the same properties as those of fertilized egg-derived ES cells (T. Wakayama et al. (2001), Science, 292: 740-743; S. Wakayama et al. (2005), Biol. Reprod., 72: 932-936; and J. Byrne et al. (2007), Nature, 450: 497-502). In short, the ntES cell is an ES cell established from the inner cell mass of a blastocyst derived from a clone embryo obtained by replacing the nucleus of an unfertilized egg with the nucleus of a somatic cell. For the preparation of the ntES cell, a nuclear transfer technique known in the art (e.g., J. B. Cibelli et al., (1998), Nature Biotechnol., 16: 642-646) may be combined with an ES cell preparation technique known in the art (Sayaka Wakayama, et al., (2008), Experimental Medicine, Vol. 26, No. 5 (extra number), p. 47 to 52). In the nuclear transfer, the nucleus of a somatic cell may be injected into an enucleated unfertilized mammalian egg and cultured for a few hours for reprogramming.

The EG cell is a cell that has pluripotency similar to that of ES cells and is established from a primordial germ cell during fetal life (Y. Matsui et al., (1992), Cell, 70: 841-847). The EG cell may be established by culturing primordial germ cells in the presence of LIF, bFGF, stem cell factor (STF), or the like (Y. Matsui et al., (1992), Cell, 70: 841-847).

The adult stem cell is a cell that has not been finally differentiated and is found in vivo. The adult stem cell exists as a source of a progenitor cell for a finally differentiated cell. The adult stem cell is present in each tissue in vivo and is usually limited by the types of cells into which the adult stem cell can differentiate. In the present invention, examples of the adult stem cell particularly preferably include hematopoietic stem cells considered to be able to differentiate into monocytes, macrophages, dendritic cells, and the like. In this context, hematopoietic progenitor cells refer to cells differentiated from the hematopoietic stem cells.

In the present specification, the progenitor cell derived from the stem cell may include every cell (e.g., mesodermal progenitor cells, hematopoietic progenitor cells, granulocyte macrophage colony-forming cells, lymphoblasts, monoblasts, promonocytes, and monocytes) that is observed in the course of differentiating the stem cell into an antigen-presenting cell (specifically, a MHC molecule-expressing cell). In this context, almost all of nucleated cells have MHC I molecules (Peter Parham (2007), THE IMMUNE SYSTEM; The Human Protein Atlas, http://www.proteinatlas.org/) and can antigen-present endogenous proteins in autologous cells, on killer T cells via the MHC I molecules. On the other hand, particular cells have MHC II molecules in addition to the MHC I molecules and can present foreign antigens on helper T cells via the MHC II molecules (these cells are also called professional antigen-presenting cells).

In the present specification, the antigen-presenting cell may include both of these types of cells. Examples of the antigen-presenting cell of the latter type preferably include dendritic cells, macrophages, monocytes, and B cells. Further, thyroid follicular cells, fibroblasts, vascular endothelial cells, and the like also work as antigen-presenting cells when MHC II molecules are induced through the activation by cytokines such as interferons. Therefore, these cells may be also included in the latter type. A criterion to determine whether to have properties as antigen-presenting cells (specifically, MHC molecule-expressing cells, for example, dendritic cells, macrophages, monocytes, and B cells) may be based on, for example, cells expressing MHC I and/or the MHC II molecules as an index and is more preferably based on cells further expressing at least one of CD11a, CD11b, CD11c, CD14, CD15, CD40, CD80, CD83, CD86, CD123, CD205, CD206, CD209, and CCR7 as an index.

Particularly, the dendritic cells have the strong ability to present antigens and the strong ability to activate helper T cells and are therefore advantageous as antigen-presenting cells. The antigen-presenting cell is most preferably an immature dendritic cell. The dendritic cells are cells that have cell processes and assume a dendritic form. A criterion to determine whether to have properties as dendritic cells may be based on, for example, the further expression of at least one of CD11b, CD11c, CD40, CD80, CD83, CD86, CD123, CD205, CD206, CD209, and CCR7 in addition to the MHC II molecule as an index and is more preferably based on the expression of all of the MHC II molecule, CD80, CD86, CD206, and CD209 as an index. A dendritic cell that expresses all of the MHC II molecule, CD80, CD86, CD206, and CD209 and is negative for CD14 is further preferred. A criterion to determine whether to have properties as macrophage cells may be based on, for example, the further expression of CD11b in addition to the MHC II molecule as an index. In this context, CD80 and CD86 are known to transduce signals to helper T cells and activate these cells. Dendritic cell-like cells obtained in the present Examples have properties similar to those of monocyte-derived dendritic cells in terms of cell shape, the expression of cell surface molecules, and the ability to stimulate helper T cells and may therefore be included in the dendritic cell described in the present specification. Likewise, monocyte-like cells obtained in the present Examples may be included in the monocyte described in the present specification.

The antigen-presenting cell is preferably derived from a mammal and is more preferably derived from a human.

In the present specification, the MHC molecule may be any of MHC I and MHC II molecules and is more preferably a MHC II molecule. Human MHC is called human leucocyte antigen (HLA). The MHC I molecules are further divided into classical class I (class Ia) and a non-classical class I (class Ib) molecules. Examples of the classical class I molecules include HLA-A, HLA-B, and HLA-C in humans. Examples of the non-classical class I molecules include HLA-E, HLA-F, and HLA-G in humans. On the other hand, examples of the MHC II molecules include HLA-DR, HLA-DQ, and HLA-DP in humans.

The MHC molecule differs slightly in amino acid sequence in individuals even among animals of the same species and is further divided into some subtypes called allotypes. For example, HLA-DR is known to have many allotypes such as DR1, DR2, DR3, DR4, . . . . Each allotype is linked on the MHC gene with the other allotypes. Therefore, these allotypes are inherited as a set from parent to child unless gene recombination occurs in this region. This unit is called haplotype. Stem cells (e.g., iPS cells) derived from a patient basically maintain the MHC gene sequence, as it is, of the patient even after being subcultured and/or differentiated. Therefore, antigen-presenting cells obtained by the differentiation of the stem cells maintain MHC molecule allotypes carried by the patient.

The allotypes respectively form complexes with different antigen peptide fragments (epitopes) so that the epitopes can be presented on the cell surface. Therefore, the presence or absence or the degree of immunogenicity, adverse reaction, etc., caused by a target protein varies depending on each allotype set, in other words, each patient having the allotype set. Allotypes or haplotypes have a pattern characteristic of a race or an ethnic group and can therefore be utilized, for example, in the analysis of the presence or absence of immunogenicity, adverse reaction, etc., caused by a target protein for each race or ethnic group.

Thus, a series of antigen-presenting cells having the MHC molecule allotypes of a fixed population (race, ethnic group, etc.) are advantageously used for predicting the immunogenicity of a protein for the population.

Allotypes carried by an individual person can be conveniently identified by genetic diagnosis (e.g., a HLA genotyping method which involves hybridizing DNA amplified by polymerase chain reaction (PCR) to probe-immobilized beads, digitizing the fluorescence intensity thereof, and analyzing the data to identify the HLA genotype) or the like. Therefore, whether the target protein causes immunogenicity, adverse reaction, etc., can be determined on the basis of information on the identified allotypes. Other specific examples of the genetic diagnosis method include methods described in, for example, International Journal of Immunogenetics, 2011; 38: 6, pp. 463-473.

Thus, in a preferred embodiment, the antigen-presenting cell may express one or more MHC molecule allotypes in a subject (e.g., a mammal, preferably a human) intended to receive the target protein.

In a preferred aspect, a cell expressing one or more MHC molecule allotypes carried by a subject (e.g., a human patient or a healthy person) intended to be analyzed may be used as the stem cell or the progenitor cell derived therefrom according to the present invention. For example, one or more cells expressing one or more MHC molecule allotypes in the subject may be used such that all sets of MHC molecule allotypes carried by the subject are contained therein. Alternatively, cells expressing one or more MHC molecule allotypes with high expression frequency in a race or an ethnic group intended to be analyzed may be prepared. For example, a fixed percentage (e.g., 30% to 80% or more) of a population of the race or the ethnic group may be covered by preparing a plurality of such cells and analyzed for the immunogenicity. For example, appropriate comparative analysis among human patients, between human patients and healthy persons, among healthy persons, etc., is advantageous.

In the present invention, the method for differentiating the stem cell or the progenitor cell derived therefrom into the antigen-presenting cell is not particularly limited as long as the method is generally known to those skilled in the art. Methods described in WO2009/120891; WO2009/074341; Regen. Med. (2009) 4 (4), p. 513-526; WO2012/115276; WO2012/043651; PLoS One, July 2011, Vol. 6, Issue 7, e22261; Gene Therapy (2011), 1-1024 March 2011, doi: 10.1038/gt.2011.22; Japan Science and Technology Agency, Strategic Basic Research Programs, CREST: H20-23 Research Report on Fundamental Technologies for Medicine Concerning the Generation and Regulation of Induced Pluripotent Stem (iPS) Cells; International Journal of Cancer 2013 Jul. 3. doi: 10.1002/ijc.28367; Zhuang, L. et al., J. Immunol. Methods (2012); PLoS One, April 2013, Vol. 8, Issue 4, e59243; and NATURE IMMUNOLOGY Vol. 5, No. 4, 2004, pp. 410-417 may be used as methods for differentiating stem cells such as ES cells or iPS cells into, for example, monocytes, macrophages, B cells, or dendritic cells. For example, Regen. Med. (2009) 4 (4), p. 513-526 discloses a method for inducing the in vitro differentiation of human ES cells into dendritic cells in a serum-free medium. In the method disclosed therein, human ES cells are differentiated into monocytes using bone morphogenetic protein-4 (BMP-4), a granulocyte macrophage-colony stimulating factor (GM-CSF), a stem cell factor (SCF), and a vascular endothelial growth factor (VEGF); subsequently, the monocytes are further differentiated into immature dendritic cells using GM-CSF and interleukin-4 (IL-4); and the immature dendritic cells are further differentiated into mature dendritic cells using a maturation cocktail consisting of GM-MSF, TNF-α, interleukin-1β (IL-1β), interferon-γ (IFN-γ), and PGE2. Also, PLoS One, April 2013, Vol. 8, Issue 4, e59243 discloses that functional macrophages and dendritic cells were obtained on the basis of monocytes differentiated from ES cells and iPS cells. Furthermore, NATURE IMMUNOLOGY Vol. 5, No. 4, 2004, pp. 410-417 describes a method for preparing T cells from ES cells as a theme and discloses that B cells were also able to be prepared in the course of this preparation (e.g., in this literature, the second paragraph of the right column on p. 411 to the second paragraph of the left column on p. 412; FIG. 1).

As mentioned above, related techniques have been reported as to the technique itself of differentiating stem cells into antigen-presenting cells (MHC molecule-expressing cells). However, all of these literatures intend the exploitation of the techniques in regenerative medicine or immunotherapy and do not intend the application thereof to the epitope sequence analysis of proteins.

For the specific method for differentiating the stem cell or the progenitor cell derived therefrom into the antigen-presenting cell according to the present invention, preferably, see WO2012/115276. When the antigen-presenting cell is, for example, a dendritic cell, this method may comprise the step of providing the stem cell or the progenitor cell derived therefrom and subsequently the following steps:
  (a) differentiating the stem cell or the progenitor cell derived therefrom into a mesodermal progenitor cell;
  (b) differentiating the mesodermal progenitor cell into a monocyte; and
  (c) differentiating the monocyte into an immature dendritic cell, and optionally further stimulating the immature dendritic cell to obtain a mature dendritic cell.

The step (a) and the step (b) can be continuously performed. Among the steps (a) to (c), at least the step (c) may employ a serum-free medium. Preferably, both the steps (b) and (c) employ a serum-free medium. More preferably, all of the steps (a) to (c) employ a serum-free medium.

The serum may refer to mammal-derived serum such as human serum, monkey serum, fetal bovine serum, sheep serum, rabbit serum, rat serum, guinea pig serum, or mouse serum.

The serum-free medium refers to a medium that is supplemented neither with serum nor with a commercially available serum replacement such as B-27 and may be preferably a medium containing at least one of albumin or an albumin replacement, transferrin or a transferrin replacement, insulin or an insulin replacement, and selenious acid. More preferably, the serum-free medium may be a medium containing insulin-transferrin-selenium-X supplement (ITS). Preferred examples of the serum-free medium include a minimum essential medium (MEM), a Dulbecco's modified eagle medium (DMEM), an Iscove's modified Dulbecco's medium (IMDM), StemPro-34 medium (Life Technologies/Thermo Fisher Scientific Inc.), Stemline II (Sigma-Aldrich Corp.), and Primate ES cell medium (ReproCELL Inc.) each supplemented with ITS.

The step (a) may comprise the step of culturing the stem cell or the progenitor cell derived therefrom in a medium containing BMP family protein and subsequently culturing the cell in a medium containing a growth factor and a hematopoietic factor, or culturing the cell in a medium containing VEGF and then culturing the cell in a medium containing a hematopoietic factor to obtain the mesodermal progenitor cell. The step (b) may comprise the step of differentiating the mesodermal progenitor cell into the monocyte by culture in a medium containing a hematopoietic factor. The step (a) and the step (b) can be continuously performed.

The BMP family protein may refer to a cytokine that belongs to the TGF-β superfamily and has approximately 20 subtypes. In the present invention, the BMP family protein is preferably BMP2 and/or BMP4, more preferably BMP4.

The growth factor may be preferably VEGF and may be specifically VEGF-A, VEGF-B, VEGF-C, VEGF-D, VEGF-E, PlGF (placental growth factor)-1, PlGF-2, or a selective splicing variant thereof (e.g., variants composed of 121, 165, 189, or 206 amino acids are known for VEGF-A). In the present invention, the VEGF is preferably VEGF-A. The growth factor may further include bFGF in addition to VEGF.

The hematopoietic factor is a factor promoting the differentiation and proliferation of blood cells and may be, for example, a stem cell factor (SCF), a granulocyte colony-stimulating factor (G-CSF), a granulocyte macrophage colony-stimulating factor (GM-CSF), a macrophage colony-stimulating factor (M-CSF), erythropoietin (EPO), thrombopoietin (TPO), an interleukin (IL), or Flt3 ligand. The interleukin may be IL-1, IL-2, IL-3, IL-4, IL-5, IL-6, IL-7, IL-8, or IL-9, etc.

The hematopoietic factor preferred for the step (b) may be selected from the group consisting of SCF, TPO, IL-3, Flt3 ligand, GM-CSF, and M-CSF. These hematopoietic factors may be used alone or in combination.

More preferably, the step (a) may be performed using VEGF as the growth factor and SCF as the hematopoietic factor in combination, and subsequently, the step (b) may be performed using GM-CSF and M-CSF as the hematopoietic factor in combination. In the step (b), it is preferred to replace the medium with a fresh one every few days (e.g., every 3 to 4 days) for culture.

Provided that a non-adherent cell (monocyte or monocyte-like cell) is obtained by the step (b), this non-adherent cell may be used as the monocyte in the step (c). Whether the non-adherent cell has the properties of the monocyte can be confirmed by using, for example, flow cytometry and using, as an index, the expression of a monocyte marker such as CD14, CD45$^{hi}$, CD11a, CD11b, or CD15 in addition to the expression of the MHC II molecule. From the viewpoint of improving the efficiency of induction of dendritic cells, the cell proportion of monocytes for use in the induction of dendritic cells can be increased, for example, by separating only CD14-positive cells from non-adherent cells by use of a magnetic bead method or the like.

The step (c) may further comprise the step of:
  (ci) differentiating the monocyte into an immature dendritic cell (or an immature dendritic cell-like cell) by (suspension-) culture in a medium containing a hematopoietic factor; and optionally comprise the step of:
  (cii) further contacting the obtained immature dendritic cell (or immature dendritic cell-like cell) with an immunogen and optionally an inflammatory cytokine to induce a mature dendritic cell (or a mature dendritic cell-like cell).

Whether the immature dendritic cell-like cell or the mature dendritic cell-like cell has the properties of the dendritic cell may be confirmed by using, for example, flow cytometry and using, as an index, the further expression of at least one of dendritic cell markers CD11b, CD11c, CD40, CD80, CD83, CD86, CD123, CD205, CD206, CD209, and CCR7 in addition to the expression of the MHC II molecule.

Whether the dendritic cell has the properties of the immature dendritic cell or has the properties of the mature dendritic cell can be tested by using, for example, change in the expression of the MHC II molecule (HLA-DR, etc.) as an index.

The hematopoietic factor may be any of the factors mentioned above. Preferably, a combination of GM-CSF, IL-3, and IL-4 or a combination of GM-CSF and IL-4 may be used as the hematopoietic factor.

Upon contact with the immature dendritic cell, the immunogen and the inflammatory cytokine can stimulate (pulse) the cell to induce a mature dendritic cell. The immature dendritic cell has high phagocytic capacity for an antigen but has the low ability to present the antigen, whereas this cell can be matured into a mature dendritic cell, for example, by the invasion of the antigen into an organism to enhance the expression of a protein, such as the MHC II molecule, necessary for antigen presentation and thereby improve the ability to present the antigen.

The immunogen may be any substance that causes immune response when introduced into an organism. Examples thereof include lipopolysaccharide (LPS, which is present in a pathogen). In the present invention, when the protein to be evaluated has immunogenicity, those skilled in the art can understand that this protein can act as the immunogen. Thus, in a preferred embodiment, the immature dendritic cell is contacted with a target protein having immunogenicity to induce the mature dendritic cell.

The inflammatory cytokine may be, for example, tumor necrosis factor-α (TNF-α), TNF-β, IL-12, or IFN-γ. These immunogens or inflammatory cytokines may be appropriately used alone or in combination.

If it is desired to obtain a macrophage instead of the dendritic cell as the antigen-presenting cell, the following step:

(d) differentiating the monocyte into a macrophage may be performed, instead of the step (c), according to a method described in PLoS One, April 2013, Vol. 8, Issue 4, e59243. In such a case, the monocyte can be differentiated into the macrophage using preferably GM-CSF or M-CSF as the hematopoietic factor. Further, the macrophage can be differentiated into M1 macrophage by adding, for example, IFN-γ or LPS or can be differentiated into M2 macrophage by adding, for example, IL-4 or IL-13 (macrophages are known to be activated by receiving cytokines produced by helper T cells, and classical activation (M1 macrophage) and selective activation (M2 macrophage) are known).

The respective concentrations of the growth factor, the hematopoietic factor, the cytokine, etc., used in each step mentioned above can be concentrations at which the antigen-presenting cell of interest is obtained, and can be appropriately determined by those skilled in the art. The concentration of BMP4 may be, for example, 5 to 150 ng/ml and is more preferably 10 to 100 ng/ml, further preferably 20 to 80 ng/ml. The concentration of VEGF may be, for example, 20 to 100 ng/ml and is more preferably 30 to 70 ng/ml, further preferably 40 to 50 ng/ml. The concentration of bFGF may be, for example, 10 to 100 ng/ml and is more preferably 20 to 50 ng/ml. The concentration of SCF may be, for example, 20 to 100 ng/ml and is more preferably 30 to 70 ng/ml, further preferably 40 to 50 ng/ml. The concentration of IL-3 may be, for example, 5 to 100 ng/ml and is more preferably 30 to 70 ng/ml. The concentration of TPO may be, for example, 1 to 25 ng/ml and is more preferably 1 to 10 ng/ml. The concentration of Flt3 ligand may be, for example, 10 to 100 ng/ml and is more preferably 30 to 70 ng/ml. The concentration of GM-C SF may be, for example, 5 to 250 ng/ml and is more preferably 50 to 200 ng/ml. The concentration of M-CSF may be, for example, 5 to 100 ng/ml and is more preferably 30 to 70 ng/ml. The concentration of IL-4 may be, for example, 3 to 100 ng/ml and is more preferably 10 to 70 ng/ml. The concentration of TNF-α may be, for example, 0.05 to 50 ng/ml and is more preferably 0.1 to 20 ng/ml. The concentration of LPS may be, for example, 0.01 to 100 µg/ml and is more preferably 0.1 to 10 µg/ml. These growth factors, hematopoietic factors, cytokines, etc., may be appropriately used in combination according to the purpose, and the optimum concentrations can be appropriately determined by those skilled in the art.

The concentration of the (target) protein to be evaluated can be, for example, a concentration at which an epitope on the protein can be identified, according to the purpose, or can be a concentration at which whether or not the protein has immunogenicity in a subject (e.g., a mammal, preferably a human) can be evaluated. Alternatively, the concentration thereof can be a concentration at which the mature dendritic cell can be induced by the stimulation of the immature dendritic cell. Such a concentration can be appropriately determined by those skilled in the art. Such a concentration may be, for example, 0.01 to 1000 µg/ml and is more preferably 0.1 to 100 µg/ml.

In order to obtain the antigen-presenting cell of interest, those skilled in the art can appropriately optimize the period of each step in consideration of the types and combination of factors to be added to cells. The period of the step (a) may be, for example, 2 days or longer and is preferably 2 to 10 days, more preferably 5 to 8 days. The period of the step (b) may be, for example, 1 day or longer and is preferably 20 to 200 days, more preferably 50 to 150 days. In the step (c), the period of the step (ci) may be, for example, 1 day or longer and is preferably 1 to 10 days, more preferably 4 to 6 days. The period of the step (cii) may be, for example, 12 hours or longer and is preferably 12 to 36 hours, more preferably 24 hours (1 day). The period of the step (d) may be, for example, 1 day or longer and is preferably 1 to 20 days. For example, at day 5 to 15, the macrophage may be further differentiated into M1 macrophage or M2 macrophage. However, those skilled in the art can appropriately determine the optimum culture period in consideration of each culture condition, as a matter of course.

The present invention may also relate to a method for producing a dendritic cell (in vitro) from a stem cell or a progenitor cell derived therefrom, comprising the steps (a) to (c), and a dendritic cell obtained or obtainable by the method. Specifically, the dendritic cell produced by the method expresses not only the MHC II molecule but CD80 and CD86, costimulatory molecules of helper T cells and expresses carbohydrate receptors CD206 and CD209, suggesting that this cell has the ability to activate helper T cells and resistance to viruses and the like. The sequence analysis of an epitope on a protein using the dendritic cell obtained by the method contributes to the development of a protein having low immunogenicity and, in addition, is also expected to bring about an excellent material for research on antigen-presenting cells against autoimmune diseases, viruses, and the like.

Specifically, the present invention further provides, as other aspects, for example, the following aspects:

[23] A method for producing a dendritic cell (in vitro) from a stem cell or a progenitor cell derived therefrom, comprising the following steps:

(a') differentiating the stem cell or the progenitor cell derived therefrom into a mesodermal progenitor cell;

(b') differentiating the mesodermal progenitor cell into a monocyte in a serum-free medium containing a granulocyte macrophage colony-stimulating factor (GM-C SF) and a macrophage colony-stimulating factor (M-CSF); and (c') differentiating the monocyte into an immature dendritic cell in a serum-free medium, and optionally further stimulating the immature dendritic cell to obtain a mature dendritic cell.

[24] The method according to [23], wherein
the step (c') comprises the step of:
(c1') differentiating the monocyte into the immature dendritic cell in a serum-free medium containing a granulocyte macrophage colony-stimulating factor (GM-C SF) and interleukin 4 (IL-4), and optionally comprises the step of:
(c2') contacting the immature dendritic cell with an immunogen and optionally an inflammatory cytokine to induce the mature dendritic cell.

[25] A dendritic cell obtainable by a method according to [23] or [24].

[26] The dendritic cell according to [25], wherein the dendritic cell further expresses at least one of CD80, CD86, CD206, and CD209 in addition to the MHC II molecule.

[27] The dendritic cell according to [26], wherein the dendritic cell expresses all of CD80, CD86, CD206, and CD209.

[28] A cell composition comprising a dendritic cell according to any of [25] to [27].

The dendritic cell or the cell composition may be used as a cell medicament for performing immune cell therapy for infectious diseases or malignant tumors, or for use in the control of immune response for the purpose of treating autoimmune diseases or rejection or the like associated with organ transplantation. The cell medicament may be appropriately used in combination with an auxiliary, for example, a medium, for the purpose of stably maintaining the dendritic cell.

In one aspect, the present invention also relates to a method for identifying an epitope on a protein, comprising the following steps:

(A) contacting a major histocompatibility complex (MHC molecule)-expressing cell differentiated from a stem cell or a progenitor cell derived therefrom with a target protein;

(B) isolating a complex of a peptide contained in the target protein and the MHC molecule from the MHC molecule-expressing cell; and (C) eluting the peptide from the complex and identifying the peptide. The method may further comprise the following step:

(D) testing whether or not the identified peptide is an epitope that induces immunogenicity. All of the steps of the method can be carried out in vitro.

For avoiding detecting the amino acid sequences of peptides derived from proteins in serum, it is preferred that the step (A) should be performed under serum-free conditions.

The degree of immunogenicity (or antigenicity) can also be compared, for example, among different proteins, among different protein preparations, or among different bio-pharmaceuticals by use of the method for identifying an epitope on a protein. This method can also be utilized in the quality control of produced proteins.

In the present invention, the amount of the MHC molecule-expressing cell necessary for obtaining, for example, 100 ng of MHC molecules may depend on the number of cells, the expression intensity of the MHC molecules, and the degree of the expression. The optimum amount of the cell can be appropriately determined by those skilled in the art.

Each MHC II molecule allotype (e.g., HLA-DQ1) can carry approximately 500 to 1000 different peptide fragments (Chicz R M et al., J Exp. Med. 1993, 178, 27-47; and Chicz R M & Urban R G, Immunol. Today, 1993, 15, 155-160). However, a great majority of these different peptides merely attain a very low copy number and therefore are not very likely to play a physiological role in vivo. On the other hand, peptide fragments that participate in immunogenicity and activate, for example, helper T cells attain a moderate to high copy number (Latek R R & Unanue E R, Immunol. Rev. 1999, 172: 209-228). These peptides having a moderate to high copy number account for approximately 40 to 50% of the total amount of peptides eluted from MHC II molecules and can correspond to approximately 10 to 200 individual peptides.

Many peptide fragments that form complexes with MHC II molecules are presented as 2 to 5 C-terminally and N-terminally truncated variants sharing a common core sequence of approximately 10 to 13 amino acids indispensable for recognition by T cell receptor (Rudensky A Y et al., Nature 1992, 359, 429-431; and Chicz et al., Nature 1992, 358: 764-768). These variants constitute the same epitope. This means that the number of important different epitopes is actually smaller and falls within the range of, for example, approximately 5 to 70.

The peptide is a peptide that is derived from (the amino acid sequence of) the target protein and can form a complex with the MHC molecule on the surface of the antigen-presenting cell (specifically, the MHC molecule-expressing cell). The peptide may be bound with an intracellular or extracellular MHC molecule. Each MHC II molecule allotype can form a complex with diverse peptides, and the amount of the peptide necessary for the sequencing of each eluted peptide can be, for example, only a fmol amount. According to the method of the present invention, approximately a fmol amount of peptide fragments bound with MHC molecules can be isolated from, for example, approximately 0.1 to 5 μg of MHC molecules, and the sequences of the peptides can be identified.

In order to isolate the complexes of the MHC molecules and the peptides from the antigen-presenting cell, the cell membrane of the cell may be lysed. This lysis may be carried out by a method generally known to those skilled in the art, for example, freezing-thawing, use of a surfactant, or a combination thereof. For example, Triton X-100 (TX100), Nonidet P-40 (NP-40), Tween 20, Tween 80, n-octylglucoside, ZWITTERGENT, Lubrol, or CHAPS may be used as the surfactant. Cell debris and nucleus are removed by centrifugation from the cell lysate containing the solubilized MHC molecule-peptide complexes.

The cell lysate containing the solubilized MHC molecule-peptide complexes may be subjected to immunoprecipitation or immunoaffinity chromatography to purify the MHC molecule-peptide complexes. An antibody that is specific for each MHC molecule and is suitable for immunoprecipitation or immunoaffinity chromatography (anti-MHC I molecule antibody, for example, anti-HLA-A antibody, anti-HLA-B antibody, anti-HLA-C antibody, or anti-HLA-ABC antibody, etc.; or anti-MHC II molecule antibody, preferably anti-HLA-DR antibody, anti-HLA-DQ antibody, or anti-HLA-DP antibody) may be used for these methods. The specific antibody is preferably a monoclonal antibody and may be conjugated with beads (e.g., Sepharose beads or agarose beads) through a covalent bond or a noncovalent bond, for example, via protein A. For example, the amino group of the antibody may be covalently bonded to CNBr-activated Sepharose so that the antibody is immobilized thereon. A commercially available product may be purchased as the monoclonal antibody, or the monoclonal antibody may be purified from the supernatant of each corresponding hybridoma cell using protein A- or protein G-affinity chromatography.

The MHC molecules may be immunoisolated, for example, by performing incubation while rotating the antibody-beads together with the cell lysate for a few hours. Also, the antibody-beads bound with the MHC molecule-peptide complexes may be washed in an Eppendorf tube. The results of immunoprecipitation may be analyzed by SDS-PAGE and Western blotting using an antibody that recognizes a denatured MHC molecule.

A mixture of peptides that are derived from the target protein through the decomposition by the antigen-presenting cell is obtained by eluting the peptides from the complexes formed with the MHC molecules.

The peptides may be eluted by a method generally known to those skilled in the art, for example, by use of a diluted acid, for example, diluted acetonitrile (Jardetzky T S et al., Nature 1991 353, 326-329), diluted acetic acid and heating (Rudensky A Y et al., Nature 1991, 353, 622-626; and Chicz R M et al., Nature 1992, 358, 764-768), or diluted trifluoroacetic acid (Kropshofer H et al., J Exp Med 1992, 175, 1799-1803). The peptides are preferably eluted with diluted trifluoroacetic acid, for example, at 37° C.

Before the elution of the peptides from the MHC molecule-peptide complexes, these complexes may be washed with water or a low-salt buffer solution in order to remove surfactant residues. A Tris buffer solution, a phosphate buffer solution, or an acetate buffer solution having a concentration of 0.5 to 10 mM may be used as the low-salt buffer solution. Alternatively, the MHC molecule-peptide complexes may be washed with ultrapure water for HPLC. This washing may be performed by ultrafiltration. The ultrafiltration may be performed in an ultrafiltration tube having, for example, a cutoff value of 30 kD, 20 kD, 10 kD, or 5 kD and a tube volume of 0.5 to 1.0 ml. The inside of the ultrafiltration tube may be washed, for example, 4 to 12 times, with a washing solution having tens of times the volume of the beads carrying the MHC molecule-peptide complexes.

The peptides may be eluted from the MHC molecule-peptide complexes by use of this ultrafiltration tube. Subsequently, the eluted peptides may be dried by use of freeze drying or a centrifugal evaporator.

The peptide mixture thus eluted may be fractionated and subjected to sequence analysis by use of liquid chromatography mass spectrometry (LC/MS) to identify (the amino acid sequence of) each peptide.

The amino acid sequence of each peptide in the peptide mixture can be determined by the sequence analysis according to a method known in the art sufficient for sequencing a fmol amount of peptides.

The identification reveals a protein from which the peptide is derived, and a sequence from which the peptide is derived in the protein.

The eluted peptide mixture is preferably fractionated, for example, using reverse-phase chromatography and anion-exchange chromatography or cation-exchange chromatography in combination or reverse-phase chromatography alone. The fractionation may be performed on a HPLC mode using a fused-silica micro-capillary column connected either to nanoflow electrospray ion source in a mass spectrometer or to a microfractionation apparatus that spots fractions on a plate for MALDI analysis.

Electrospray ionization tandem mass spectrometry (ESI-MS) or MALDI-post source decay (PSD) MS may be used as a mass spectrometry technique, and ESI-MS is preferred.

In the sequence analysis, the amino acid sequence of each peptide may be determined by various approaches generally known to those skilled in the art. The sequence analysis may be performed by the computer analysis of a peptide fragment spectrum using, for example, MASCOT algorithm or SEQUEST algorithm. These algorithms preferably employ protein and nucleotide sequence databases, for conducting the cross-correlation analysis of experimentally and theoretically prepared tandem mass spectra. This permits automatic high-throughput sequence analysis.

Matrix-assisted laser desorption ionization time-of-flight (MALDI-TOF) mass spectrometry may be performed for the qualitative analysis of all of the peptides obtained by elution. The MALDI-TOF analysis can provide a rough outline regarding the complexity of the peptide mixture and the presence of a primary peptide.

In order to estimate the amount of each single peptide eluted from the complex with the MHC molecule, substances that have passed through a microcapillary column may be analyzed using a UV detector at a detection wavelength of 214 nm. The peak area of the peptide to be analyzed may be compared with the peak areas of serial amounts of standard peptides (control) to estimate the amount of the peptide.

A set of peptides that are derived from the target protein by natural fragmentation in the antigen-presenting cell is obtained by eluting the peptides from the MHC molecules. For identifying and excluding false-positive peptides, it is preferred that a set of antigen-presenting cells exposed to the target protein as well as a set of antigen-presenting cells unexposed to the target protein as a negative control should be prepared and analyzed by comparison. A peptide that can be detected in only the antigen-presenting cells exposed to the target protein as compared with the antigen-presenting cells unexposed to the target protein may be identified as functioning as an epitope on the protein from which the peptide is derived, and having antigenicity.

Whether or not the identified peptide functions as an epitope can be tested by using, for example, a MHC-binding motif, the ability to bind to MHC, or recognition by helper T cells as an index. Alternatively, this test may be appropriately combined with an in silico epitope prediction algorithm.

The MHC-binding motif means a structural feature that is common in peptides binding to particular MHC molecules (allelic polymorphism) and is necessary for forming stable complexes with the MHC molecules. In the case of MHC II molecules, the peptide length varies from 12 to 18 amino acids, and even longer peptides can bind because both ends of the peptide-binding groove are open. Most of MHC II molecules can accommodate up to 4 residues (called "anchor residues") related to the binding, at relative positions P1, P4, P6 and P9 contained in a nonameric core region. However, this core region may vary in distance from the N terminus of the peptide. In many cases, 2 to 4 N-terminal residues precede the core region. Thus, the P1 anchor residue is located at position 3, 4, or 5 in many peptides that can form with complexes with the MHC II molecules. Peptides eluted from, for example, HLA-DR molecules can share a hydrophobic P1 anchor such as tyrosine, phenylalanine, tryptophan, methionine, leucine, isoleucine, or valine. The positions and types of the anchor residues can be estimated from the peptide-binding motifs of frequently occurring MHC molecules. A computer algorithm that permits motif validation in peptide sequences can be obtained from, for example, "Tepitope" (www.vaccinome.com, J. Hammer, Nutley, USA).

The ability to bind to MHC may be tested by a method generally known to those skilled in the art using the detected peptide itself (e.g., a synthetic peptide may be utilized) and a desired MHC molecule (Kropshofer H et al., J. Exp. Med. 1992, 175, 1799-1803; Vogt A B et al., J. Immunol. 1994, 153, 1665-1673; and Sloan V S et al., Nature 1995, 375, 802-806). Alternatively, cellular binding assay using MHC molecule-expressing cell lines and biotinylated peptides may be used to test the ability to bind to MHC (Arndt S O et al., EMBO J., 2000, 19, 1241-1251). The relative ability of each peptide to bind to MHC may be determined by measuring a concentration necessary to reduce the binding of a labelled reporter peptide to 50% (IC50). In this context, each identified peptide may be used as such a peptide, or a peptide having a sequence common in identified peptides (core sequence) may be used. The peptide to be detected is considered to depend on the types of MHC molecule allotypes, the strength of binding affinity for a MHC molecule, etc.

The ability to stimulate helper T cells is particularly important for testing whether the identified peptide functions as an epitope. When each identified peptide stimulates helper T cells, this may be used as one index for determining that the peptide has immunogenicity. This determination method may involve testing whether the peptide identified by the method of the present invention has the ability to activate helper T cells. Each identified peptide may be used as such a peptide, or a peptide having a sequence common in identified peptides (core sequence) may be used.

The cellular response of helper T cells may be measured by various in vitro methods generally known to those skilled in the art. For example, MHC molecule-expressing cells (e.g., monocytes, macrophages, or dendritic cells) are cultured together with helper T cells in the presence of the peptide to be evaluated. The uptake of radioactive material-labeled thymidine (T) during DNA replication may be measured with helper T cell proliferation as an index. Alternatively, 5-bromo-2'-deoxyuridine (BrdU) may be used instead of thymidine. In such a case, helper T cells that have taken up BrdU during DNA replication are treated with a monoclonal antibody against BrdU. Then, the amount of BrdU taken up may be measured using an enzymatically or fluorescently labeled secondary antibody (e.g., 5-Bromo-2'-deoxyuridine Labeling & Detection Kit III, Roche-Biochem, Cat No. 1 444 611). Alternatively, Naive Primary T cell Assay (Proimmune Ltd.) which employs flow cytometry using the dilution of a fluorescent dye label 5,6-carboxyfluorescein diacetate succinimidyl ester (CFSE) by the proliferation of helper T cells as an index may be used in the measurement. Alternatively, the cellular response of helper T cells may be evaluated by measuring various cytokines produced from the helper T cells, instead of measuring the cell proliferation. Examples of such cytokines include IL-2, IL-4, IL-6, IL-10, IL-12, IFN-γ, and transforming growth factor-β (TGF-β). Examples of the method for measuring the cytokines include various methods generally known to those skilled in the art, for example, ELISA and ELISPOT.

Preferably, dendritic cells produced by the method for producing a dendritic cell from a stem cell or a progenitor cell derived therefrom according to the present invention as mentioned above may be used as the MHC molecule-expressing cells. The MHC molecule-expressing cells may be rendered non-proliferative, for example, by treatment with ionizing radiation or mitomycin C before the assay.

In an alternative aspect, the present invention also relates to a method for producing a protein with reduced or eliminated immunogenicity, comprising the following steps:

(1) identifying an epitope on a protein according to the aforementioned method;

(2) modifying the epitope to reduce or eliminate the binding of the epitope to a MHC molecule; and (3) producing a protein having the modified epitope.

In a further alternative aspect, the present invention also relates to a protein obtained or obtainable according to the production method. The "obtainable protein" may mean a protein that can be obtained provided that the production method is used.

In relation to the step (2), the amino acid sequence of the identified epitope peptide can be altered or modified to reduce or eliminate the binding of the epitope peptide to a MHC molecule or reduce or eliminate the immunogenicity. The reduction or elimination of the immunogenicity is determined by a method generally known to those skilled in the art without particular limitations and may be determined by using, for example, the aforementioned MHC-binding motif, ability to bind to MHC, or recognition by helper T cells as an index. Alternatively, this approach may be appropriately combined with an in silico epitope prediction algorithm.

The alteration or the modification may be performed according to a method generally known to those skilled in the art. For example, a DNA nucleotide sequence encoding the amino acid sequence of a protein comprising the epitope may be subjected to, for example, site-directed mutagenesis or homologous recombination for the insertion, substitution, or deletion, etc., of desired one or more nucleotides in the DNA sequence. Preferably, for example, one or more anchor residues important for binding to a MHC molecule are changed to other amino acid residues, whereby the immunogenicity can be reduced or eliminated. Alternatively, amino acid residue(s) important for the recognition of the epitope by, for example, T cell receptor on helper T cells or B cell receptor on B cells may be changed to other amino acid residues. The method for replacing the anchor residues important for binding to a MHC molecule is well known to those skilled in the art. For example, the P1 anchor of a HLA-DR1-restricted T cell epitope may be replaced with alanine, proline, glycine, or a charged amino acid residue (Kropshofer et al., EMBO J. 15, 1996, 6144-6154).

In relation to the step (3), the protein having the modified epitope may be chemically synthesized or may be genetically or biologically synthesized. In the case of genetic or biological synthesis, host cells or animals transiently or permanently harboring the gene of the protein having the modified epitope may be utilized. The host cells or the animals can be used, for example, as a production system for protein production or expression. Eukaryotic cells or prokaryotic cells may be used as the host cells.

Examples of the eukaryotic cells that can be used as the host cells include animal cells, plant cells, and fungal cells. Examples of the animal cells include: mammalian cells, for example, CHO (Puck et al., (1958) J. Exp. Med. 108 (6): 945-956), COS, HEK293, 3T3, myeloma, BHK (baby hamster kidney), HeLa, and Vero; amphibian cells, for example, Xenopus oocyte cells (Valle et al., Nature (1981) 291: 338-340); and insect cells, for example, Sf9, Sf21, and Tn5. CHO cells are preferred for the purpose of large-scale expression in the animal cells. The host cells may be transfected with a vector having the gene of the protein having the modified epitope by a method, for example, a calcium phosphate method, a DEAE-dextran method, a method using a cationic ribosome DOTAP (manufactured by Boehringer Mannheim), electroporation, or lipofection. For example, *Nicotiana tabacum*-derived cells and *Lemna minor* are known as a protein production system of the plant cells. These cells may be allowed to produce the protein by a callus culture method. A protein expression system using cells of a yeast, for example, the genus *Saccharomyces* (*Saccharomyces cerevisiae*, *Saccharomyces pombe*, etc.), or cells of a filamentous fungus, for example, the genus *Aspergillus* (*Aspergillus niger*, etc.) may be used as the fungal cells. In the case of using the prokaryotic cells, a production system using bacterial cells may be used. For example, *E. coli* or *Bacillus subtilis* cells may be used as the bacterial cells.

Examples of the animals include genetically recombinant animals and transgenic animals. The type of the animals is not limited, and, for example, cattle, sheep, or mice may be used. In such a case, for example, the protein secreted into a body fluid such as milk may be recovered.

In the present invention, the protein having the modified epitope may be produced at a large scale continuously or commercially. The produced protein or a composition comprising the protein (e.g., a pharmaceutical composition) is also included in the present invention.

In an alternative aspect, the present invention also relates to a method for predicting whether or not a protein has immunogenicity in a subject, comprising the steps of (I) providing a cell expressing one or more MHC molecule allotypes in the subject intended to receive the target protein, wherein the cell is differentiated from a stem cell or a progenitor cell derived therefrom;

(II) contacting the "cell expressing one or more MHC molecule allotypes" with the target protein;

(III) isolating a complex of a peptide contained in the target protein and the MHC molecule from the "cell expressing one or more MHC molecule allotypes";

(IV) eluting the peptide from the complex and identifying the peptide; and (V) optionally testing whether or not the identified peptide is an epitope that induces immunogenicity, wherein when the identified peptide is an epitope that induces immunogenicity, this indicates that the target protein has immunogenicity in the subject.

Those skilled in the art can understand that the prediction method can be carried out by one of or an appropriate combination of two or more of the technical features described above in the present specification.

The prediction method also permits comparison of the presence or absence or the degree of immunogenicity based on each MHC molecule allotype or allotype set against the predetermined protein.

In the prediction method, it is further preferred that one or more cells expressing one or more MHC molecule allotypes in the subject should be provided such that all sets of MHC molecule allotypes carried by the subject are contained therein. The stem cell is still more preferably a stem cell (e.g., an iPS cell or ES cell) derived from the subject (e.g., a mammal, preferably a human). This is because antigen-presenting cells differentiated from stem cells maintain MHC molecule allotypes; thus, antigen-presenting cells that cover all sets of MHC molecule allotypes carried by the subject can be produced by use of the stem cell derived from the subject. Whether or not the target protein has immunogenicity in each subject (e.g., human patient or healthy person) may be evaluated individually by use of such antigen-presenting cells (accomplishment of individual medicine). In other words, the prediction method also relates to a method for selecting a subject (e.g. a patient) having immunogenicity or a method for selecting a subject (e.g. a patient) free from immunogenicity. Alternatively, the prediction method also relates to a method for indicating that one or more particular MHC molecule allotypes are involved in immunogenicity in association with a protein intended to be administered.

It is considered that genes that define MHC molecule allotypes (HLA genotypes in humans) are preserved in almost all of somatic cells in one individual. Thus, the stem cell (e.g., an iPS cell or an ES cell) derived from the subject (e.g., a mammal, preferably a human) may be prepared from any somatic cell or the like of the subject as long as the stem cell maintains the MHC molecule allotypes. Examples of the somatic cell are not particularly limited, and, for example, iPS cells can also be prepared from PBMCs separated from a human or the like. Examples of such reports include Soares F A, Pedersen R A, Vallier L., Generation of Human Induced Pluripotent Stem Cells from Peripheral Blood Mononuclear Cells Using Sendai Virus, Methods Mol Biol. 2015 Feb. 17; Quintana-Bustamante O, Segovia J C., Generation of Patient-Specific induced Pluripotent Stem Cell from Peripheral Blood Mononuclear Cells by Sendai Reprogramming Vectors, Methods Mol Biol. 2014 Dec. 19; Su R J, Neises A, Zhang X B., Generation of iPS Cells from Human Peripheral Blood Mononuclear Cells Using Episomal Vectors, Methods Mol Biol. 2014 Nov. 18; and Riedel M, Jou C J, Lai S, Lux R L, Moreno A P, Spitzer K W, Christians E, Tristani-Firouzi M, Benjamin I J., Functional and pharmacological analysis of cardiomyocytes differentiated from human peripheral blood mononuclear-derived pluripotent stem cells, Stem Cell Reports. 2014 May 29; 3 (1): 131-41. A large number of methods, as listed in the present specification, have been reported as methods for establishing antigen-presenting cells such as dendritic cells from stem cells such as iPS cells. Thus, those skilled in the art should understand that, for example, after preparation of stem cells such as iPS cells from cells such as PBMCs separated from the predetermined subject (e.g. a human patient), antigen-presenting cells such as dendritic cells can be established using the stem cells and thereby utilized in the prediction method. In this respect, the subject-derived cells for use in the preparation of stem cells such as iPS cells may be cells whose MHC molecule allotypes (HLA genotypes in humans) can be identified, or cells whose MHC molecule allotypes have already been revealed (or predicted). Alternatively, iPS cells whose MHC molecule allotypes have already been revealed (or predicted) may be used.

In a further alternative aspect, the present invention relates to a composition for the treatment and/or prevention of a disease related to a protein, in a subject, comprising the protein as an active ingredient, wherein the subject is selected from (only) subjects predicted to be free from the immunogenicity of the protein according to the aforementioned prediction method. The "composition for the treatment and/or prevention" preferably comprises a therapeutically and/or prophylactically effective amount of the protein, and the effective amount of the protein can be appropriately determined by those skilled in the art. Also, the "composition for the treatment and/or prevention" may contain one or more additional agents.

The term "predicted to be free from the immunogenicity of the protein" may mean that the target protein does not evoke any immunogenicity in the subject or merely evokes immunogenicity to an extent tolerable from the viewpoint of efficacy, safety, etc.

It is preferred that the protein or the composition for the treatment and/or prevention comprising the protein as an active ingredient should be administered to only a subject predicted to be free from immunogenicity, by preparing cells expressing one or more MHC molecule allotypes according to a race, an ethnic group, a population, or an individual person, and evaluating the immunogenicity of the protein. The composition is preferably a pharmaceutical composition.

When the protein is contained in the (pharmaceutical) composition for use, the (pharmaceutical) composition can be formulated and used by a pharmaceutical production method known in the art. The (pharmaceutical) composition can be used, for example, orally as an optionally sugar-coated tablet, a capsule, an elixir, or a microcapsule, or parenterally (e.g., percutaneously, intranasally, transbronchially, intramuscularly, or intravenously) in the form of an aseptic solution or suspension containing the protein in water or any of other pharmaceutically acceptable solutions. The (pharmaceutical) composition may be produced so as to appropriately contain a pharmaceutically acceptable carrier, flavor, excipient, vehicle, antiseptic, stabilizer, or binder. For example, a binder such as gelatin, corn starch, gum tragacanth, or gum arabic, an excipient such as crystalline cellulose, a swelling agent such as corn starch, gelatin, or alginic acid, a lubricant such as magnesium stearate, a sweetener such as sucrose, lactose, or saccharin, and a flavor such as peppermint, Akamono oil, or cherry may be used as additives that can be mixed into tablets or capsules. When the unit dosage form is a capsule, this capsule can further contain a liquid carrier such as oil and fat in addition to the materials described above. The aseptic solution for injection can be formulated according to a method well known to those skilled in the art using a vehicle such as injectable distilled water. Examples of the aqueous solution for injection include physiological saline and isotonic solutions containing glucose or other adjuvants, for example, D-sorbitol, D-mannose, and D-mannitol. An appropriate solubilizer, for example, an alcohol such as ethanol, a polyalcohol such as propylene glycol or polyethylene glycol, or a nonionic surfactant such as polysorbate 80™ or HCO-50 may be further used in combination therewith. Examples of the oily liquid include sesame oil and soybean oil, which may be used in combination with a solubilizer, for example, benzyl benzoate or benzyl alcohol. For example, a buffer such as a phosphate buffer solution or a sodium acetate buffer solution, for example, a soothing agent such as procaine hydrochloride, for example, a stabilizer such as benzyl alcohol or phenol, or an antioxidant may also be contained therein. The prepared injection solution may usually be filled into an appropriate ampule for use.

The dose, administration method, dosing intervals, etc., of the protein or the composition for the treatment and/or prevention comprising the protein as an active ingredient varies depending on the body weight, age, symptoms, etc., of a patient and can be appropriately selected and determined by those skilled in the art.

As for the "disease related to a protein", the protein and the disease related to the protein are not particularly limited. The protein is still more preferably a protein that may cause, for example, immunogenicity or problems associated with efficacy or safety when administered into an organism. Examples of the disease include, but are not limited to, autoimmune diseases (e.g., rheumatoid arthritis, type I diabetes, multiple sclerosis (MS), coeliac disease, myasthenia gravis (MG), and systemic lupus erythematosus (SLE)), cancers (e.g., melanoma, breast cancer, B cell lymphomas, prostate cancer, and renal cancer), and infectious diseases (e.g. diseases caused by HIV, hepatitis C virus, measles virus, and mycobacteria).

Examples of a combination of such a protein and a disease related to the protein may include examples described in Self/Nonself 2010; 1 (4) pp. 314-322; PHARM TECH JAPAN Vol. 28, No. 10 (2012), pp. 117 (2065)-126 (2074); Sorensen, P. S., et al., Neurology, 67 (9), 1681-3 (2006); Hesse, D., et al., Eur. J. Neurol., 14 (8), 850-9 (2007); Casadevall, N., et al., N. Engl. J. Med., 346 (7), 469-75 (2002); Gershon, S. K., et al., N. Eng. J. Med., 346 (20), 1584-6 (2002); and Locatelli F., et al., Perit. Dial. Int., 27 (Supp12), S303-7 (2006).

Specific examples of the combination of the protein and the disease related to the protein include, but are not limited to: muromonab and allograft rejection; abciximab and PTCA adjunct; rituximab and non-Hodgkin lymphoma; daclizumab and transplant rejection; trastuzumab and breast cancer; palivizumab and RSV prophylaxis; basiliximab and transplant rejection; infliximab and rheumatoid arthritis or Crohn; arcitumomab and colorectal cancer; canakinumab and cryopyrin-associated periodic syndrome; fanolesomab and imaging for appendicitis; imciromab and cardiac imaging for MI; capromab and prostate cancer diagnostic; nofetumomab and detection of SCLC; gemtuzumab and acute myeloid leukemia; alemtuzumab and B cell chronic lymphocytic leukemia; ibritumomab and non-Hodgkin lymphoma; adalimumab and rheumatoid arthritis, Crohn, PsA, JIA, ankylosing spondylitis, or plaque psoriasis; omalizumab and asthma; efalizumab and psoriasis; tositumomab and non-Hodgkin lymphoma; cetuximab and colorectal cancer; bevacizumab and colorectal, breast, renal or NSCL cancer; panitumumab and colorectal cancer; ranibizumab and macular degeneration; eculizumab and paroxysmal nocturnal hemoglobinuria; natalizumab and multiple sclerosis (MS) or Crohn; golimumab and rheumatoid arthritis, PsA, or ankylosing spondylitis; cetolizumab pegol and rheumatoid arthritis or Crohn; ofatumumab and CLL; ustekinumab and plaque psoriasis; tocilizumab and rheumatoid arthritis; denosumab and osteoporosis; Prolastin and α1-antitrypsin deficiency; Aralast and α1-antitrypsin deficiency; Zemaira and α1-antitrypsin deficiency; Kogenate F S and hemophilia A; ReFacto and hemophilia A; Zyntha and hemophilia A; NovoSeven and hemophilia; Benefix and hemophilia B; ATryn and thromboembolism; BabyBIG and infant botulism; Berinert and angioedema; Cinryze and angioedema; Rhophylac and ITP; Evithrom and coagulation; Recothrom and coagulation; Wilate and coagulation; Cerezyme and Gaucher disease; exenatide or Byetta and type II diabetes; Intron A and leukemia, Kaposi sarcoma, or hepatitis B/C; Betaseron and multiple sclerosis; NovoLog and type II diabetes; Leukine and preventing infection in cancer; NEUPOGEN and preventing infection in cancer; Retavase and myocardial infarction or pulmonary embolism; Humatrope and dwarfism; Adagen and inherited immunodeficiency; Pulmozyme and cystic fibrosis; Procrit and anemia in chronic renal disease; and Proleukin and oncology.

In a further alternative aspect, the present invention relates to [30] a method for treating and/or preventing a disease related to a protein, comprising the step of administering the protein to a subject in need of the treatment and/or prevention, wherein the subject is selected from (only) subjects predicted to be free from the immunogenicity of the protein according to the aforementioned prediction method.

In a further alternative aspect, the present invention relates to [31] use of a protein for the production of a medicament for the treatment and/or prevention of a disease related to the protein, wherein a subject of the treatment and/or prevention is selected from (only) subjects predicted to be free from the immunogenicity of the protein according to the aforementioned prediction method.

In a further alternative aspect, the present invention relates to use of a stem cell or a progenitor cell derived therefrom, or a MHC molecule-expressing cell differentiated from the stem cell or the progenitor cell in various methods according to the present invention described above.

Those skilled in the art can understand that these aspects of the present invention can be carried out by one of or an appropriate combination of two or more of the technical features described in the present specification.

Those skilled in the art should understand that one of or any combination of two or more of the aspects described in the present specification is also included in the present invention unless a technical contradiction arises on the basis of the technical common sense of those skilled in the art.

The terms in the present specification are used for illustrating particular embodiments and are not intended to limit the invention. The terms (including technical terms and scientific terms) used in the present specification are interpreted to have the same meanings as those understood in a broad sense by those skilled in the art to which the present invention belongs, unless otherwise defined. These terms used in the present specification should not be interpreted in an idealized or excessively formal sense, unless otherwise defined.

The term "comprise" used in the present specification means that described items (members, steps, factors, numbers, etc.) are present and the presence of the other items (members, steps, factors, numbers, etc.) is not excluded therefrom, unless the context evidently requires different interpretation.

The embodiments of the present invention may be described with reference to a schematic diagram, which may be exaggerated for the purpose of clear illustration.

All literatures (Patent Literatures and Non Patent Literatures) described in the present specification may be incorporated herein by reference in their entirety. The present invention can be understood by appropriately referring to the contents thereof in light of the technical common sense of those skilled in the art.

The numeric values described in the present specification are understood as values having given ranges according to the technical common sense of those skilled in the art, unless inconsistent to the context. For example, the term "1 mg" is understood to represent "approximately 1 mg" and is understood to include a given variation. For example, the term "1 to 5" described in the present specification is understood to concretely describe the individual values of "1, 2, 3, 4, and 5", unless inconsistent to the context.

Hereinafter, the present invention will be described in detail with reference to Examples. However, the present invention can be embodied by various aspects and should not be interpreted as being limited to Examples described herein.

Each noun described in the present specification and claims is intended to indicate that one or more objects may be present unless otherwise specified in the present specification and claims and unless a contradiction arises in the context.

EXAMPLES

A. Method
—Cells Used—
Human iPS cells: Tic (JCRB1331), obtained from JCRB Cell Bank; and 201B7, obtained from iPS Academia Japan, Inc.

Feeder cells: EmbryoMax Primary Mouse Embryonic Fibroblasts (MEF), Hygro resistant, C57BL/6 (purchased from Merck Millipore Corp., Cat.: PMEF-HL); and SNL 76/7 feeder cells (SNL) (purchased from Cell Biolabs, Inc., Cat.: CBA-316).

—Culture Method for Maintaining Undifferentiated Human iPS Cells (Tic)—

1. Gelatin from porcine skin (Sigma-Aldrich Corp., Cat.: G1890) diluted to 0.1% with distilled water was prepared in a sol form by warming, added in an amount of 2 mL to each 60-mm dish, and left at 37° C. for 30 to 180 minutes under 5% $CO_2$ conditions to prepare a gelatin-coated dish.

2. Feeder cells (MEF) were suspended in DMEM (Gibco, Cat.: 10569-010) supplemented with 10% Embryonic Stem Cell Fetal Bovine Serum (FBS) (Gibco, Cat.: 10439-024), 2 mM L-glutamine (Invitrogen Corp., Cat.: 25030-081), and 0.5% Penicillin/Streptomycin (Invitrogen Corp., Cat.: 15140-122), diluted to 1 to $2\times10^5$ cells/mL, inoculated in an amount of 4 mL to each gelatin-coated dish, and cultured at 37° C. for 1 day under 5% $CO_2$ conditions.

3. Culture for maintaining the undifferentiation of human iPS cells was carried out at 37° C. under 5% $CO_2$ conditions in the feeder cell-inoculated 60-mm dish using iPSellon (Cardio Inc., Cat.: 007101) supplemented with 10 ng/mL basic fibroblast growth factor (bFGF) (Wako Pure Chemical Industries, Ltd., Cat.: 064-04541).

4. A colony that differentiated in response to the proliferation of the cells was removed with a scraper. After reaction with 2 U/mL Neutral protease, grade I (Roche Applied Science, Cat.: 04 942 086 001), the feeder cells dissociated first were removed from the dish. Then, a colony of the human iPS cells was recovered from the dish using a scraper, suspended in iPSellon supplemented with 10 ng/mL bFGF, and inoculated to a newly feeder cell-inoculated 60-mm dish, and the culture was continued at 37° C. under 5% $CO_2$ conditions.

—Culture Method for Maintaining Undifferentiated Human iPS Cells (201B7)—

1. Gelatin from porcine skin diluted to 0.1% with distilled water was prepared in a sol form by warming, added in an amount of 2 mL to each 60-mm dish, and left at 37° C. for 30 to 180 minutes under 5% $CO_2$ conditions to prepare a gelatin-coated dish.

2. Feeder cells (SNL) were suspended in DMEM (Gibco, Cat.: 10569-010) supplemented with 7% FBS, 2 mM L-glutamine, and 0.5% Penicillin/Streptomycin, diluted to 1 to $2\times10^5$ cells/mL, inoculated in an amount of 4 mL to each gelatin-coated dish, and cultured at 37° C. for 1 day under 5% $CO_2$ conditions.

3. Culture for maintaining the undifferentiation of human iPS cells was carried out at 37° C. under 5% $CO_2$ conditions in the feeder cell-inoculated 60-mm dish using Primate ES cell medium (ReproCELL Inc., Cat.: RCHEMD001) supplemented with 4 ng/mL bFGF.

4. A colony that differentiated in response to the proliferation of the cells was removed with a scraper. After reaction with 2 U/mL Neutral protease, grade I, the feeder cells dissociated first were removed from the dish. Then, a colony of the human iPS cells was recovered from the dish using a scraper, suspended in Primate ES cell medium supplemented with 4 ng/mL bFGF, and inoculated to a newly feeder cell-inoculated 60-mm dish, and the culture was continued at 37° C. under 5% $CO_2$ conditions.

—Method for Differentiating Human iPS Cells into Monocyte-Like Cells—

1. Matrigel, growth-factor reduced (BD Biosciences, Cat.: 356230) diluted 40-fold with DMEM (Gibco, Cat.: 10569-010) was added in an amount of 2 mL to each 60-mm dish and left at 37° C. for 12 to 72 hours under 5% $CO_2$ conditions to prepare a MG dish.

2. Gelatin from porcine skin (Sigma-Aldrich Corp., Cat.: G1890) diluted into 0.1% with distilled water was prepared in a sol form by warming, added in an amount of 2 mL to each 60-mm dish, and left at 37° C. for 30 to 180 minutes under 5% $CO_2$ conditions to prepare a gelatin-coated dish.

3. As for a colony of human iPS cells cultured with their undifferentiation maintained, 2 U/mL Neutral protease, grade I (Roche Applied Science, Cat.: 04 942 086 001) was added to the dish, and the feeder cells dissociated first were removed from the dish. Then, a colony of the undifferentiated human iPS cells was recovered from the dish using a scraper, suspended in MEM Alpha 1×+Glutamax I (Life Technologies/Thermo Fisher Scientific Inc., Cat.: 32561-037) supplemented with 20% Fetal Bovine Serum, embryonic stem cell-qualified (FBS) (Life Technologies/Thermo Fisher Scientific Inc., Cat.: 16141), 1% L-glutamine (Invitrogen Corp., Cat.: 25030-081), 0.5% Penicillin/Streptomycin (Invitrogen Corp., Cat.: 15140-122), and 55 µM 2-mercaptoethanol (Invitrogen Corp., Cat.: 21985-023), and inoculated in an amount of 4 mL to each gelatin-coated dish from which the supernatant had been removed, and cultured at 37° C. for 1 hour under 5% $CO_2$ conditions so that the feeder cells were attached to the dish bottom and separated from the human iPS cell colony.

Figure 2:
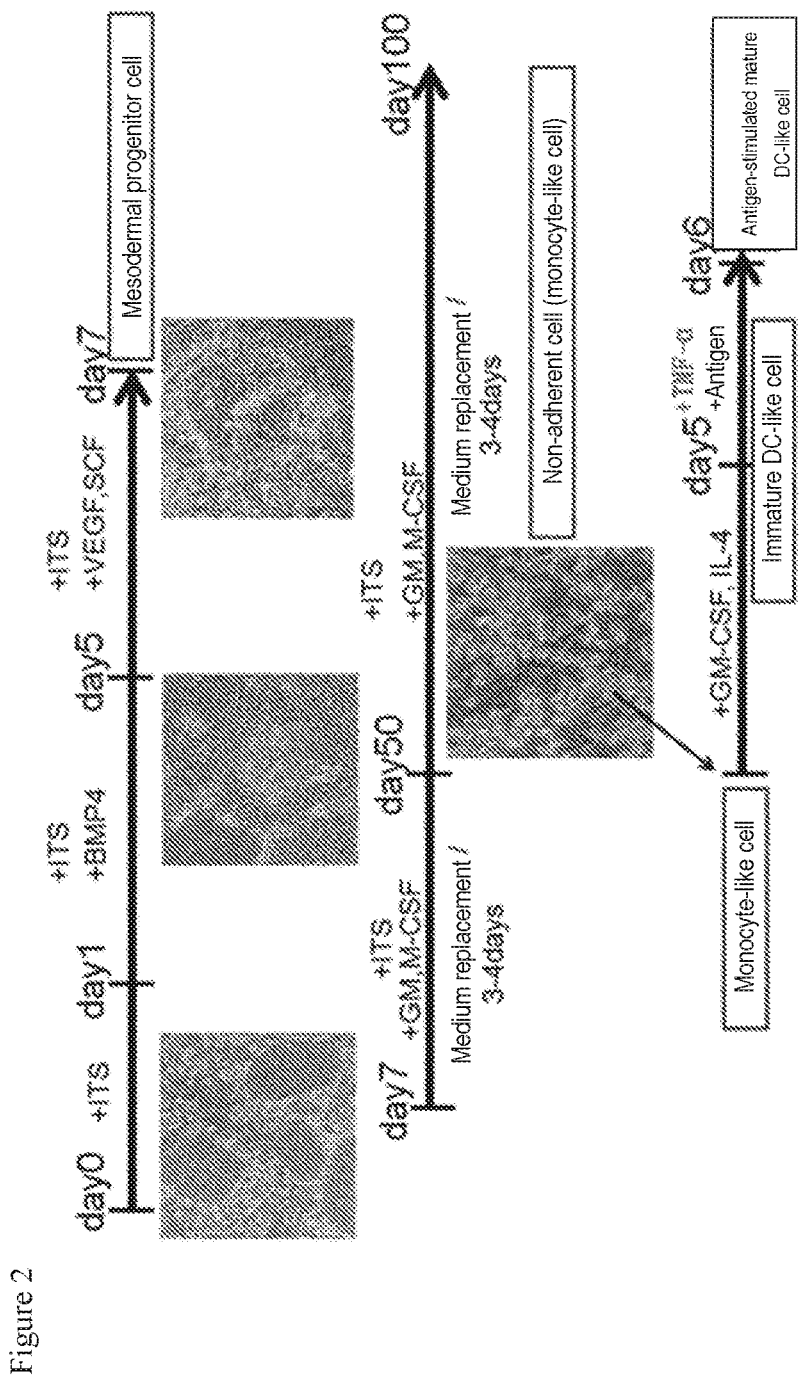
FIG. 2 shows one example of a scheme for obtaining dendritic cell-like cells by the differentiation of human iPS cells.

4. The whole amount of an unattached colony of the human iPS cells was recovered from the gelatin-coated dish, suspended in Primate ES cell medium supplemented with Insulin-Transferrin-Selenium-X 100X (ITS) (Life Technologies/Thermo Fisher Scientific Inc., Cat.: 51500-056) at a dilution ratio of 1/100-fold, inoculated in an amount of 3 mL to each MG dish from which the supernatant had been removed, and cultured at 37° C. for 1 day under 5% $CO_2$ conditions (see the left photograph on the upper column of FIG. 2).

5. After removal of the whole amount of the medium from the dish, Primate ES cell medium supplemented with 1/100-fold ITS and 50 ng/mL recombinant human bone morphogenetic protein 4 (rhBMP4) (HumanZyme, Inc., Cat.: 314-BP) was added in an amount of 7 mL to each dish, followed by culture at 37° C. for 4 days under 5% $CO_2$ conditions (see the middle photograph on the upper column of FIG. 2).

6. After removal of the whole amount of the medium from the dish, Primate ES cell medium supplemented with 1/100-fold ITS, 40 ng/mL recombinant human Vascular Endothelial Growth Factor 165 (rhVEGF165) (R&D Systems, Inc., Cat.: 293-VE), and 50 ng/mL recombinant human Stem Cell Factor (rhSCF) (R&D Systems, Inc., Cat.: 255-SC) was added in an amount of 4 mL to each dish, followed by culture at 37° C. for 2 days under 5% $CO_2$ conditions (see the right photograph on the upper column of FIG. 2).

7. After removal of the whole amount of the medium, StemPro-34 medium (Life Technologies/Thermo Fisher Scientific Inc., Cat.: 10640) supplemented with 1/100-fold ITS, 100 ng/mL recombinant human Granulocyte Macrophage colony-stimulating factor (rhGM-CSF) (HumanZyme, Inc., Cat.: HZ-1082), and 50 ng/mL recombinant human Macrophage colony-stimulating factor (rhM-CSF) (HumanZyme, Inc., Cat.: HZ-1039) was added in an amount of 5 mL to each dish, followed by culture at 37° C. under 5% $CO_2$ conditions during which the culture solution was replaced with a fresh one every 3 to 4 days (see the middle photograph on the lower column of FIG. 2).

8. The operation of Step 7 was continued for 120 days. Non-adherent cells appeared since around culture day 50, and the non-adherent cells were recovered from the dish at a frequency of once per 7 days to 14 days and used as monocyte-like cells.

9. A portion of the prepared monocyte-like cells was recovered, stained with an anti-HLA-DR antibody (BD Biosciences, Cat.: 347364), an anti-human HLA-DQ antibody (BD Biosciences, Cat.: 555563), an anti-human HLA-DP antibody (Santa Cruz Biotechnology, Inc., Cat.: sc-53308), an anti-human HLA-ABC antibody (BD Biosciences, Cat.: 555552), an anti-human CD14 antibody (BD Biosciences, Cat.: 558121), an anti-human CD80 antibody (BD Biosciences, Cat.: 561134), an anti-human CD86 antibody (BD Biosciences, Cat.: 561128), an anti-human CD206 antibody (BD Biosciences, Cat.: 551135), an anti-human CD209 antibody (BD Biosciences, Cat.: 551545), an anti-human CD11b antibody (BD Biosciences, Cat.: 555388), and an anti-human CD11c antibody (BD Biosciences, Cat.: 340544), and analyzed using a flow cytometry apparatus BD FACSCanto™ II (BD Biosciences).

—Antigens Used—

The following positive control proteins were used as proteins having immunogenicity. (1) *Betula verrucosa*, birch pollen allergen 1, Isoform a (Bet v1a) (# Bet v 1.0101; Biomay AG) (amino acid sequence: SEQ ID NO: 1) as a white birch pollen allergen (2) Infliximab (trade name: REMICADE® (Mitsubishi Tanabe Pharma Corp.) (amino acid sequences: heavy chain variable region: SEQ ID NO: 2; heavy chain constant region: SEQ ID NO: 3; light chain variable region: SEQ ID NO: 4; light chain constant region: SEQ ID NO: 5)

Infliximab has been clinically confirmed to elicit an anti-drug antibody (ADA) and thus considered to have an epitope sequence (Self/Nonself 2010; 1 (4) pp. 314-322; Current Rheumatology Report 2005; 7: 3-9; and Current Opinion in Monoclonal Therapeutics 2003; 5 (2): 172-179).

(3) Recombinant human factor VIII (rhFVIII) (trade name: ADVATE® (Baxter) (amino acid sequence: SEQ ID NO: 112)

rhFVIII has been clinically confirmed to elicit an anti-drug antibody (ADA) and thus considered to have an epitope sequence (Simon D. Van Haren et al., Mol Cell Proteomics 2011: 10: M110.002246). Also, rhFVIII has approximately twice the molecular weight of a normal IgG antibody.

(4) Phleum pretense, timothy grass pollen allergen 1 (Phl p1) (trade name: Phl p 1.0102 (Biomay AG) (amino acid sequence: SEQ ID NO: 113)

Phl p1 is a pollen antigen of the family Poaceae and has been reported to have an epitope sequence (Carla Oseroff et al., J of Immunol 2010: 185 (2): 943-955).

—Maturation into Dendritic Cells and Exposure to Antigen—

1. For the recovered monocyte-like cells, the medium was removed, and the cells were suspended at a cell density of $1 \times 10^5$ cells/mL in StemPro-34 medium supplemented with 1/100-fold ITS, 200 ng/mL rhGM-CSF, and 10 ng/mL recombinant human Interleukin-4 (rhIL-4) (HumanZyme, Inc., Cat.: HZ-1075), inoculated in an amount of 3 mL/well to a 6-well plate, and cultured at 37° C. for 5 days under 5% $CO_2$ conditions.

2. 3.3 μg/mL Bet v1a or 10 μg/mL infliximab was added to each well, and subsequently, 10 ng/mL recombinant human Tumor Necrosis Factor-α (rhTNF-α) (HumanZyme, Inc., Cat.: HZ-1014) was added thereto, followed by culture at 37° C. for 1 day under 5% $CO_2$ conditions to yield dendritic cell-like cells. For the addition of rhFVIII or Phl p1, 2 mL of the culture supernatant was removed from each well, and then, 30 μg/mL rhFVIII or 10 μg/mL Phl p1 and subsequently 10 ng/mL rhTNF-α were added to each well, followed by culture at 37° C. for 1 day under 5% $CO_2$ conditions to yield dendritic cell-like cells.

3. The whole amount of the dendritic cell-like cells was recovered from the 6-well plate and spun down at 1200 rpm at 4° C. for 5 minutes. Then, the whole supernatant was removed, and the cells were suspended in 1 mL of DPBS of 4° C. Subsequently, the whole amount thereof was transferred to an Eppendorf tube, and spun down at 2500 rpm at 4° C. for 5 minutes. The whole supernatant was removed, and a pellet of the cells was prepared and stored at −80° C.

4. A portion of the prepared dendritic cell-like cells was recovered, stained with an anti-human HLA-DR antibody, an anti-human HLA-DQ antibody, an anti-human HLA-DP antibody, an anti-human HLA-ABC antibody, an anti-human CD14 antibody, an anti-human CD80 antibody, an anti-human CD86 antibody, an anti-human CD206 antibody, an anti-human CD209 antibody, an anti-human CD11b antibody, and an anti-human CD11c antibody, and analyzed using a flow cytometry apparatus BD FACSCanto™ II.

—Formation of Anti-HLA-DR Beads—

1. An anti-HLA-DR antibody G46-6 (BD Biosciences, Cat.: 555809) was immobilized at a final concentration of 1 mg/mL on CNBr-activated Sepharose beads (GE Healthcare Japan Corp., Cat.: 17-0430-01) to prepare anti-HLA-DR antibody-immobilized beads.

2. The anti-HLA-DR antibody-immobilized beads were stored in PBS (Wako Pure Chemical Industries, Ltd., Cat.: 041-20211) containing 0.02% sodium azide (Wako Pure Chemical Industries, Ltd., Cat.: 190-14901).

—Nanoscale Purification of HLA-DR-Peptide Complex—

1. 1/10-fold 10% Triton X-100 (Roche Diag, Cat.: 11332481001) and 17/5000-fold protease inhibitor mix (a mixture of 11.6 mg/mL PMSF (Nacalai Tesque, Inc., Cat.: 27327-94), 1.7 mg/mL pepstatin A (Sigma-Aldrich Corp., Cat.: P4265-25MG), 1.7 mg/mL chymostatin (Roche Diag, Cat.: 11004638001), 0.8 mg/mL leupeptin (Sigma-Aldrich Corp., Cat.: L9783-25MG), and 133 mg/mL sodium azide (Wako Pure Chemical Industries, Ltd., Cat.: 190-14901)) were added to an ultrapure water (Wako Pure Chemical Industries, Ltd., Cat.: 210-01303) solution supplemented with 20 mM Tris (Sigma-Aldrich Corp., Cat.: T1503-1KG) and 5 mM $MgCl_2$ (Merck KGaA, Cat.: 1.05833.0250) and prepared at pH 7.8 using HCl (Merck KGaA, Cat.: 1.00316.1000), to prepare a lysis buffer.

2. The lysis buffer was added in a 10-fold amount to the frozen pellet of the dendritic cell-like cells under ice cooling conditions and shaken at 1100 rpm at 4° C. for 1 hour in Thermomixer Comfort (Eppendorf AG) to obtain a lysate.

3. The lysate was spun down at 14000 rpm at 4° C. for 10 minutes and thereby separated from cells debris or cell nuclei.

4. The anti-HLA-DR antibody-immobilized beads were added in an amount of 5 to 10 μL with respect to 100 μL of the lysate and shaken overnight at 1100 rpm at 4° C. in a horizontal shaker so that HLA-DR-peptide complexes in the lysate bound to the anti-HLA-DR antibody-immobilized beads.

5. The HLA-DR-peptide complexes bound with the anti-HLA-DR antibody-immobilized beads were spun down at 3000 rpm at 4° C. for 1 minute and then washed once with 500 μL of a lysis buffer and further twice with 500 μL of PBS containing 0.1% Zwittergent 3-12 (Calbiochem, Cat.: 693015).

—Elution of HLA-DR-Related Peptide—

1. The HLA-DR-peptide complexes bound with the HLA-DR antibody-immobilized beads were suspended in 400 μL of ultrapure water, transferred to Ultrafree-MC filter (Durapore PVDF, 0.22 um) (Merck Millipore Corp.), and spun down at 14000 rpm at 4° C. for 10 seconds.

2. The ultrapure water that dropped to the tube bottom was removed, and 400 μL of ultrapure water was added onto the filter, followed by spinning down at 14000 rpm at 4° C. for 10 to 30 seconds. This washing operation was repetitively carried out 10 times.

3. 60 uL of ultrapure water containing 0.1% trifluoroacetic acid (Thermo Fisher Scientific Inc., Cat.: 28904) was added thereto, and a peptide mixture was eluted from the HLA-DR-peptide complexes by incubation at 37° C. for 30 minutes and then spun down at 14000 rpm at 18° C. for 3 minutes. The eluted peptide mixture was dried using vacuum centrifuge 5305C (Eppendorf AG).

—Sequence analysis of peptide by ion trap MS/MS mass spectrometry—

1. The dried peptide mixture was redissolved in 15 μL of ultrapure water containing 2% acetonitrile (Wako Pure Chemical Industries, Ltd., Cat.: 018-19853), 0.5% acetic acid (Merck KGaA, Cat.: 1.00066.0250), and 1% formic acid (Merck KGaA, Cat.: 1.11670.1000). A 5 μL aliquot of this solution was injected to nano-LC Ultimate 3000 RSLC-nano system (Dionex) connected to MS. The LC analysis conditions used are the conditions described in EP1715343A1 or their similar conditions generally known to those skilled in the art, under which the analysis can be conducted using a column packed with a reverse-phase material and an ion-exchange material in combination or a column packed with a reverse-phase material alone and using an appropriate buffer solution. The HPLC column was connected to Orbitrap Elite (Thermo Fisher Scientific Inc.) equipped with a nano-LC electrospray ionization source, and the mass spectrometry was carried out by full scan accurate mass spectrometry and MS-MS according to the protocol of the manufacturer.

2. The sequence analysis of the peptides was carried out using SEQUEST algorithm.

B. Results

—Properties of Differentiated Cells—

Figure 3A:
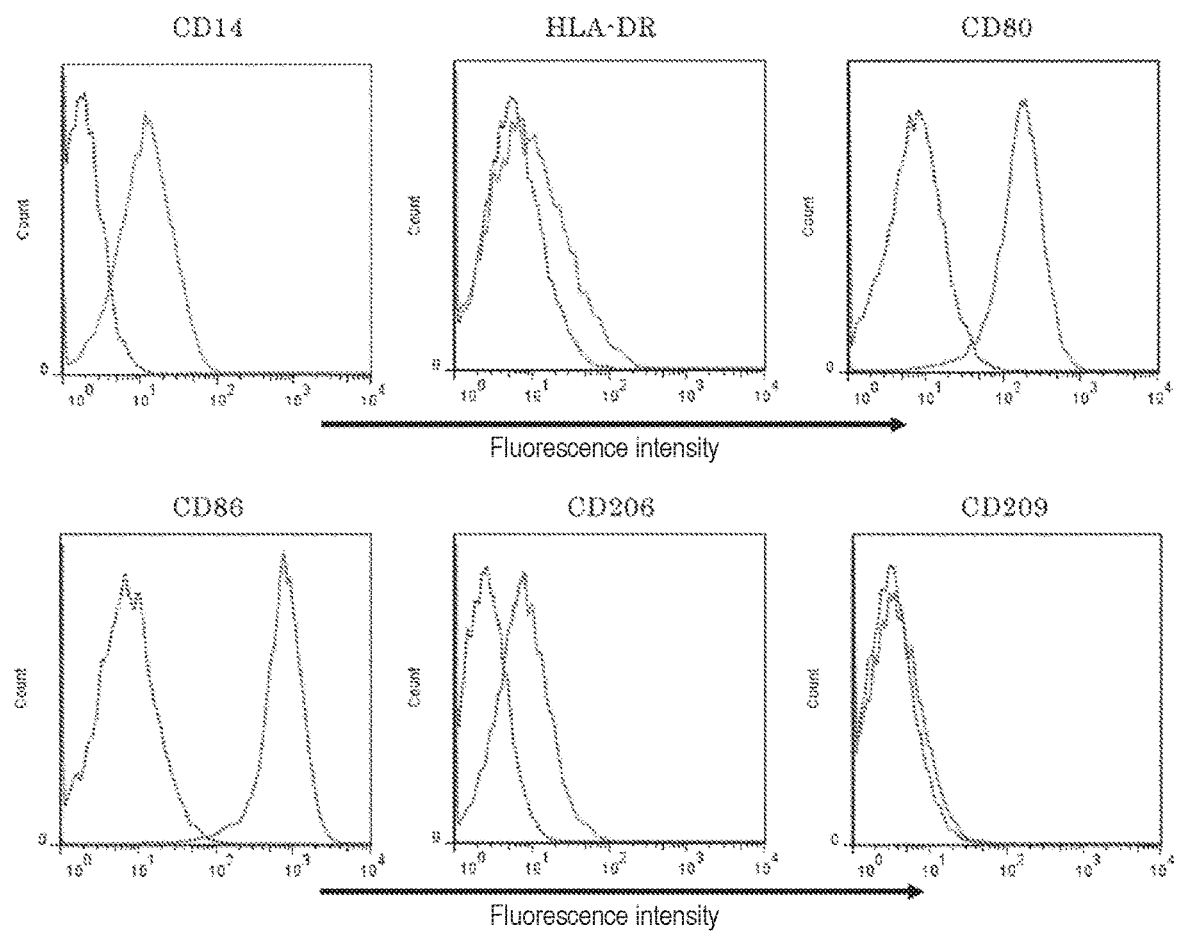
FIG. 3A shows results of examining molecules expressed on the cell surface of monocyte-like cells prepared from a Tic line, wherein the results were obtained by analysis using a flow cytometer.
Figure 3B:
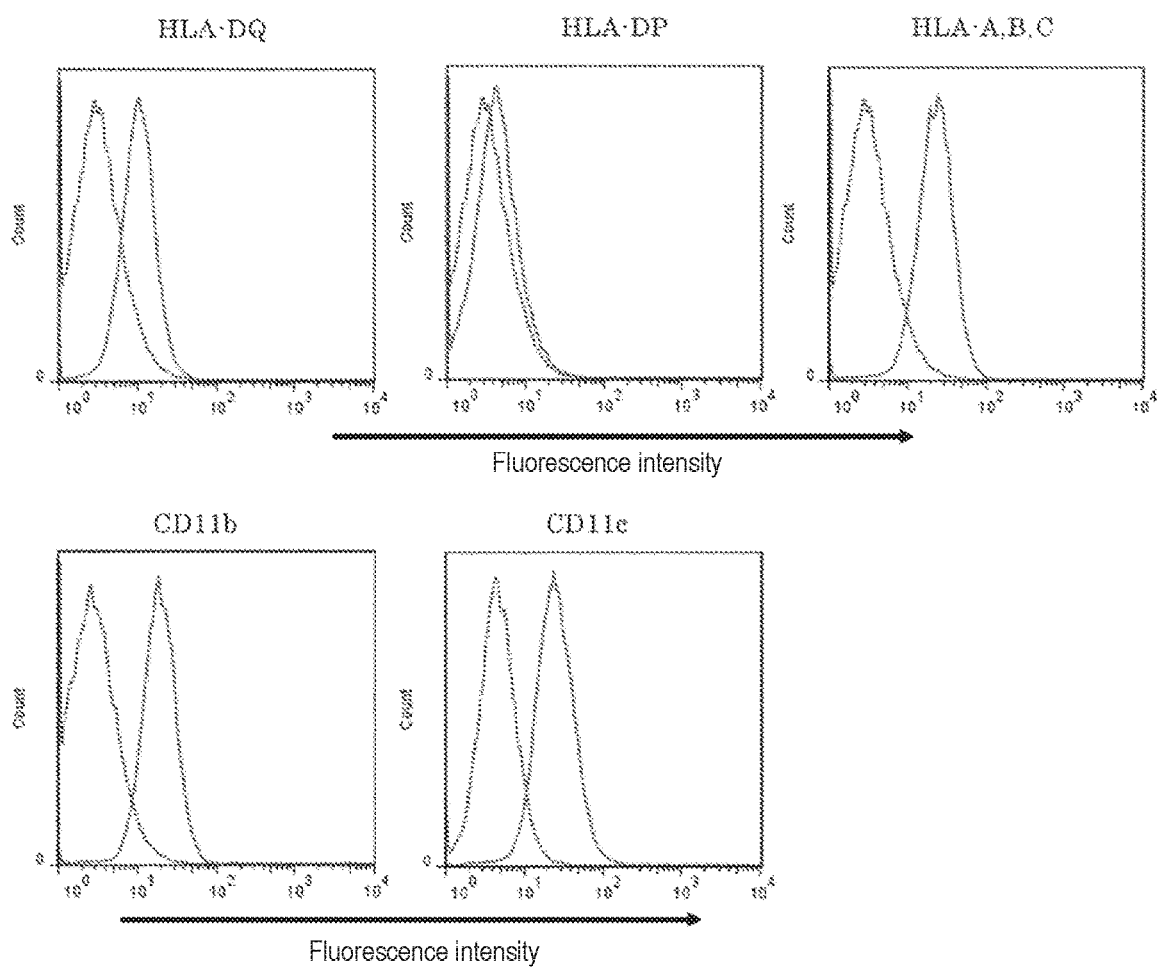
FIG. 3B shows results of examining molecules expressed on the cell surface of monocyte-like cells prepared from a Tic line, wherein the results were obtained by analysis using a flow cytometer.

FIGS. 3A and 3B each show results of examining molecules expressed on the cell surface of the monocyte-like cells prepared using Tic, wherein the results were obtained by analysis using a flow cytometer. The monocyte-like cells obtained by the present Examples were found to express a monocyte-specific marker CD14 and also found to express T cell-activating molecules CD80 and CD86 and adhesion molecules CD11b and CD11c.

Figure 4A:
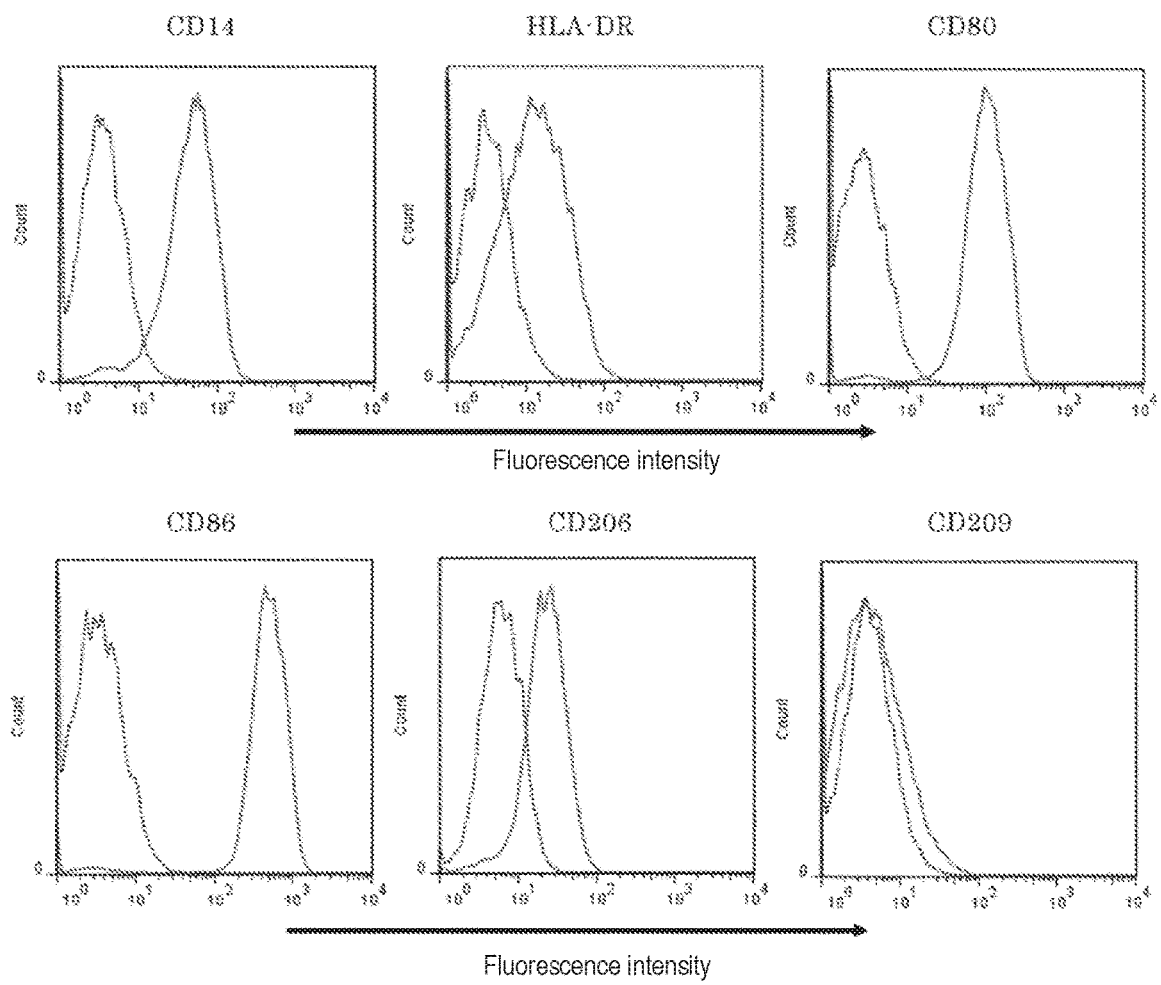
FIG. 4A shows results of examining molecules expressed on the cell surface of monocyte-like cells prepared from a 201B7 line, wherein the results were obtained by analysis using a flow cytometer.
Figure 4B:
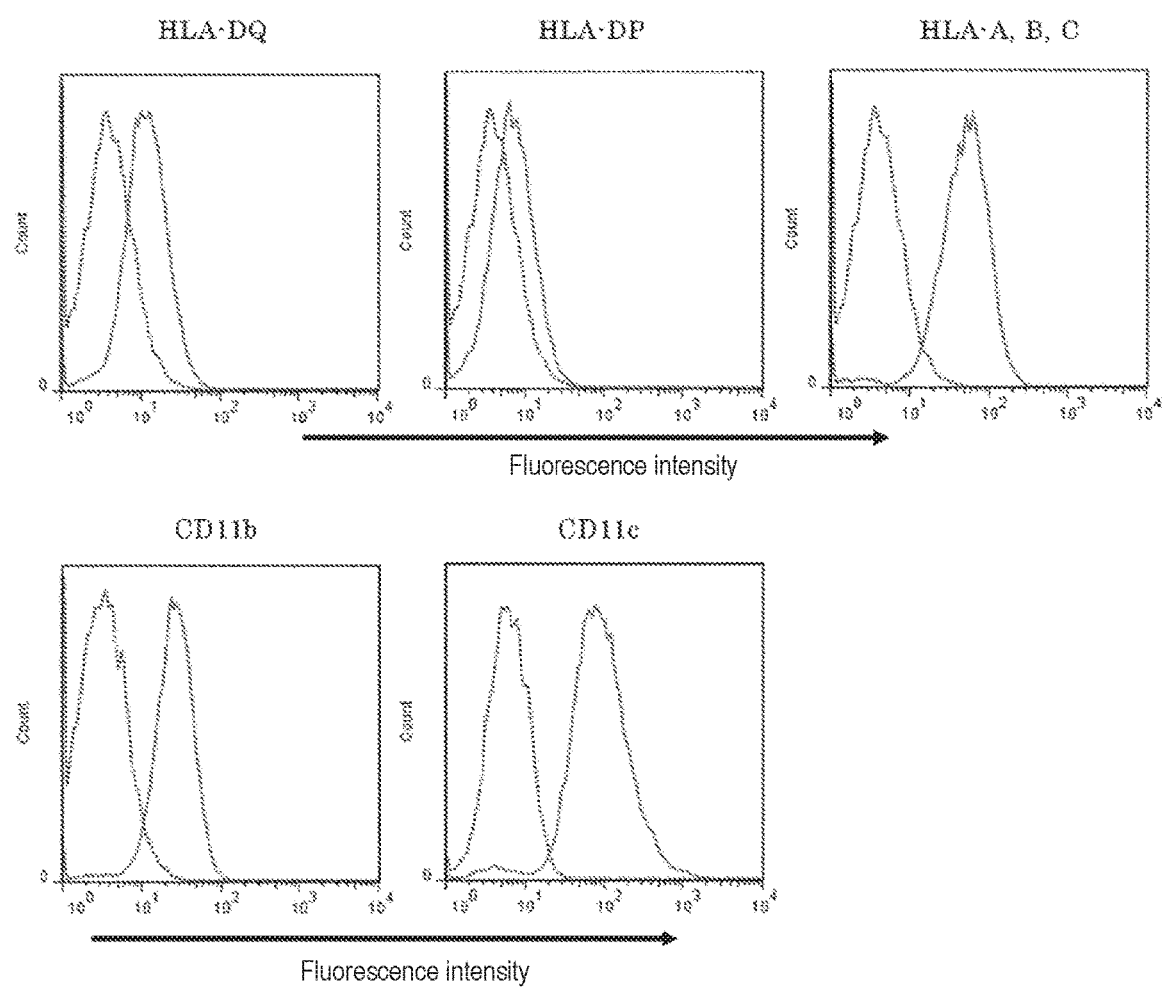
FIG. 4B shows results of examining molecules expressed on the cell surface of monocyte-like cells prepared from a 201B7 line, wherein the results were obtained by analysis using a flow cytometer.

FIGS. 4A and 4B each show results of examining molecules expressed on the cell surface of the monocyte-like cells prepared using 201B7, wherein the results were obtained by analysis using a flow cytometer. The monocyte-like cells obtained by the present Examples were found to express a monocyte-specific marker CD14 and also found to express T cell-activating molecules CD80 and CD86 and adhesion molecules CD11b and CD11c, as with the monocyte-like cells prepared using Tic.

Figure 5A:
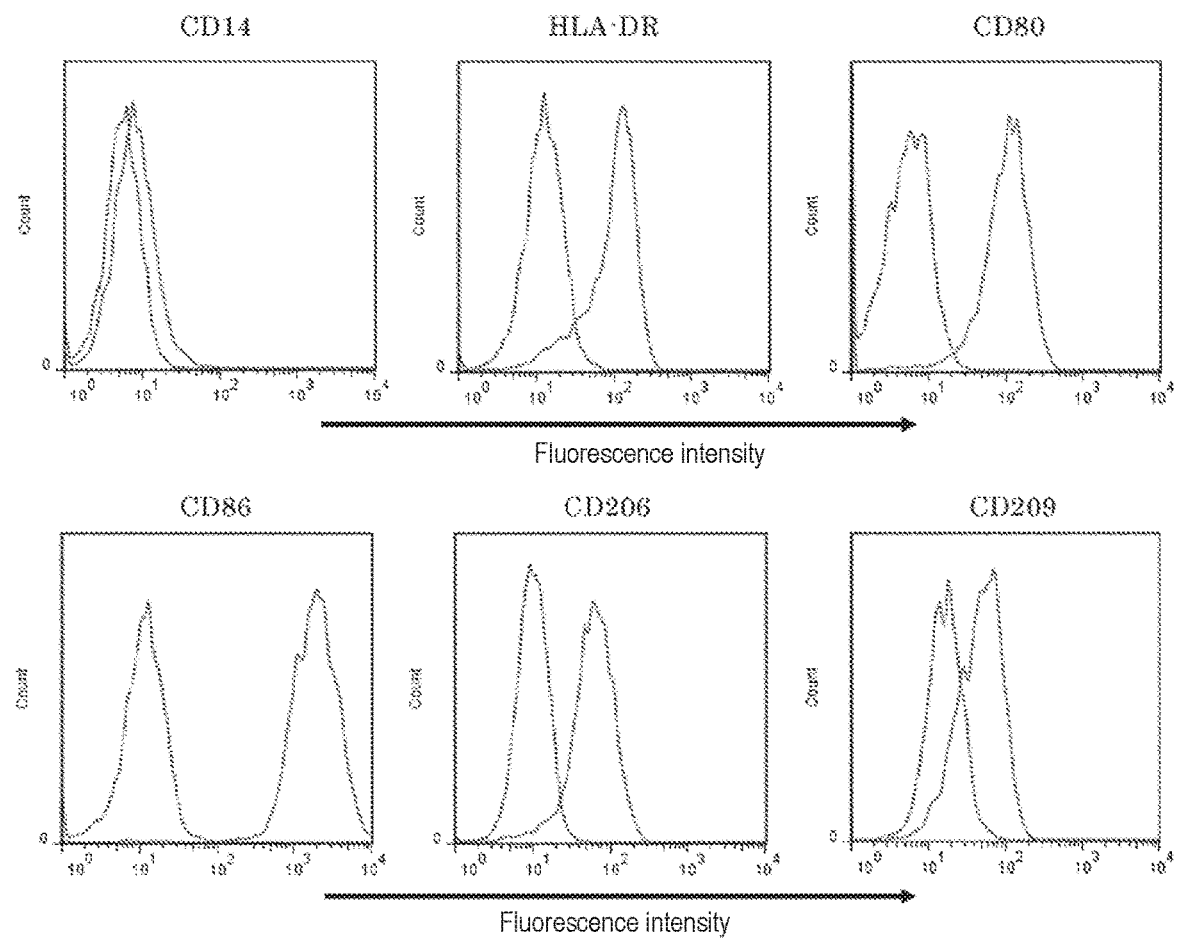
FIG. 5A shows results of examining molecules expressed on the cell surface of dendritic cell-like cells prepared from a Tic line, wherein the results were obtained by analysis using a flow cytometer.
Figure 5B:
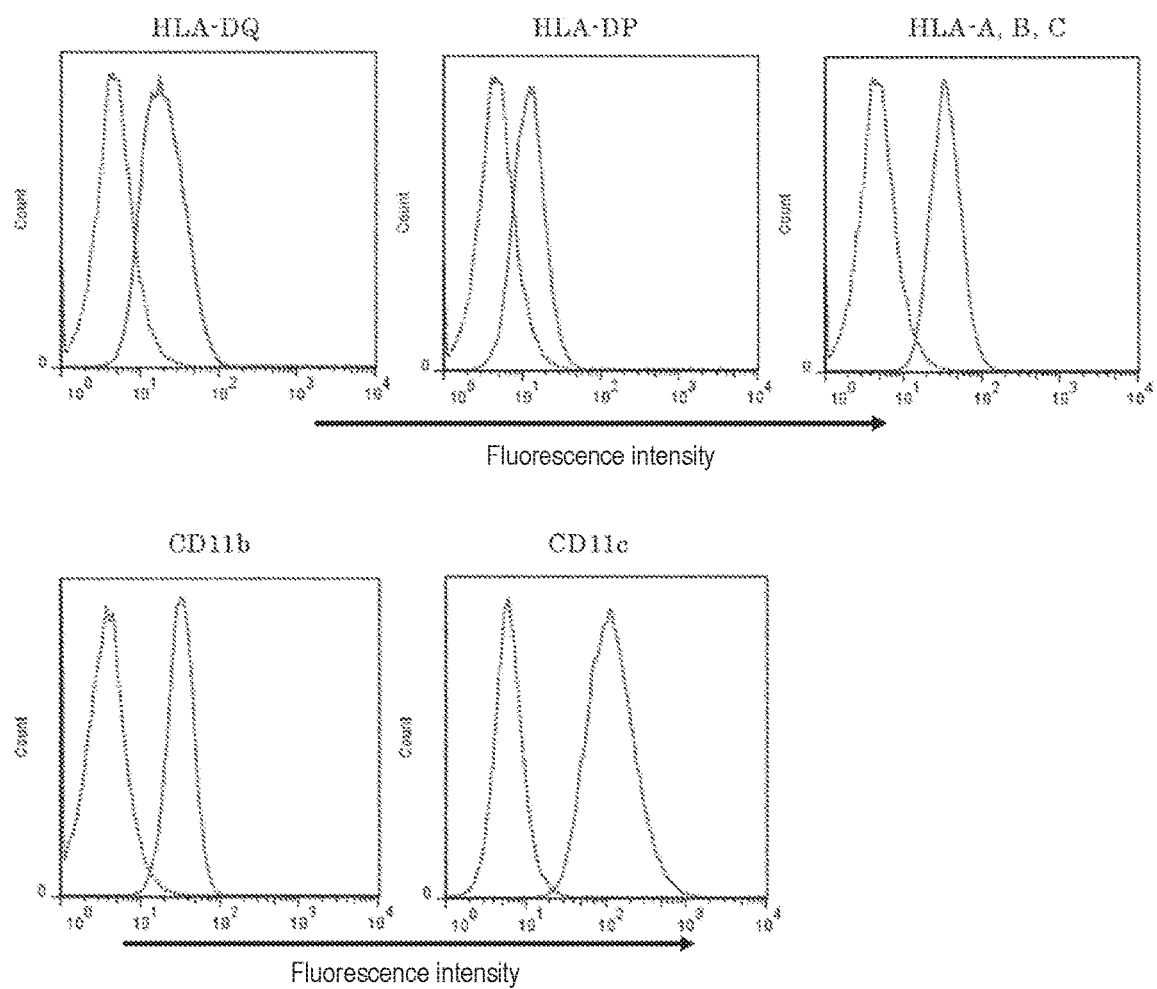
FIG. 5B shows results of examining molecules expressed on the cell surface of dendritic cell-like cells prepared from a Tic line, wherein the results were obtained by analysis using a flow cytometer.

FIGS. 5A and 5B each show results of examining molecules expressed on the cell surface of the dendritic cell-like cells prepared using Tic, wherein the results were obtained by analysis using a flow cytometer. The dendritic cell-like cells obtained by the present Examples were found to express antigen presentation molecules HLA-DR, HLA-DQ, HLA-DP, and HLA-ABC and dendritic cell-specific markers CD206 and CD209 and also found to express T cell-activating molecules CD80 and CD86 and adhesion molecules CD11b and CD11c, as with the monocyte-like cells. Increase in the expression of CD11c was found, as compared with the monocyte-like cells. On the other hand, the expression of the monocyte-specific marker CD14 was decreased. Each marker had a single peak, suggesting that cells having the features of dendritic cells were homogeneously prepared.

Figure 6A:
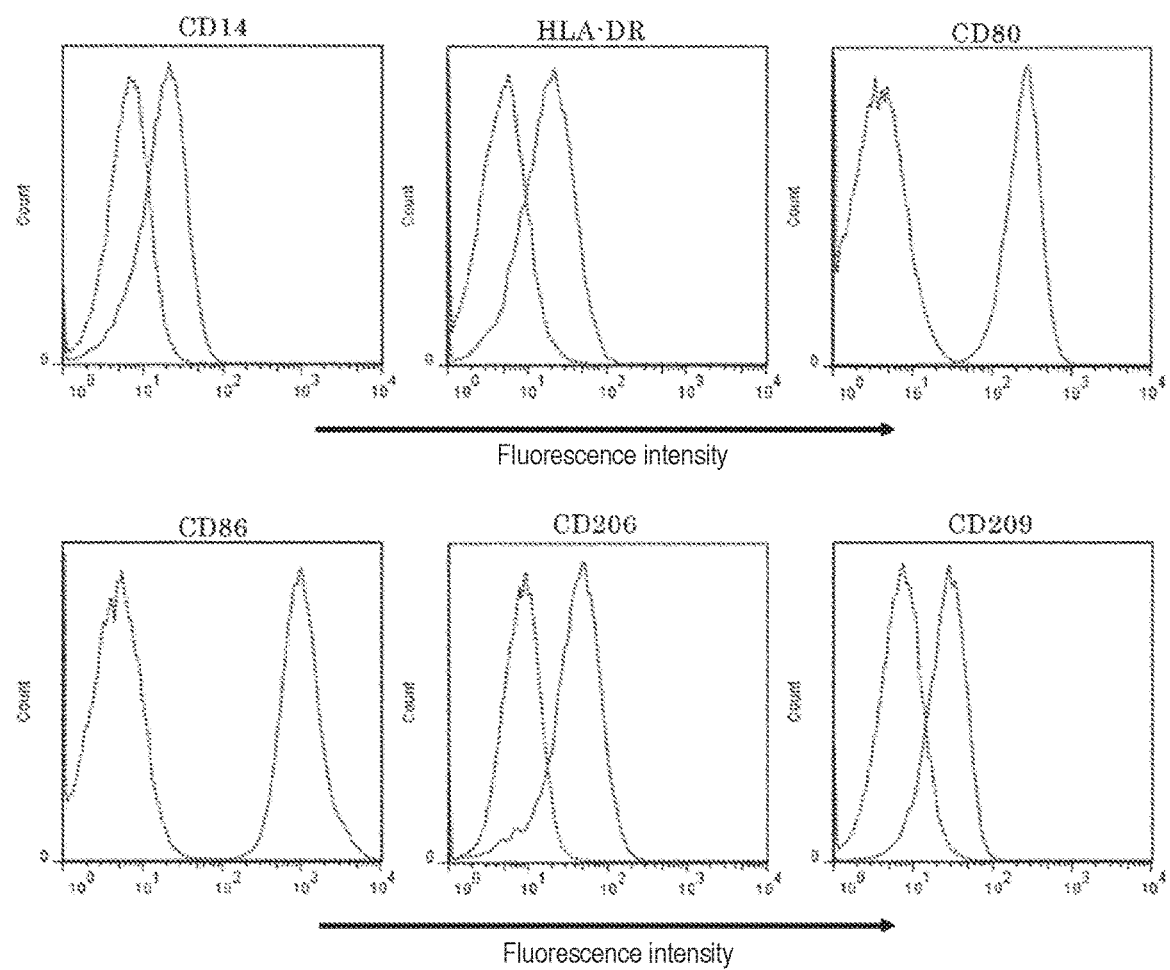
FIG. 6A shows results of examining molecules expressed on the cell surface of dendritic cell-like cells prepared from a 201B7 line, wherein the results were obtained by analysis using a flow cytometer.
Figure 6B:
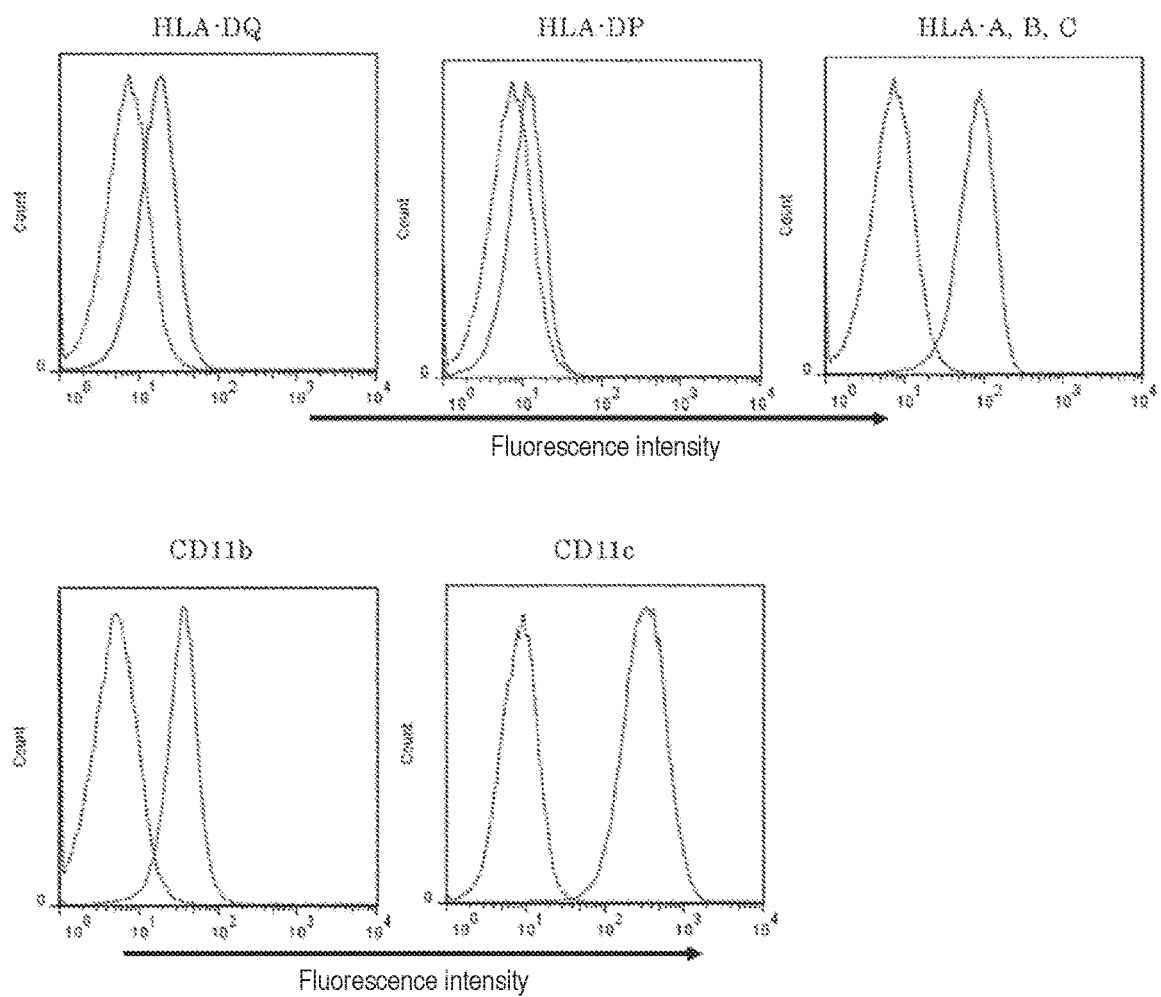
FIG. 6B shows results of examining molecules expressed on the cell surface of dendritic cell-like cells prepared from a 201B7 line, wherein the results were obtained by analysis using a flow cytometer.
Figure 10B:
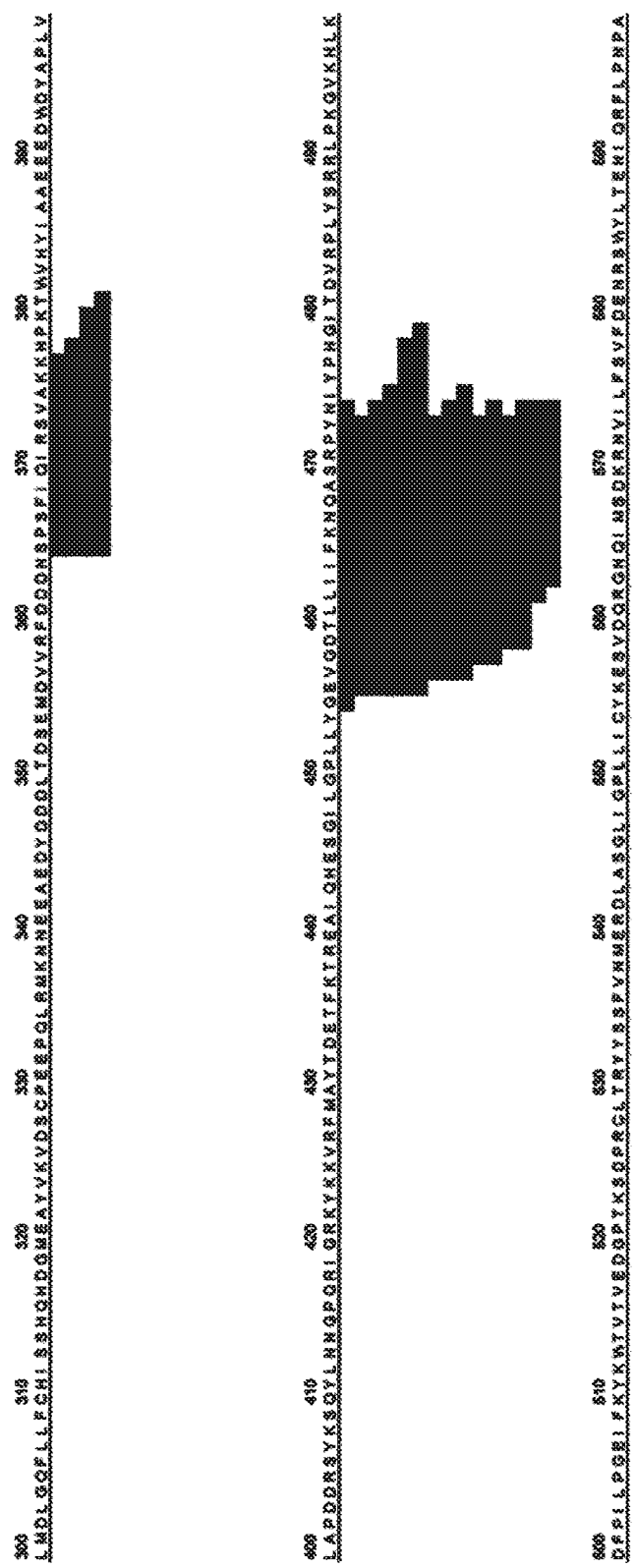
Figure 10D:
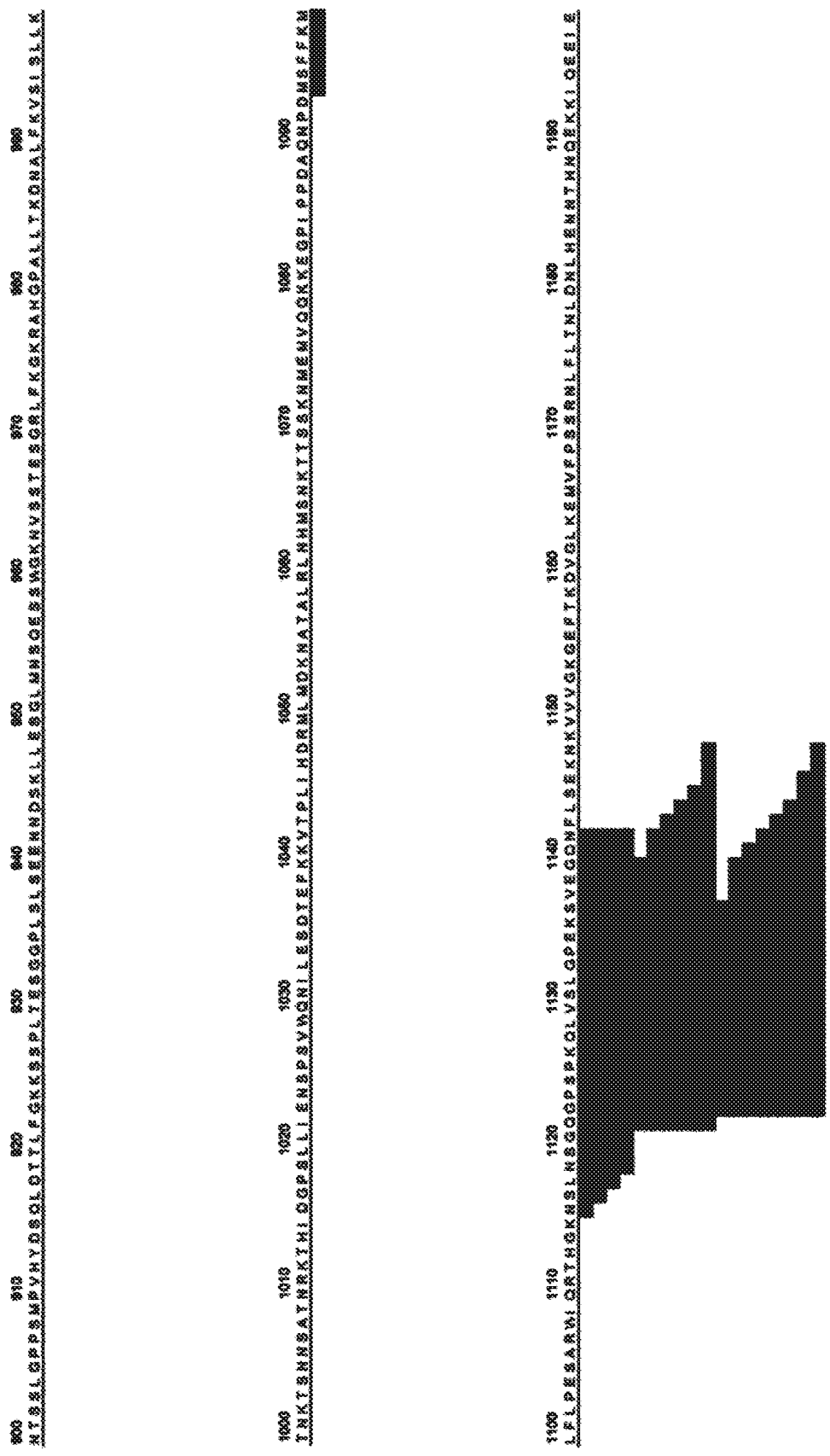
Figure 10F:
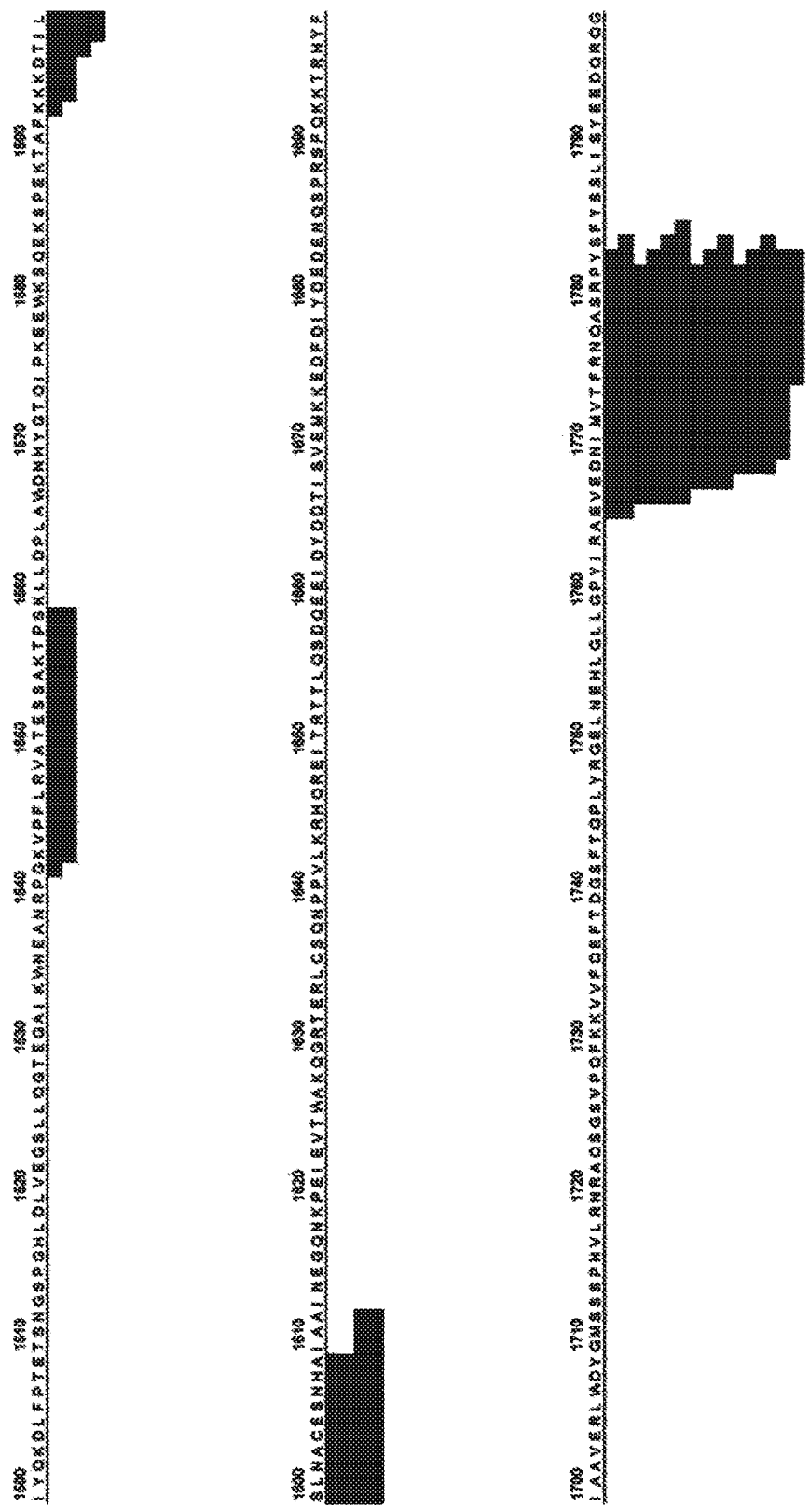
Figure 10G:
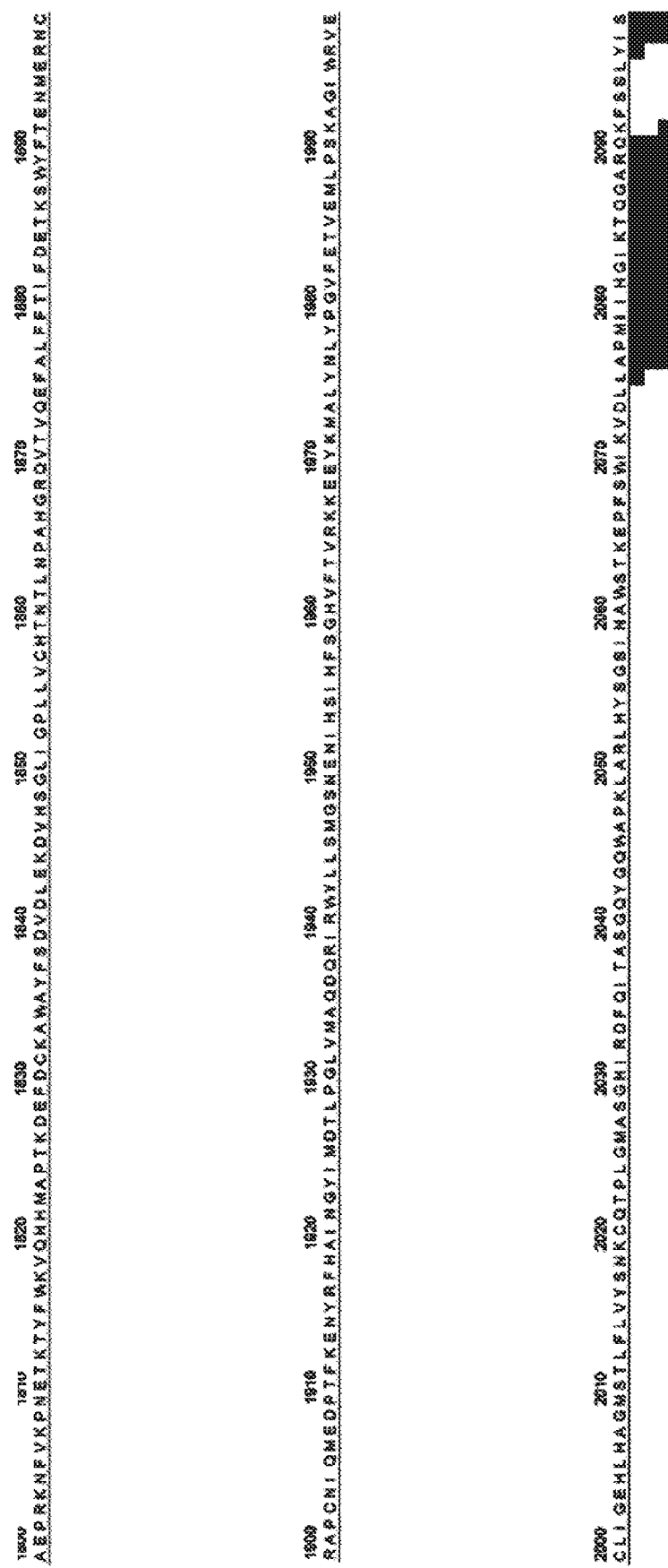
Figure 10H:
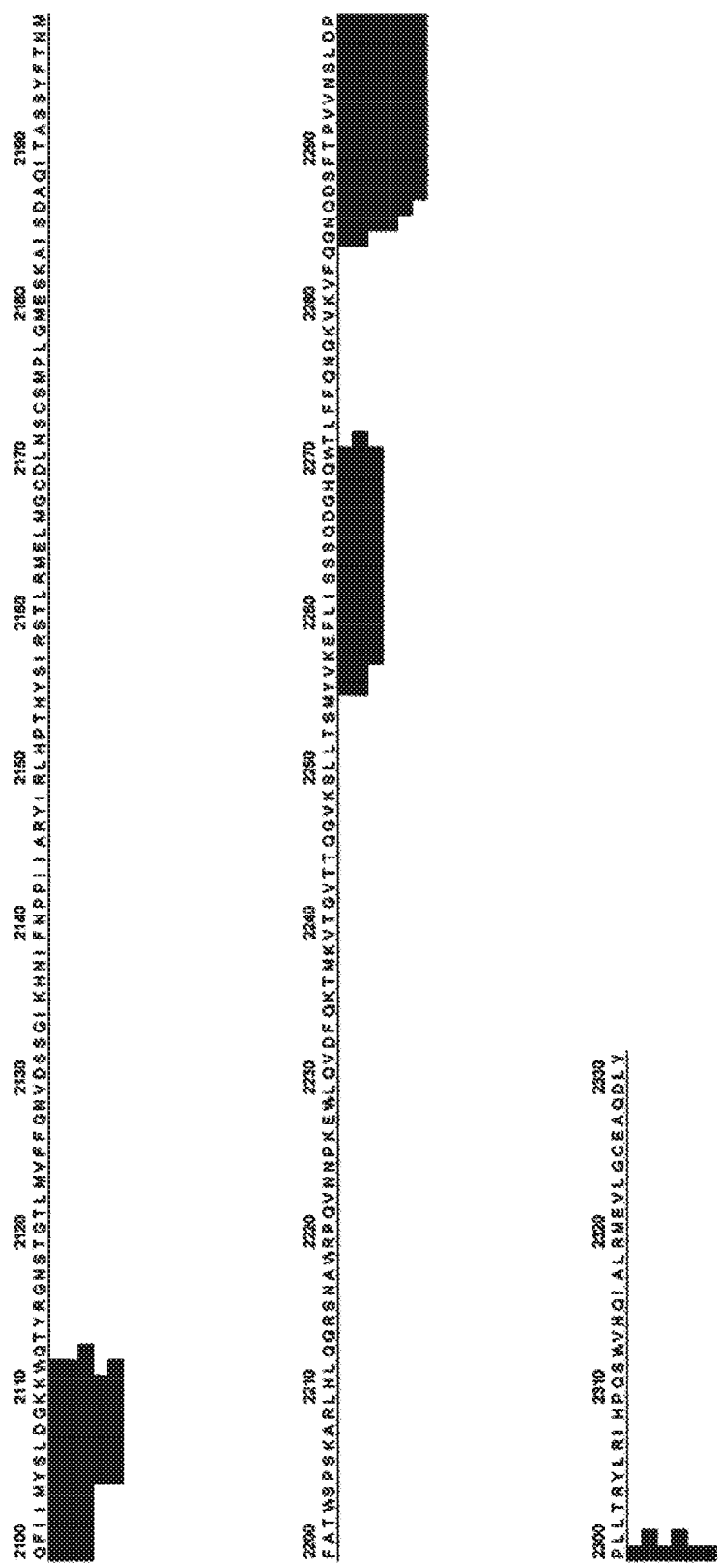

FIGS. 6A and 6B each show results of examining molecules expressed on the cell surface of the dendritic cell-like cells prepared using 201B7, wherein the results were obtained by analysis using a flow cytometer. The dendritic cell-like cells prepared from 201B7 were also found to express antigen presentation molecules HLA-DR, HLA-DQ, HLA-DP, and HLA-ABC and dendritic cell-specific markers CD206 and CD209, as with the dendritic cell-like cells prepared from Tic. These dendritic cell-like cells were also found to express T cell-activating molecules CD80 and CD86 and adhesion molecules CD11b and CD11c, as with the monocyte-like cells.

—Results Obtained Using Bet v1a—

FIG. 7A shows results of analyzing the amino acid sequences of peptides detected by the exposure of the dendritic cell-like cells prepared from Tic to Bet v1a. In the present Examples, a portion of the amino acid sequence of Bet v1a was detected from the peptides separated from HLA-DR molecules extracted from the dendritic cell-like cells exposed to Bet v1a.

FIG. 7B shows results of analyzing the amino acid sequence of peptides detected both under Bet v1a non-treatment conditions (control) and by exposure to Bet v1a.

These specific amino acid sequences thus detected are also shown in Tables 1A and 1B. In these tables, Epitope No. represents a group of detected peptides observed in order from the N terminus of the amino acid sequence of Bet v1a. For example, 18 types of peptides were detected in Epitope No. 1.

TABLE 1A

*Betula verrucosa*, birch pollen allergen 1, Isoform a (Bet v1a) epitope associated with iPS-DC (Tic line)

| Epitope No. | | Bet v1a region |
|---|---|---|
| #1 | ILDGDNLFPKVAPQAISSVENIEGNGGPGTIKK | 23-55 |
| | ILDGDNLFPKVAPQAISSVENIEGNGGPGTIK | 23-54 |
| | ILDGDNLFPKVAPQAISSVENIEGNGGPGT | 23-52 |
| | ILDGDNLFPKVAPQAISSVENIEGNGGPG | 23-51 |
| | ILDGDNLFPKVAPQAISSVENIEGNGGPGTIK | 24-54 |
| | DGDNLFPKVAPQAISSVENIEGNGGPGTIK | 25-54 |
| | LFPKVAPQAISSVENIEGNGGPGTIK | 29-54 |
| | LFPKVAPQAISSVENIEGNGGPG | 29-51 |
| | FPKVAPQAISSVENIEGNGGPGTIK | 30-54 |
| | KVAPQAISSVENIEGNGGPGTIKK | 32-55 |
| | KVAPQAISSVENIEGNGGPGTIK | 32-54 |
| | KVAPQAISSVENIEGNGGPG | 32-51 |
| | VAPQAISSVENIEGNGGPGTIK | 33-54 |

TABLE 1A-continued

*Betula verrucosa*, birch pollen allergen 1, Isoform a (Bet v1a) epitope associated with iPS-DC (Tic line)

| Epitope No. | | Bet v1a region |
|---|---|---|
| | VAPQAISSVENIEGNGGPG | 33-51 |
| | APQAISSVENIEGNGGPG | 34-51 |
| | APQAISSVENIEGNG | 34-48 |
| | APQAISSVENIEGN | 34-47 |
| | GGPGTIKKISFPEGFPFK | 48-65 |
| #2 | RVDEVDHTNFKYNY | 70-83 |
| #3 | DTLEKISNEIKIVATPDGGSILK | 93-115 |
| | KISNEIKIVATPDGGSILK | 97-115 |
| | KISNEIKIVATPDGGSIL | 97-114 |
| | KISNEIKIVATPDGGSI | 97-113 |
| | ISNEIKIVATPDGGSILK | 98-115 |
| | ISNEIKIVATPDGGSIL | 98-114 |
| | ISNEIKIVATPDGGSI | 98-113 |
| | ISNEIKIVATPDGGS | 98-112 |
| | ISNEIKIVATPDGG | 98-111 |
| | ISNEIKIVATPDG | 98-110 |
| | NEIKIVATPDGGSIL | 100-114 |
| | ATPDGGSILKISNKYHT | 106-122 |

(The peptides described in Table 1A were described in SEQ ID NOs: 6 to 36.)

TABLE 1B

| Epitope No. | | Bet v1a region |
|---|---|---|
| #4 | KEMGETLLRAVESYLLAHSDAYN | 137-159 |
| | KEMGETLLRAVESYLLAHSDA | 137-159 |
| | KEMGETLLRAVESYLLAHSD | 137-156 |
| | KEMGETLLRAVESYLLAHS | 137-155 |
| | KEMGETLLR | 137-145 |
| | EMGETLLRAVESYLLAHSDA | 138-157 |
| | EMGETLLRAVESYLLAHSD | 138-156 |
| | EMGETLLRAVESYLLAHS | 138-155 |
| | EMGETLLRAVESYLLAH | 138-154 |
| | MGETLLRAVESYLLAHSDA | 139-157 |
| | MGETLLRAVESYLLAHSD | 139-156 |
| | MGETLLRAVESYLLAHS | 139-155 |
| | MGETLLRAVESYLLAH | 139-154 |
| | GETLLRAVESYLLAH | 140-154 |
| | GETLLRAVESYLLAHSDA | 140-157 |
| | GETLLRAVESYLLAHSD | 140-156 |
| | GETLLRAVESYLLAHS | 140-155 |
| | ETLLRAVESYLLAHSDA | 141-157 |
| | ETLLRAVESYLLAHSD | 141-156 |
| | ETLLRAVESYLLAHS | 141-155 |
| | ETLLRAVESYLLAH | 141-154 |
| | AVESYLLAHS | 146-155 |

*Betula verrucosa*, birch pollen allergen 1, isoform a (Bet v1a) epitope associated with untreated iPS-DC (Tic line)

| Epitope No. | | Bet v1a region |
|---|---|---|
| #1' | LFPKVAPQAISSVENIEGNG | 29-48 |
| #2' | GPIGDTLEKISNEIKIVA | 89-106 |

(The peptides described in Table 1B were described in SEQ ID NOs: 37 to 60.)

Almost similar results were obtained by duplicate measurement, and reproducibility was obtained (second data not shown). Similar peptide sequences were also detected by performing the differentiation into dendritic cell-like cells at a different timing (changed timing of recovering non-adherent cells and adding GM-CSF and IL-4) and promoting a rise in the expression of HLA-DR, etc. (data not shown).

FIG. 8A shows results of analyzing the amino acid sequences of peptides detected by the exposure of the dendritic cell-like cells prepared from 201B7 to Bet v1a. In the present Examples, a portion of the amino acid sequence of Bet v1a was detected from the peptides separated from HLA-DR molecules extracted from the dendritic cell-like cells exposed to Bet v1a.

FIG. 8B shows results of analyzing the amino acid sequence of peptides detected both under Bet v1a non-treatment conditions (control) and by exposure to Bet v1a. These specific amino acid sequences thus detected are also shown in Tables 1C and 1D. In these tables, Epitope No. represents a group of detected peptides observed in order from the N terminus of the amino acid sequence of Bet v1a.

TABLE 1C

Betula verrucosa, birch pollen allergen 1,
Isoform a (Bet v1a)
epitope associated with iPS-DC (201B7 line)

| Epitope No. | | Bet v1a region |
|---|---|---|
| #1 | RLFKAFILDGDNLFPK | 17-32 |
| | LFKAFILDGDNLFPK | 18-32 |
| | LFKAFILDGDNLFPKV | 18-33 |
| | LFKAFILDGDNLFPKVA | 18-34 |
| | LFKAFILDGDNLFPKVAP | 18-35 |
| | LFKAFILDGDNLFPKVAPQ | 18-36 |
| | LFKAFILDGDNLFPKVAPQA | 18-37 |
| | LFKAFILDGDNLFPKVAPQAISSVEN | 18-43 |
| | LFKAFILDGDNLFPKVAPQAISSVENIEGN | 18-47 |
| | FKAFILDGDNLFPK | 19-32 |
| | KAFILDGDNLFPK | 20-32 |
| | KAFILDGDNLFPKVAPQ | 20-36 |
| | AFILDGDNLFPK | 21-32 |
| #2 | GGSILKISNKYHTKGD | 110-125 |
| | GGSILKISNKYHTKGDHE | 110-127 |
| | GSILKISNKYHTKG | 111-124 |
| #3 | KEMGETLLRAVESYLLAHSDA | 137-157 |
| | GETLLRAVESYLLAH | 140-154 |

(The peptides described in Table 1C were described in SEQ ID NOs: 114 to 131.)

TABLE 1D

Betula verrucosa, birch pollen allergen 1,
Isoform a (Bet v1a) epitope associated with
untreated iPS-DC (201B7 line)

| Epitope No. | | Bet v1a region 1 |
|---|---|---|
| #1 | VAPQAISSVENIEGNGGPG | 33-51 |

(The peptide described in Table 1D was described in SEQ ID NO: 132.)

Almost similar results were obtained by duplicate measurement, and reproducibility was obtained (second data not shown).

—Results Obtained Using Infliximab—

FIG. 9A shows results of analyzing the amino acid sequences of peptides detected by the exposure of the dendritic cell-like cells prepared from Tic to infliximab. In the present Examples, a portion of the amino acid sequences found in the H and L chains of infliximab was detected from the peptides separated from HLA-DR molecules extracted from the dendritic cell-like cells exposed to infliximab.
(The peptides described in FIG. 9A were described in SEQ ID NOs: 133 to 151.)

FIG. 9B shows results of analyzing the amino acid sequence of peptides detected both under infliximab non-treatment conditions (control) and by exposure to infliximab. Only a portion of the amino acid sequence found in the H chain of infliximab was detected.
(The peptides described in FIG. 9B were described in SEQ ID NOs: 152 and 153.)

Almost similar results were obtained by duplicate measurement, and reproducibility was obtained (second data not shown). Similar peptide sequences were also detected by performing the differentiation into dendritic cell-like cells at a different timing (changed timing of recovering non-adherent cells and adding GM-CSF and IL-4) and promoting a rise in the expression of HLA-DR, etc. (data not shown).

—Results Obtained Using rhFVIII—

FIGS. 10A to 10H each show results of analyzing the amino acid sequences of peptides detected by the exposure of the dendritic cell-like cells prepared from Tic to rhFVIII. In the present Examples, a portion of the amino acid sequence of rhFVIII was detected from the peptides separated from HLA-DR molecules extracted from the dendritic cell-like cells exposed to rhFVIII.
(The peptides described in FIGS. 10A to 10H were described in SEQ ID NOs: 154 to 250.)

Almost similar results were obtained by duplicate measurement, and reproducibility was obtained (second data not shown).

Results Obtained Using Phl p1—

FIG. 11 shows results of analyzing the amino acid sequences of peptides detected by the exposure of the dendritic cell-like cells prepared from Tic to Phl p1. In the present Examples, a portion of the amino acid sequence of Phl p1 was detected.
(The peptides described in FIG. 11 were described in SEQ ID NOs: 251 to 253.)

Almost similar results were obtained by duplicate measurement, and reproducibility was obtained (second data not shown). Similar peptide sequences were also detected by starting the differentiation of human iPS cells into monocyte-like cells at a different timing, recovering non-adherent cells, performing the differentiation into dendritic cell-like cells, and promoting a rise in the expression of HLA-DR, etc. (data not shown).

In the aforementioned methods, the peptides presented on the HLA-DR molecules of the dendritic cell-like cells exposed to each antigen were separated and purified as HLA-DR-peptide complexes by use of the anti-HLA-DR beads, and the sequence of each presented peptide was identified by ion trap MS/MS mass spectrometry. Here, as is evident from, for example, FIGS. 3B, 4B, and 5B, the antigen-presenting cells such as monocyte-like cells or dendritic cell-like cells were confirmed to express HLA-DQ molecules, HLA-DP molecules, HLA-A molecules, HLA-B molecules, and HLA-C molecules. Thus, those skilled in the art can understand that, similarly, antigen-presented peptides can also be detected and identified by using, instead of the HLA-DR molecules, other MHC II molecules (e.g., HLA-DQ and HLA-DP molecules), or MHC I molecules.

For example, Karbach J, Pauligk C, Bender A, Gnjatic S, Franzmann K, Wahle C, Jager D, Knuth A, Old L J, Jager E., Identification of new NY-ESO-1 epitopes recognized by CD4+ T cells and presented by HLA-DQ B1 03011, Int J Cancer. 2006 Feb. 1; 118 (3): 668-74 discloses that antigen-specific T cells were prepared using dendritic cells allowed to present NY-ESO-1, a cancer antigen, and restimulated with an EBV-B cell line expressing HLA-DQ molecules allowed to present the same antigen as above, whereby peptide sequences in NY-ESO-1 presented by the HLA-DQ molecules were able to be detected. This literature also discloses that antigen-presented T cell epitopes can be identified using HLA-DQ molecules. For example, Duquesnoy R J, Marrari M, Tambur A R, Mulder A, Sousa L C, da Silva A S, do Monte S J, First report on the antibody verification of HLA-DR, HLA-DQ and HLA-DP epitopes recorded in the HLA Epitope Registry, Hum Immunol. 2014 November; 75 (11): 1097-103 discloses that sequences more likely to be presented by HLA-DR, HLA-DQ, and HLA-DP molecules were predicted from a database, and the HLA-DQ and HLA-DP molecules antigen-present particular sequences, as with the HLA-DR molecules. On the basis of such technical common sense, those skilled in the art will understand that MAPPs can also be applied to cells expressing other MHC II molecules such as HLA-DQ and HLA-DP molecules, which have been differentiated from a stem cell or a progenitor cell derived therefrom according to the present invention. Also, MAPPs using MHC I molecules have already been reported in, for example, Wahl A, Schafer F, Bardet W, Buchli R, Air G M, Hildebrand W H., HLA class I molecules consistently present internal influenza epitopes. Proc Natl Acad Sci USA. 2009 Jan. 13; 106 (2): 540-5. In this literature, cell lines allowed to express particular HLA-B molecule allotypes were sensitized with influenza virus, and influenza virus-derived peptide sequences presented on the HLA-B molecules were detected by MAPPs. As mentioned above, MHC I molecules are known to be expressed by many cell lines. Hence, it is desirable to utilize cells highly expressing MHC I molecules, from the viewpoint of the easy detection of MHC I molecule-peptide complexes. In one embodiment, a dendritic cell differentiated from a stem cell or a progenitor cell derived therefrom according to the present invention may be used in MAPPs using MHC I molecules.

Comparative Examples

A. Method
—Cells Used—
Human peripheral blood mononuclear cells (PBMCs): (purchased from Lonza Co., Ltd.).
—Separation of Monocytes from Human Peripheral Blood Mononuclear Cells—
1. 80 µL/$10^7$ cells of DPBS (Invitrogen Corp., Cat: 14190) supplemented with 0.5% Human Serum Albumin low IgG (Sigma-Aldrich Corp., Cat.: A3782) and 2 mM EDTA 0.5 M stock solution pH 8.0 (Invitrogen Corp., Cat.: 15575) and 20 µL/$10^7$ cells of CD14 micro beads (Miltenyi Biotec K.K., Cat.: 130-050-201) were added to human peripheral blood mononuclear cells, which were then suspended with a vortex mixer and left standing at 4° C. for 15 minutes under light shielding conditions.
2. 20 mL of DPBS containing 0.5% Human Serum Albumin low IgG and 2 mM EDTA 0.5 M stock solution pH 8.0 was added to the human peripheral blood mononuclear cells thus left standing for 15 minutes, and spun down at 1200 rpm at 4° C. for 5 minutes, followed by the removal of the whole supernatant. This operation was performed two times.
3. DPBS containing 0.5% Human Serum Albumin low IgG and 2 mM EDTA 0.5 M stock solution pH 8.0 was added at $1.2 \times 10^8$ cells/mL to the human peripheral blood mononuclear cells thus rendered free from the supernatant, and the human peripheral blood mononuclear cells recovered by passing through a magnet LS Column for cell separation (Miltenyi Biotec K.K., Cat.: 130-042-401) were used as monocytes.
—Antigens Used—
*Betula verrucosa*, birch pollen allergen 1, Isoform a (Bet v1a) (# Bet v 1.0101; Biomay AG) (amino acid sequence: SEQ ID NO: 1) as a white birch pollen allergen was used in the same way as in Examples of the present invention.
—Differentiation into Dendritic Cells and Exposure to Antigen—
1. 20 mL of DPBS containing 0.5% Human Serum Albumin low IgG and 2 mM EDTA 0.5 M stock solution pH 8.0 was added to the recovered monocytes and spun down at 1200 rpm at 4° C. for 5 minutes, followed by the removal of the whole supernatant.
2. The monocytes thus rendered free from the supernatant were suspended at a cell density of $3 \times 10^5$ cells/mL using RPMI 1640 (Life Technologies/Thermo Fisher Scientific Inc., Cat.: 11875) supplemented with 10% fetal bovine serum (FBS) (Gibco, Cat.: 10270, 26140), 1% non-essential amino acids (Gibco, Cat.: 11140-035), 1% Na-pyruvate (Gibco, Cat.: 11360-039), 1% kanamycin (Gibco, Cat.: 15160-047), 50 ng/mL recombinant human Granulocyte Macrophage colony-stimulating factor (rhGM-CSF) (R&D Systems, Inc., Cat.: 215-GM), and 3 ng/mL recombinant human Interleukin-4 (rhIL-4) (R&D Systems, Inc., Cat.: 204-IL), and inoculated in an amount of 3 mL/well to a 6-well plate, followed by culture at 37° C. for 5 days under 5% CO2 conditions. The monocytes thus cultured for 5 days were used as dendritic cells.
3. After the 5-day culture, 2 mL/well of the supernatant was removed from each well, and 3.3 µg/mL Bet v1a and subsequently 1 µg/mL Lipopolysaccharides from *Salmonella enterica* serotype abortusequi (LPS) (Sigma-Aldrich Corp., Cat.: L5886) were added to each well, followed by culture at 37° C. for 1 day under 5% $CO_2$ conditions.
4. The whole amount of the dendritic cells thus cultured for 1 day was recovered from the 6-well plate and spun down at 1200 rpm at 4° C. for 5 minutes. Then, the whole supernatant was removed, and the cells were suspended in 1 mL of DPBS of 4° C. Subsequently, the whole amount thereof was transferred to an Eppendorf tube, and spun down at 2500 rpm at 4° C. for 5 minutes. The whole supernatant was removed, and a pellet of the cells was prepared and stored at −80° C.
5. A portion of the dendritic cells was recovered, stained with an anti-human HLA-DR antibody, an anti-human HLA-DQ antibody, an anti-human HLA-DP antibody, an anti-human HLA-ABC antibody, an anti-human CD14 antibody, an anti-human CD80 antibody, an anti-human CD86 antibody, an anti-human CD206 antibody, an anti-human CD209 antibody, an anti-human CD11b antibody, and an anti-human CD11c antibody, and analyzed using a flow cytometry apparatus BD FACSCanto™ II.
—Formation of Anti-HLA-DR Beads—
This operation was performed in the same way as in Examples of the present invention.
—Nanoscale Purification of HLA-DR-Peptide Complex—
This operation was performed in the same way as in Examples of the present invention.
—Elution of HLA-DR-Related Peptide—
This operation was performed in the same way as in Examples of the present invention.
—Sequence Analysis of Peptide by Ion Tap MS/MS Mass Spectrometry—
This operation was performed in the same way as in Examples of the present invention.

B. Results

—Properties of Differentiated Cells—

Figure 12:
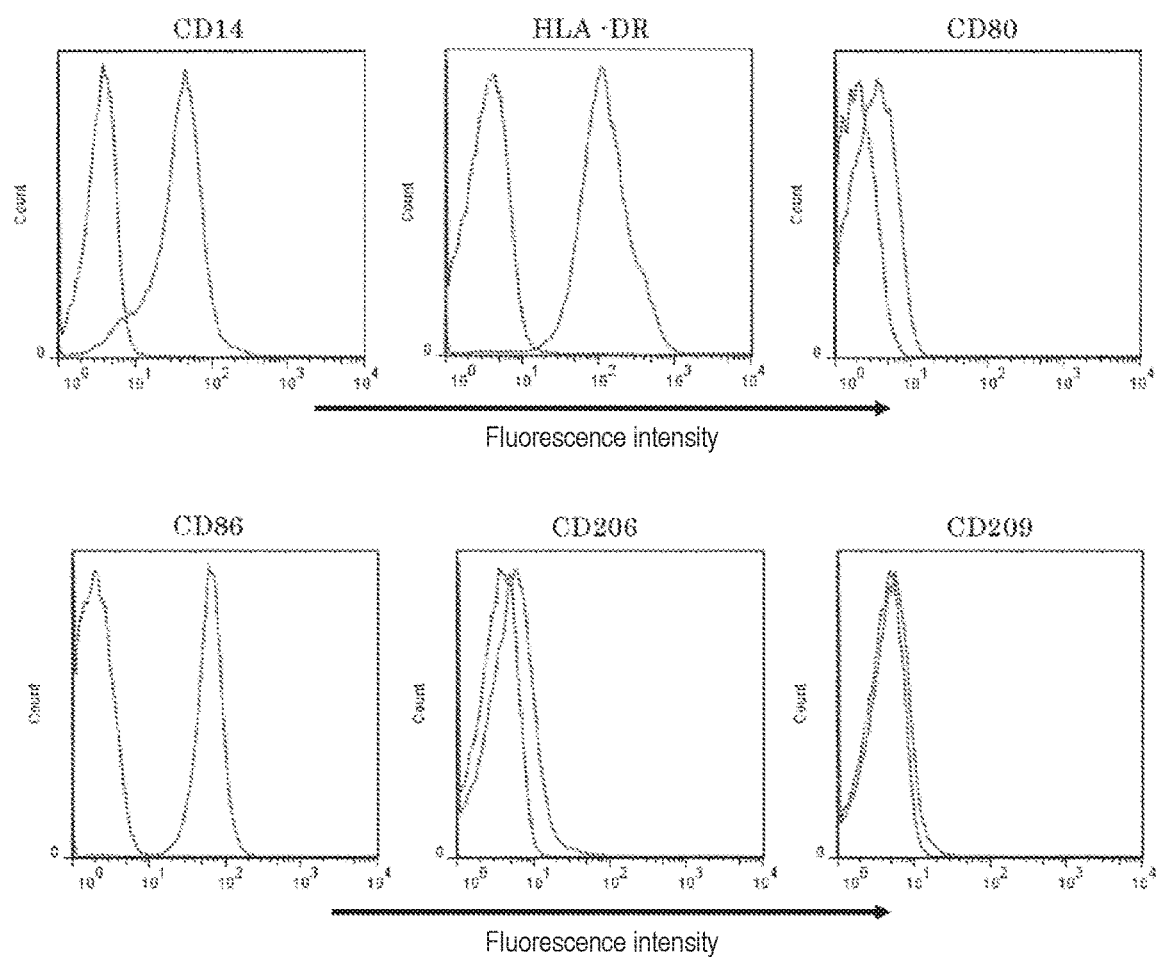
FIG. 12 shows results of examining molecules expressed on the cell surface of monocytes, wherein the results were obtained by analysis using a flow cytometer.

FIG. 12 shows results of examining molecules expressed on the cell surface of the monocytes, wherein the results were obtained by analysis using a flow cytometer. The monocytes obtained by Comparative Examples were found to express a monocyte-specific marker CD14 and an antigen presentation molecule HLA-DR and also found to express a T cell-activating molecule CD86.

Figure 13A:
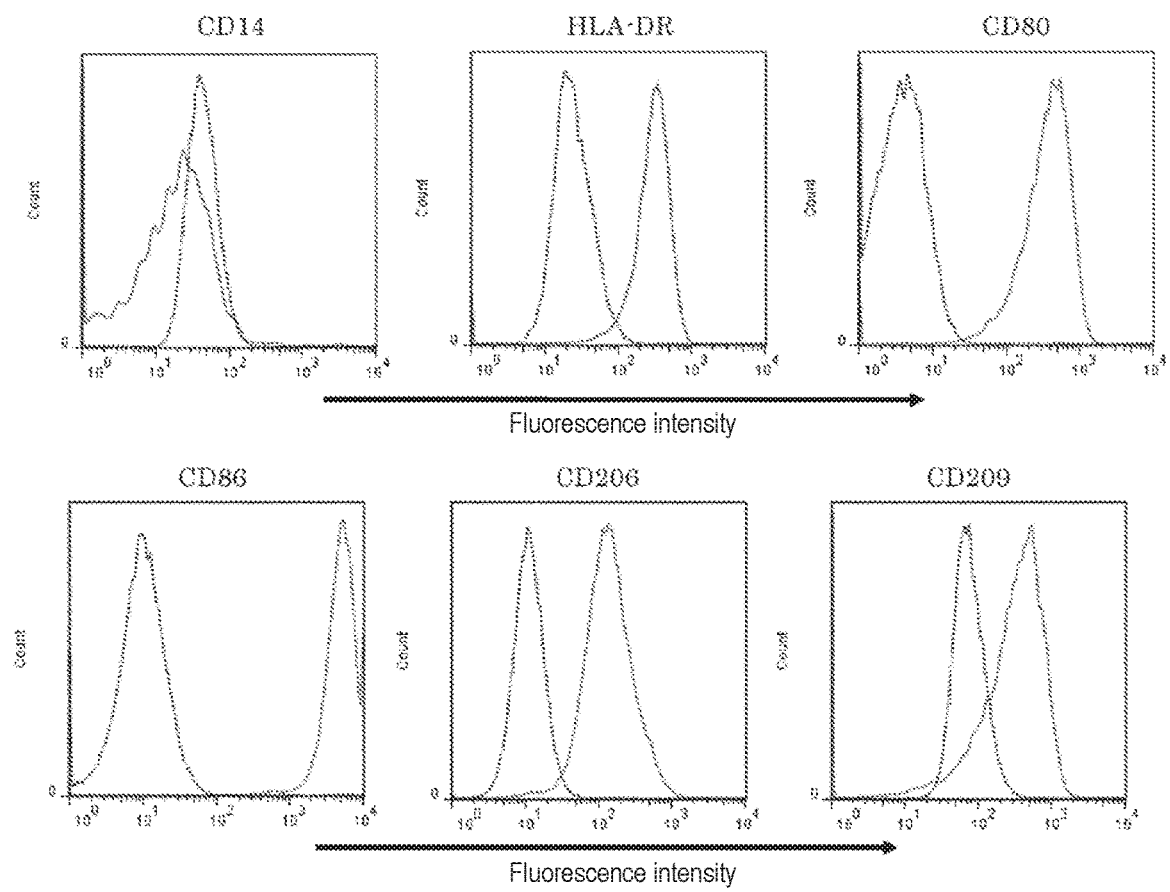
FIG. 13A shows results of examining molecules expressed on the cell surface of dendritic cells, wherein the results were obtained by analysis using a flow cytometer.
Figure 13B:
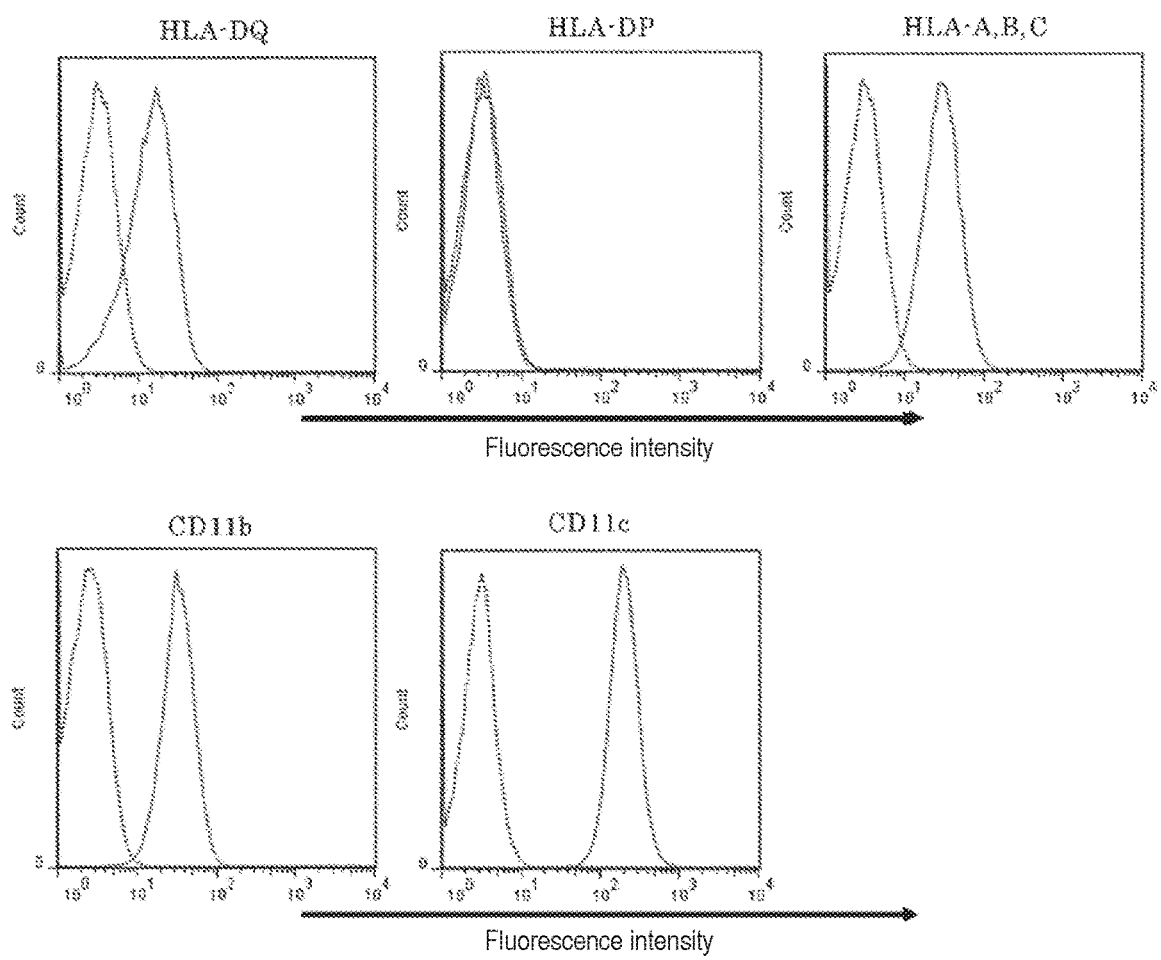
FIG. 13B shows results of examining molecules expressed on the cell surface of dendritic cells, wherein the results were obtained by analysis using a flow cytometer.

FIGS. 13A and 13B each show results of examining molecules expressed on the cell surface of the dendritic cells, wherein the results were obtained by analysis using a flow cytometer. The dendritic cells obtained by Comparative Examples were found to express antigen presentation molecules HLA-DR, HLA-DQ, and HLA-ABC and dendritic cell-specific markers CD206 and CD209 and also found to express T cell-activating molecules CD80 and CD86 and adhesion molecules CD11b and CD11c. On the other hand, the expression of CD14 was not observed.

—Results Obtained Using Bet v1a—

FIGS. 14A to 20B each show results of analyzing the amino acid sequences of peptides detected under Bet v1a addition conditions (FIGS. 14A, 15A, 16A, 17A, 18A, 19A, and 20A) or non-addition conditions (control) (FIGS. 14B, 15B, 16B, 17B, 18B, 19B, and 20B) for each human donor subjected to the evaluation. These specific amino acid sequences thus detected are also shown in Tables 2 to 8 (which correspond to FIGS. 14A and 14B to FIGS. 20A and 20B, respectively). In these tables, Epitope No. represents a group of detected peptides observed in order from the N terminus of the amino acid sequence of Bet v1a.

TABLE 2

*Betula verrucosa*, birch pollen allergen 1, Isoform a (Bet v1a) epitope associated with donor 484¶

| Epitope No.¶ | | Bet v1a region 1 |
|---|---|---|
| #1 | EVDHTNFKYNYSVIEGGPIG | 73-92 |
| | EVDHTNFKYNYSVIEGGPI | 73-91 |
| #2 | TPDGGSILKISNKYHTKGDHE | 107-127 |

(The peptides described in Table 2 were described in SEQ ID NOs: 61 to 63.)

TABLE 3

*Betula verrucosa*, birch pollen allergen 1, Isoform a (Bet v1a) epitope associated with donor 554¶

| Epitope No.¶ | | Bet v1a region 1 |
|---|---|---|
| #3 | LFKAFILDGDNLFPKVAPQA | 18-37 |
| | LFKAFILDGDNLFPKVAPQ | 18-36 |
| | LFKAFILDGDNLFPK | 18-32 |
| | LFKAFILDGDNLFP | 18-31 |
| | FKAFILDGDNLFPK | 19-32 |
| #2 | TPDGGSILKISNKYHTKGDHE | 107-127 |

TABLE 3-continued

*Betula verrucosa*, birch pollen allergen 1, Isoform a (Bet v1a) epitope associated with untreated donor 554¶

| Epitope No.¶ | | Bet v1a region 1 |
|---|---|---|
| #1' | LEKISNEIKIVATPDGGSI | 95-113 |

(The peptides described in Table 3 were described in SEQ ID NOs: 64 to 70.)

TABLE 4

*Betula verrucosa*, birch pollen allergen 1, Isoform a (Bet v1a) epitope associated with donor 558¶

| Epitope No.¶ | | Bet v1a region 1 |
|---|---|---|
| #4 | LFPKVAPQAISSVENIEGNG | 29-48 |
| | APQAISSVENIEGNGGPG | 34-51 |

*Betula verrucosa*, birch pollen allergen 1, Isoform a (Bet v1a) epitope associated with untreated donor 558¶

| Epitope No.¶ | | Bet v1a region 1 |
|---|---|---|
| #2' | LFPKVAPQAISSVENIEGNG | 29-48 |

(The peptides described in Table 4 were described in SEQ ID NOs: 71 to 73.)

TABLE 5

*Betula verrucosa*, birch pollen allergen 1, Isoform a (Bet v1a) epitope associated with donor 560¶

| Epitope No.¶ | | Bet v1a region 1 |
|---|---|---|
| #3 | LFKAFILDGDNLFPKVAPQA | 18-37 |
| | LFKAFILDGDNLFPKVAPQ | 18-36 |
| | LFKAFILDGDNLFPK | 18-32 |
| | LFKAFILDGDNLFP | 18-31 |
| #1 | EVDHTNFKYNYSVIEGGPIG | 73-92 |
| #2 | TPDGGSILKISNKYHTKGDHE | 107-127 |

(The peptides described in Table 5 were described in SEQ ID NOs: 74 to 79.)

TABLE 6

*Betula verrucosa*, birch pollen allergen 1, Isoform a (Bet v1a) epitope associated with donor 562¶

| Epitope No.¶ | | Bet v1a region 1 |
|---|---|---|
| #5 | ENIEGNGGPGTIKKISFPEGF | 42-62 |
| #1 | DRVDEVDHTNFKYNYSVIEGGPIG | 69-92 |
| | EVDHTNFKYNYSVIEGGPIG | 73-92 |
| #2 | TPDGGSILKISNKYHTKGDHE | 107-127 |
| | GGSILKISNKYHTKGDHE | 110-127 |

TABLE 6-continued

Betula verrucosa, birch pollen allergen 1, Isoform a (Bet v1a) epitope associated with donor 562

| Epitope No. | | Bet v1a region 1 |
|---|---|---|
| #6 | VSASKEMGETLLRAVESYLLAHSDAYN | 133-159 |
| | VSASKEMGETLLRAVESYLLAHSDA | 133-157 |
| | ASKEMGETLLRAVESYLLAHSDA | 135-157 |
| | EMGETLLRAVESYLLAHSDA | 138-157 |
| | EMGETLLRAVESYLLAHSD | 138-156 |
| | GETLLRAVESYLLAHSDA | 140-157 |
| | GETLLRAVESYLLAHSD | 140-156 |
| | GETLLRAVESYLLAHS | 140-155 |

(The peptides described in Table 6 were described in SEQ ID NOs: 80 to 92.)

TABLE 7

Betula verrucosa, birch pollen allergen 1, Isoform a (Bet v1a) epitope associated with donor 565

| Epitope No. | | Bet v1a region 1 |
|---|---|---|
| #6 | EMGETLLRAVESYLLAHS | 138-155 |
| | GETLLRAVESYLLAHS | 140-155 |

Betula verrucosa, birch pollen allergen 1, Isoform a (Bet v1a) epitope associated with untreated donor 565

| Epitope No. | | Bet v1a region 1 |
|---|---|---|
| #3 | PEGFPFKYVKDRVDE | 59-73 |

(The peptides described in Table 7 were described in SEQ ID NOs: 93 to 95.)

TABLE 8

Betula verrucosa, birch pollen allergen 1, Isoform a (Bet v1a) epitope associated with donor 566

| Epitope No. | | Bet v1a region 1 |
|---|---|---|
| #5 | NIEGNGGPGTIKKISFPEGFP | 43-63 |
| #6 | VKASKEMGETLLRAVESYLLAHSDAYN | 133-159 |
| | VKASKEMGETLLRAVESYLLAHSDA | 133-157 |
| | ASKEMGETLLRAVESYLLAHSDA | 135-157 |
| | KEMGETLLRAVESYLLAHSDA | 137-157 |
| | EMGETLLRAVESYLLAHSDA | 138-157 |
| | EMGETLLRAVESYLLAHSD | 138-156 |
| | MGETLLRAVESYLLAHSDA | 139-157 |
| | MGETLLRAVESYLLAHSD | 139-156 |
| | GETLLRAVESYLLAHSDA | 140-157 |
| | GETLLRAVESYLLAHSD | 140-156 |
| | GETLLRAVESYLLAHSDAYN | 140-155 |
| | GETLLRAVESYLLAH | 140-154 |
| | ETLLRAVESYLLAHSDA | 141-157 |
| | ETLLRAVESYLLAHSD | 141-156 |
| | ETLLRAVESYLLAHS | 141-155 |

(The peptides described in Table 8 were described in SEQ ID NOs: 96 to 111.)

Some of the peptides detected under the Bet v1a addition conditions were detected from the peptides detected under the Bet v1a non-addition conditions (control). However, more peptides were detected under the Bet v1a addition conditions than under the Bet v1a non-addition conditions.

—Comparison Between MAPPs Using Human iPS Cell-Derived Dendritic Cell-Like Cells and MAPPs Using PBMC-Derived Dendritic Cells—

Figure 21A:
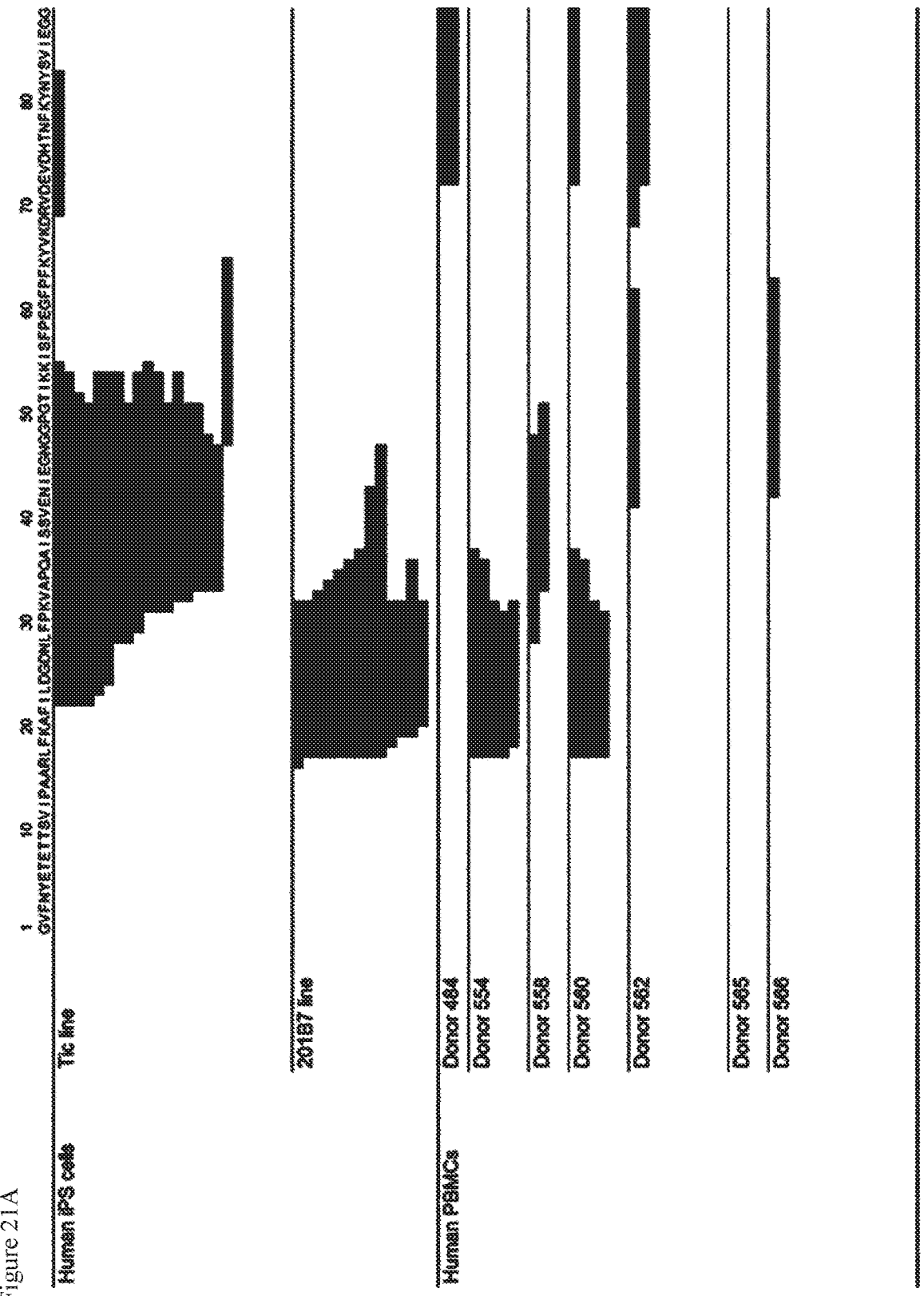
FIGS. 21A-21B.
Figure 21B:
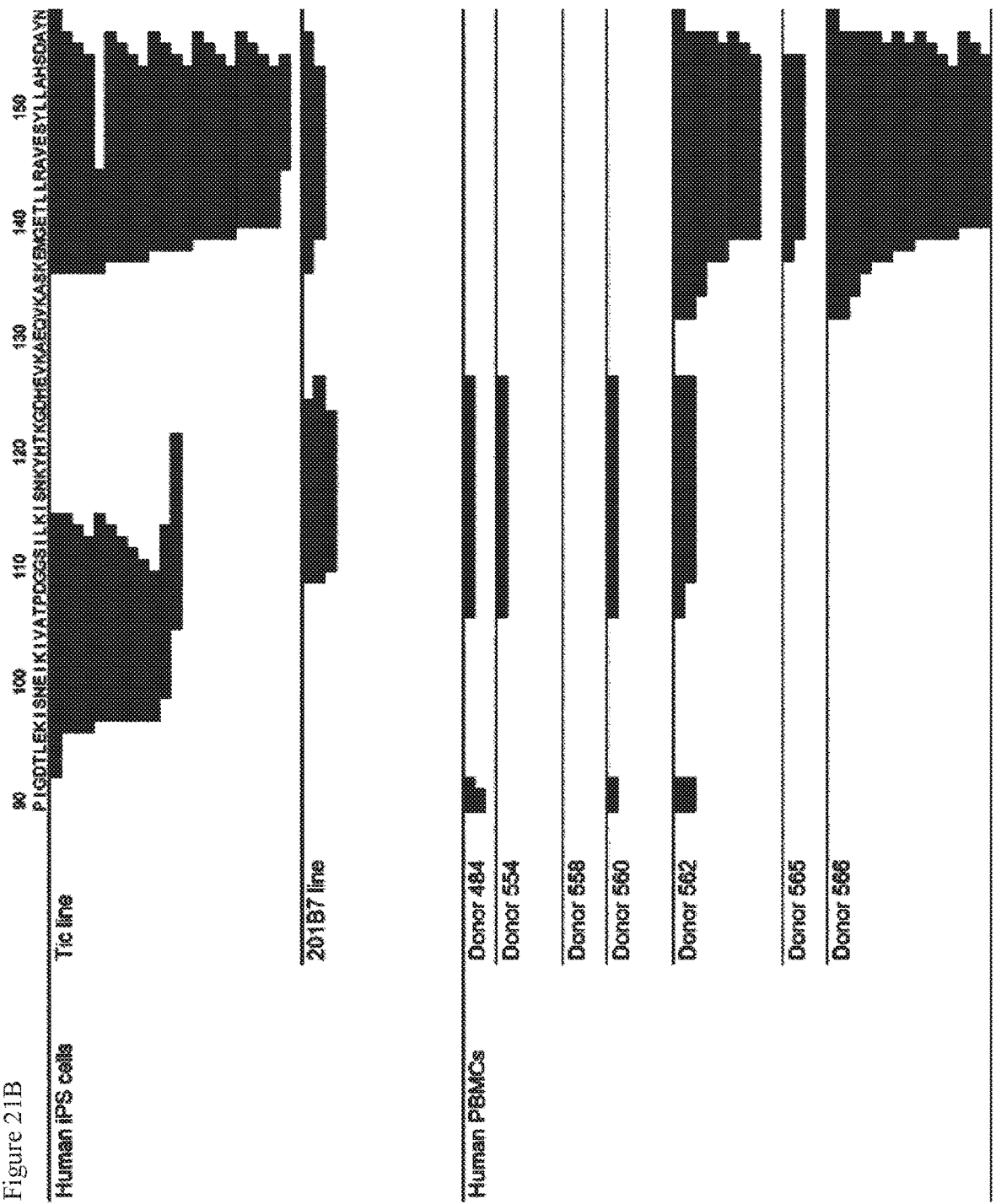

FIGS. 21A and 21B each show results of comparing the amino acid sequences of peptides detected under Bet v1a addition conditions between use of dendritic cell-like cells derived from two types of human iPS cells and use of dendritic cells derived from PBMCs. In the analysis using the dendritic cells derived from PBMCs, the donors had different MHC II molecules, which therefore seemed to result in the difference in the amino acid sequences of the detected peptides among the donors. As for the difference in the detected amino acid sequences between the dendritic cell-like cells derived from two types of iPS cells, the original donors also had different types of MHC II molecules, which therefore seemed to result in the difference in the detected sequences between the lines. Nonetheless, many sequences common in the peptides detected under the Bet v1a addition conditions using the dendritic cell-like cells derived from human iPS cells were consistent with the sequences of the peptides detected using the dendritic cells derived from PBMCs. The detected peptide sequence 140-155 was consistent with the sequence reported as an epitope sequence portion by S. Mutschlener et al., Journal of Allergy and Clinical Immunology Vol. 125 (3), 2010.

More peptides were detected and more antigens were presented using the dendritic cell-like cells derived from human iPS cells than using the dendritic cells derived from PBMCs. These results suggested that use of a dendritic cell differentiated from a stem cell or a progenitor cell derived therefrom has higher sensitivity than that of use of a PBMC-derived dendritic cell. This shows unpredictable remarkable effects of the present invention.

The results described above suggested that MAPPs using a stem cell or a progenitor cell derived therefrom are more sensitive than MAPPs using PBMC and probably serve as an approach useful for reducing protein immunogenicity.

INDUSTRIAL APPLICABILITY

The present invention can be used in the fields of diagnosis or medicine of various bio-pharmaceuticals, for example, by applying the epitope sequence analysis of a protein. In the studies shown herein, sequences presented on MHC class II molecules were detected as to all of the pollen-derived foreign proteins Bet v1a and Phl p1, the antibody drug product infliximab, and the drug product rhFVIII having an amino acid sequence analogous to that of an endogenous protein. The MAPPs of the present invention were capable of detecting epitope sequences for various proteins including bio-pharmaceuticals, regardless of features such as natural and non-natural ones or foreign and endogenous ones. There may be the possibility that the MAPPs of the present invention can be applied to a wide range of purposes such as the development of drugs as well as the analysis of epitopes for allergens or autoimmune diseases.

FREE TEXT OF SEQUENCE LISTING

SEQ ID NOs: 133 to 150: Partial peptide of the H chain of infliximab
SEQ ID NO: 151: Partial peptide of the L chain of infliximab
SEQ ID NOs: 152 and 153: Partial peptide of the H chain of infliximab

The invention claimed is:

1. A method for identifying an epitope on a protein, comprising the following steps:
   (A) contacting a major histocompatibility complex (MHC) molecule-expressing dendritic cell with a target protein, wherein the MHC molecule-expressing dendritic cell is differentiated from a stem cell or a progenitor cell derived from a stem cell;
   (B) isolating a complex of a peptide contained in the target protein and the MHC molecule from the MHC molecule-expressing dendritic cell; and
   (C) eluting the peptide from the complex and identifying the peptide,
   wherein the step (A) further comprises the following steps for differentiating the MHC molecule-expressing dendritic cell from a stem cell or a progenitor cell derived from a stem cell:
   (a) differentiating the stem cell or the progenitor cell derived from the stem cell into a mesodermal progenitor cell;
   (b) differentiating the mesodermal progenitor cell into a monocyte; and
   (c) differentiating the monocyte into an immature dendritic cell, and optionally stimulating the immature dendritic cell to obtain a mature dendritic cell, wherein
   among the steps (a) to (c) at least the steps (a) and (c) are performed in a serum-free medium,
   the step (b) comprises the step of differentiating the mesodermal progenitor cell into the monocyte in a serum-free medium containing a granulocyte macrophage colony-stimulating factor (GM-CSF) and a macrophage colony-stimulating factor (M-CSF), and
   the step (c) comprises the step of:
   (c1) differentiating the monocyte into the immature dendritic cell in a serum-free medium containing a granulocyte macrophage colony-stimulating factor (GM-CSF) and interleukin 4 (IL-4), and optionally comprises the step of:
   (c2) contacting the immature dendritic cell with an immunogen or an immunogen and an inflammatory cytokine to induce the mature dendritic cell;
   the stem cell is selected from the group consisting of an induced pluripotent stem cell (iPS cell), an embryonic stem cell (ES cell), a nuclear transfer ES cell (ntES cell), an embryonic germ stem cell (EG cell), and an adult stem cell; and
   the MHC molecule is a MHC II molecule and the MHC II molecule is HLA-DR, HLA-DQ or HLA-DP.

2. The method according to claim 1, further comprising the following step:

(D) testing whether the identified peptide is an epitope that induces immunogenicity.

3. The method according to claim 1, wherein the MHC molecule-expressing dendritic cell further expresses at least one selected from the group consisting of CD80, CD86, CD206, and CD209.

4. The method according to claim 1, wherein the MHC molecule-expressing dendritic cell expresses CD80, CD86, CD206, and CD209.

5. The method according to claim 1, wherein the MHC molecule-expressing dendritic cell expresses one or more MHC molecule allotypes in a subject intended to receive the target protein.

6. The method according to claim 1, wherein the dendritic cell is an immature dendritic cell, and the immature dendritic cell is contacted with a target protein having immunogenicity to induce the mature dendritic cell.

7. The method according to claim 1, wherein the target protein is selected from the group consisting of (a) a cytokine, (b) a chemokine, (c) a growth factor, (d) an antibody, (e) an enzyme, (f) a structural protein, (g) a hormone, and (h) a fragment of (a)-(g).

\* \* \* \* \*

SEQUENCE LISTING

<160> NUMBER OF SEQ ID NOS: 253

<210> SEQ ID NO 1
<211> LENGTH: 158
<212> TYPE: PRT
<213> ORGANISM: Betula verrucosa

<400> SEQUENCE: 1

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
            20                  25                  30

Val Ala Pro Gln Ala Ile Ser Ser Val Glu Asn Ile Glu Asn Gly Gly
        35                  40                  45

Pro Gly Thr Ile Lys Lys Ile Ser Phe Pro Glu Gly Phe Pro Phe Lys
    50                  55                  60

Tyr Val Lys Asp Arg Val Asp Glu Val Asp His Thr Asn Phe Lys Tyr
65                  70                  75                  80

Asn Tyr Ser Val Ile Glu Gly Gly Pro Ile Gly Asp Thr Leu Glu Lys
                85                  90                  95

Ile Ser Asn Glu Ile Lys Ile Val Ala Thr Pro Asp Gly Gly Ser Ile
            100                 105                 110

Leu Lys Ile Ser Asn Lys Tyr His Thr Lys Gly Asp His Glu Val Lys
        115                 120                 125

Ala Glu Gln Val Lys Ala Ser Lys Glu Met Gly Glu Thr Leu Leu Arg
    130                 135                 140

Ala Val Glu Ser Tyr Leu Leu Ala His Ser Asp Ala Tyr Asn
145                 150                 155

<210> SEQ ID NO 2
<211> LENGTH: 132
<212> TYPE: PRT
<213> ORGANISM: Mus musculus

<400> SEQUENCE: 2

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala
    130

<210> SEQ ID NO 3
<211> LENGTH: 318
<212> TYPE: PRT

<213> ORGANISM: Homo sapiens

<400> SEQUENCE: 3

Pro Ser Ser Lys Ser Thr Ser Gly Gly Thr Ala Ala Leu Gly Cys Leu
1               5                   10                  15

Val Lys Asp Tyr Phe Pro Glu Pro Val Thr Val Ser Trp Asn Ser Gly
            20                  25                  30

Ala Leu Thr Ser Gly Val His Thr Phe Pro Ala Val Leu Gln Ser Ser
        35                  40                  45

Gly Leu Tyr Ser Leu Ser Ser Val Val Thr Val Pro Ser Ser Ser Leu
    50                  55                  60

Gly Thr Gln Thr Tyr Ile Cys Asn Val Asn His Lys Pro Ser Asn Thr
65                  70                  75                  80

Lys Val Asp Lys Lys Val Glu Pro Lys Ser Cys Asp Lys Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
210                 215                 220

Ser Arg Asp Glu Leu Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270

Gly Ser Phe Phe Leu Tyr Ser Lys Leu Thr Val Asp Lys Ser Arg Trp
        275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly Lys
305                 310                 315

<210> SEQ ID NO 4
<211> LENGTH: 117
<212> TYPE: PRT
<213> ORGANISM: Mus musculus

<400> SEQUENCE: 4

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Phe Val Gly Ser Ser
            20                  25                  30

Ile His Trp Tyr Gln Gln Arg Thr Asn Gly Ser Pro Arg Leu Leu Ile

```
                 35                  40                  45
Lys Tyr Ala Ser Glu Ser Met Ser Gly Ile Pro Ser Arg Phe Ser Gly
 50                  55                  60

Ser Gly Ser Gly Thr Asp Phe Thr Leu Ser Ile Asn Thr Val Glu Ser
 65                  70                  75                  80

Glu Asp Ile Ala Asp Tyr Tyr Cys Gln Gln Ser His Ser Trp Pro Phe
                 85                  90                  95

Thr Phe Gly Ser Gly Thr Asn Leu Glu Val Lys Arg Thr Val Ala Ala
                100                 105                 110

Pro Ser Val Phe Ile
            115

<210> SEQ ID NO 5
<211> LENGTH: 97
<212> TYPE: PRT
<213> ORGANISM: Homo sapiens

<400> SEQUENCE: 5

Phe Pro Pro Ser Asp Glu Gln Leu Lys Ser Gly Thr Ala Ser Val Val
 1               5                  10                  15

Cys Leu Leu Asn Asn Phe Tyr Pro Arg Glu Ala Lys Val Gln Trp Lys
                 20                  25                  30

Val Asp Asn Ala Leu Gln Ser Gly Asn Ser Gln Glu Ser Val Thr Glu
                 35                  40                  45

Gln Asp Ser Lys Asp Ser Thr Tyr Ser Leu Ser Ser Thr Leu Thr Leu
 50                  55                  60

Ser Lys Ala Asp Tyr Glu Lys His Lys Val Tyr Ala Cys Glu Val Thr
 65                  70                  75                  80

His Gln Gly Leu Ser Ser Pro Val Thr Lys Ser Phe Asn Arg Gly Glu
                 85                  90                  95

Cys

<210> SEQ ID NO 6
<211> LENGTH: 33
<212> TYPE: PRT
<213> ORGANISM: Betula verrucosa

<400> SEQUENCE: 6

Ile Leu Asp Gly Asp Asn Leu Phe Pro Lys Val Ala Pro Gln Ala Ile
 1               5                  10                  15

Ser Ser Val Glu Asn Ile Glu Gly Asn Gly Gly Pro Gly Thr Ile Lys
                 20                  25                  30

Lys

<210> SEQ ID NO 7
<211> LENGTH: 32
<212> TYPE: PRT
<213> ORGANISM: Betula verrucosa

<400> SEQUENCE: 7

Ile Leu Asp Gly Asp Asn Leu Phe Pro Lys Val Ala Pro Gln Ala Ile
 1               5                  10                  15

Ser Ser Val Glu Asn Ile Glu Gly Asn Gly Gly Pro Gly Thr Ile Lys
                 20                  25                  30

<210> SEQ ID NO 8
<211> LENGTH: 30
<212> TYPE: PRT
```

<213> ORGANISM: Betula verrucosa

<400> SEQUENCE: 8

Ile Leu Asp Gly Asp Asn Leu Phe Pro Lys Val Ala Pro Gln Ala Ile
1               5                   10                  15

Ser Ser Val Glu Asn Ile Glu Gly Asn Gly Gly Pro Gly Thr
            20                  25                  30

<210> SEQ ID NO 9
<211> LENGTH: 29
<212> TYPE: PRT
<213> ORGANISM: Betula verrucosa

<400> SEQUENCE: 9

Ile Leu Asp Gly Asp Asn Leu Phe Pro Lys Val Ala Pro Gln Ala Ile
1               5                   10                  15

Ser Ser Val Glu Asn Ile Glu Gly Asn Gly Gly Pro Gly
            20                  25

<210> SEQ ID NO 10
<211> LENGTH: 31
<212> TYPE: PRT
<213> ORGANISM: Betula verrucosa

<400> SEQUENCE: 10

Leu Asp Gly Asp Asn Leu Phe Pro Lys Val Ala Pro Gln Ala Ile Ser
1               5                   10                  15

Ser Val Glu Asn Ile Glu Gly Asn Gly Gly Pro Gly Thr Ile Lys
            20                  25                  30

<210> SEQ ID NO 11
<211> LENGTH: 30
<212> TYPE: PRT
<213> ORGANISM: Betula verrucosa

<400> SEQUENCE: 11

Asp Gly Asp Asn Leu Phe Pro Lys Val Ala Pro Gln Ala Ile Ser Ser
1               5                   10                  15

Val Glu Asn Ile Glu Gly Asn Gly Gly Pro Gly Thr Ile Lys
            20                  25                  30

<210> SEQ ID NO 12
<211> LENGTH: 26
<212> TYPE: PRT
<213> ORGANISM: Betula verrucosa

<400> SEQUENCE: 12

Leu Phe Pro Lys Val Ala Pro Gln Ala Ile Ser Ser Val Glu Asn Ile
1               5                   10                  15

Glu Gly Asn Gly Gly Pro Gly Thr Ile Lys
            20                  25

<210> SEQ ID NO 13
<211> LENGTH: 23
<212> TYPE: PRT
<213> ORGANISM: Betula verrucosa

<400> SEQUENCE: 13

Leu Phe Pro Lys Val Ala Pro Gln Ala Ile Ser Ser Val Glu Asn Ile
1               5                   10                  15

Glu Gly Asn Gly Gly Pro Gly
            20

<210> SEQ ID NO 14
<211> LENGTH: 25
<212> TYPE: PRT
<213> ORGANISM: Betula verrucosa

<400> SEQUENCE: 14

Phe Pro Lys Val Ala Pro Gln Ala Ile Ser Ser Val Glu Asn Ile Glu
1               5                   10                  15

Gly Asn Gly Gly Pro Gly Thr Ile Lys
            20                  25

<210> SEQ ID NO 15
<211> LENGTH: 24
<212> TYPE: PRT
<213> ORGANISM: Betula verrucosa

<400> SEQUENCE: 15

Lys Val Ala Pro Gln Ala Ile Ser Ser Val Glu Asn Ile Glu Gly Asn
1               5                   10                  15

Gly Gly Pro Gly Thr Ile Lys Lys
            20

<210> SEQ ID NO 16
<211> LENGTH: 23
<212> TYPE: PRT
<213> ORGANISM: Betula verrucosa

<400> SEQUENCE: 16

Lys Val Ala Pro Gln Ala Ile Ser Ser Val Glu Asn Ile Glu Gly Asn
1               5                   10                  15

Gly Gly Pro Gly Thr Ile Lys
            20

<210> SEQ ID NO 17
<211> LENGTH: 20
<212> TYPE: PRT
<213> ORGANISM: Betula verrucosa

<400> SEQUENCE: 17

Lys Val Ala Pro Gln Ala Ile Ser Ser Val Glu Asn Ile Glu Gly Asn
1               5                   10                  15

Gly Gly Pro Gly
            20

<210> SEQ ID NO 18
<211> LENGTH: 22
<212> TYPE: PRT
<213> ORGANISM: Betula verrucosa

<400> SEQUENCE: 18

Val Ala Pro Gln Ala Ile Ser Ser Val Glu Asn Ile Glu Gly Asn Gly
1               5                   10                  15

Gly Pro Gly Thr Ile Lys
            20

<210> SEQ ID NO 19
<211> LENGTH: 19
<212> TYPE: PRT
<213> ORGANISM: Betula verrucosa

<400> SEQUENCE: 19

```
Val Ala Pro Gln Ala Ile Ser Ser Val Glu Asn Ile Glu Gly Asn Gly
1               5                   10                  15

Gly Pro Gly

<210> SEQ ID NO 20
<211> LENGTH: 18
<212> TYPE: PRT
<213> ORGANISM: Betula verrucosa

<400> SEQUENCE: 20

Ala Pro Gln Ala Ile Ser Ser Val Glu Asn Ile Glu Gly Asn Gly Gly
1               5                   10                  15

Pro Gly

<210> SEQ ID NO 21
<211> LENGTH: 15
<212> TYPE: PRT
<213> ORGANISM: Betula verrucosa

<400> SEQUENCE: 21

Ala Pro Gln Ala Ile Ser Ser Val Glu Asn Ile Glu Gly Asn Gly
1               5                   10                  15

<210> SEQ ID NO 22
<211> LENGTH: 14
<212> TYPE: PRT
<213> ORGANISM: Betula verrucosa

<400> SEQUENCE: 22

Ala Pro Gln Ala Ile Ser Ser Val Glu Asn Ile Glu Gly Asn
1               5                   10

<210> SEQ ID NO 23
<211> LENGTH: 18
<212> TYPE: PRT
<213> ORGANISM: Betula verrucosa

<400> SEQUENCE: 23

Gly Gly Pro Gly Thr Ile Lys Lys Ile Ser Phe Pro Glu Gly Phe Pro
1               5                   10                  15

Phe Lys

<210> SEQ ID NO 24
<211> LENGTH: 14
<212> TYPE: PRT
<213> ORGANISM: Betula verrucosa

<400> SEQUENCE: 24

Arg Val Asp Glu Val Asp His Thr Asn Phe Lys Tyr Asn Tyr
1               5                   10

<210> SEQ ID NO 25
<211> LENGTH: 23
<212> TYPE: PRT
<213> ORGANISM: Betula verrucosa

<400> SEQUENCE: 25

Asp Thr Leu Glu Lys Ile Ser Asn Glu Ile Lys Ile Val Ala Thr Pro
1               5                   10                  15

Asp Gly Gly Ser Ile Leu Lys
            20
```

-continued

```
<210> SEQ ID NO 26
<211> LENGTH: 19
<212> TYPE: PRT
<213> ORGANISM: Betula verrucosa

<400> SEQUENCE: 26

Lys Ile Ser Asn Glu Ile Lys Ile Val Ala Thr Pro Asp Gly Gly Ser
1               5                   10                  15

Ile Leu Lys

<210> SEQ ID NO 27
<211> LENGTH: 18
<212> TYPE: PRT
<213> ORGANISM: Betula verrucosa

<400> SEQUENCE: 27

Lys Ile Ser Asn Glu Ile Lys Ile Val Ala Thr Pro Asp Gly Gly Ser
1               5                   10                  15

Ile Leu

<210> SEQ ID NO 28
<211> LENGTH: 17
<212> TYPE: PRT
<213> ORGANISM: Betula verrucosa

<400> SEQUENCE: 28

Lys Ile Ser Asn Glu Ile Lys Ile Val Ala Thr Pro Asp Gly Gly Ser
1               5                   10                  15

Ile

<210> SEQ ID NO 29
<211> LENGTH: 18
<212> TYPE: PRT
<213> ORGANISM: Betula verrucosa

<400> SEQUENCE: 29

Ile Ser Asn Glu Ile Lys Ile Val Ala Thr Pro Asp Gly Gly Ser Ile
1               5                   10                  15

Leu Lys

<210> SEQ ID NO 30
<211> LENGTH: 17
<212> TYPE: PRT
<213> ORGANISM: Betula verrucosa

<400> SEQUENCE: 30

Ile Ser Asn Glu Ile Lys Ile Val Ala Thr Pro Asp Gly Gly Ser Ile
1               5                   10                  15

Leu

<210> SEQ ID NO 31
<211> LENGTH: 16
<212> TYPE: PRT
<213> ORGANISM: Betula verrucosa

<400> SEQUENCE: 31

Ile Ser Asn Glu Ile Lys Ile Val Ala Thr Pro Asp Gly Gly Ser Ile
1               5                   10                  15

<210> SEQ ID NO 32
<211> LENGTH: 15
<212> TYPE: PRT
```

<213> ORGANISM: Betula verrucosa

<400> SEQUENCE: 32

Ile Ser Asn Glu Ile Lys Ile Val Ala Thr Pro Asp Gly Gly Ser
1               5                   10                  15

<210> SEQ ID NO 33
<211> LENGTH: 14
<212> TYPE: PRT
<213> ORGANISM: Betula verrucosa

<400> SEQUENCE: 33

Ile Ser Asn Glu Ile Lys Ile Val Ala Thr Pro Asp Gly Gly
1               5                   10

<210> SEQ ID NO 34
<211> LENGTH: 13
<212> TYPE: PRT
<213> ORGANISM: Betula verrucosa

<400> SEQUENCE: 34

Ile Ser Asn Glu Ile Lys Ile Val Ala Thr Pro Asp Gly
1               5                   10

<210> SEQ ID NO 35
<211> LENGTH: 15
<212> TYPE: PRT
<213> ORGANISM: Betula verrucosa

<400> SEQUENCE: 35

Asn Glu Ile Lys Ile Val Ala Thr Pro Asp Gly Gly Ser Ile Leu
1               5                   10                  15

<210> SEQ ID NO 36
<211> LENGTH: 17
<212> TYPE: PRT
<213> ORGANISM: Betula verrucosa

<400> SEQUENCE: 36

Ala Thr Pro Asp Gly Gly Ser Ile Leu Lys Ile Ser Asn Lys Tyr His
1               5                   10                  15

Thr

<210> SEQ ID NO 37
<211> LENGTH: 23
<212> TYPE: PRT
<213> ORGANISM: Betula verrucosa

<400> SEQUENCE: 37

Lys Glu Met Gly Glu Thr Leu Leu Arg Ala Val Glu Ser Tyr Leu Leu
1               5                   10                  15

Ala His Ser Asp Ala Tyr Asn
                20

<210> SEQ ID NO 38
<211> LENGTH: 21
<212> TYPE: PRT
<213> ORGANISM: Betula verrucosa

<400> SEQUENCE: 38

Lys Glu Met Gly Glu Thr Leu Leu Arg Ala Val Glu Ser Tyr Leu Leu
1               5                   10                  15

Ala His Ser Asp Ala

```
                    20

<210> SEQ ID NO 39
<211> LENGTH: 20
<212> TYPE: PRT
<213> ORGANISM: Betula verrucosa

<400> SEQUENCE: 39

Lys Glu Met Gly Glu Thr Leu Leu Arg Ala Val Glu Ser Tyr Leu Leu
1               5                   10                  15

Ala His Ser Asp
            20

<210> SEQ ID NO 40
<211> LENGTH: 19
<212> TYPE: PRT
<213> ORGANISM: Betula verrucosa

<400> SEQUENCE: 40

Lys Glu Met Gly Glu Thr Leu Leu Arg Ala Val Glu Ser Tyr Leu Leu
1               5                   10                  15

Ala His Ser

<210> SEQ ID NO 41
<211> LENGTH: 9
<212> TYPE: PRT
<213> ORGANISM: Betula verrucosa

<400> SEQUENCE: 41

Lys Glu Met Gly Glu Thr Leu Leu Arg
1               5

<210> SEQ ID NO 42
<211> LENGTH: 20
<212> TYPE: PRT
<213> ORGANISM: Betula verrucosa

<400> SEQUENCE: 42

Glu Met Gly Glu Thr Leu Leu Arg Ala Val Glu Ser Tyr Leu Leu Ala
1               5                   10                  15

His Ser Asp Ala
            20

<210> SEQ ID NO 43
<211> LENGTH: 19
<212> TYPE: PRT
<213> ORGANISM: Betula verrucosa

<400> SEQUENCE: 43

Glu Met Gly Glu Thr Leu Leu Arg Ala Val Glu Ser Tyr Leu Leu Ala
1               5                   10                  15

His Ser Asp

<210> SEQ ID NO 44
<211> LENGTH: 18
<212> TYPE: PRT
<213> ORGANISM: Betula verrucosa

<400> SEQUENCE: 44

Glu Met Gly Glu Thr Leu Leu Arg Ala Val Glu Ser Tyr Leu Leu Ala
1               5                   10                  15

His Ser
```

<210> SEQ ID NO 45
<211> LENGTH: 17
<212> TYPE: PRT
<213> ORGANISM: Betula verrucosa

<400> SEQUENCE: 45

Glu Met Gly Glu Thr Leu Leu Arg Ala Val Glu Ser Tyr Leu Leu Ala
1               5                   10                  15

His

<210> SEQ ID NO 46
<211> LENGTH: 19
<212> TYPE: PRT
<213> ORGANISM: Betula verrucosa

<400> SEQUENCE: 46

Met Gly Glu Thr Leu Leu Arg Ala Val Glu Ser Tyr Leu Leu Ala His
1               5                   10                  15

Ser Asp Ala

<210> SEQ ID NO 47
<211> LENGTH: 18
<212> TYPE: PRT
<213> ORGANISM: Betula verrucosa

<400> SEQUENCE: 47

Met Gly Glu Thr Leu Leu Arg Ala Val Glu Ser Tyr Leu Leu Ala His
1               5                   10                  15

Ser Asp

<210> SEQ ID NO 48
<211> LENGTH: 17
<212> TYPE: PRT
<213> ORGANISM: Betula verrucosa

<400> SEQUENCE: 48

Met Gly Glu Thr Leu Leu Arg Ala Val Glu Ser Tyr Leu Leu Ala His
1               5                   10                  15

Ser

<210> SEQ ID NO 49
<211> LENGTH: 16
<212> TYPE: PRT
<213> ORGANISM: Betula verrucosa

<400> SEQUENCE: 49

Met Gly Glu Thr Leu Leu Arg Ala Val Glu Ser Tyr Leu Leu Ala His
1               5                   10                  15

<210> SEQ ID NO 50
<211> LENGTH: 15
<212> TYPE: PRT
<213> ORGANISM: Betula verrucosa

<400> SEQUENCE: 50

Gly Glu Thr Leu Leu Arg Ala Val Glu Ser Tyr Leu Leu Ala His
1               5                   10                  15

<210> SEQ ID NO 51
<211> LENGTH: 18
<212> TYPE: PRT

-continued

```
<213> ORGANISM: Betula verrucosa

<400> SEQUENCE: 51

Gly Glu Thr Leu Leu Arg Ala Val Glu Ser Tyr Leu Leu Ala His Ser
1               5                   10                  15

Asp Ala

<210> SEQ ID NO 52
<211> LENGTH: 17
<212> TYPE: PRT
<213> ORGANISM: Betula verrucosa

<400> SEQUENCE: 52

Gly Glu Thr Leu Leu Arg Ala Val Glu Ser Tyr Leu Leu Ala His Ser
1               5                   10                  15

Asp

<210> SEQ ID NO 53
<211> LENGTH: 16
<212> TYPE: PRT
<213> ORGANISM: Betula verrucosa

<400> SEQUENCE: 53

Gly Glu Thr Leu Leu Arg Ala Val Glu Ser Tyr Leu Leu Ala His Ser
1               5                   10                  15

<210> SEQ ID NO 54
<211> LENGTH: 17
<212> TYPE: PRT
<213> ORGANISM: Betula verrucosa

<400> SEQUENCE: 54

Glu Thr Leu Leu Arg Ala Val Glu Ser Tyr Leu Leu Ala His Ser Asp
1               5                   10                  15

Ala

<210> SEQ ID NO 55
<211> LENGTH: 16
<212> TYPE: PRT
<213> ORGANISM: Betula verrucosa

<400> SEQUENCE: 55

Glu Thr Leu Leu Arg Ala Val Glu Ser Tyr Leu Leu Ala His Ser Asp
1               5                   10                  15

<210> SEQ ID NO 56
<211> LENGTH: 15
<212> TYPE: PRT
<213> ORGANISM: Betula verrucosa

<400> SEQUENCE: 56

Glu Thr Leu Leu Arg Ala Val Glu Ser Tyr Leu Leu Ala His Ser
1               5                   10                  15

<210> SEQ ID NO 57
<211> LENGTH: 14
<212> TYPE: PRT
<213> ORGANISM: Betula verrucosa

<400> SEQUENCE: 57

Glu Thr Leu Leu Arg Ala Val Glu Ser Tyr Leu Leu Ala His
1               5                   10
```

```
<210> SEQ ID NO 58
<211> LENGTH: 10
<212> TYPE: PRT
<213> ORGANISM: Betula verrucosa

<400> SEQUENCE: 58

Ala Val Glu Ser Tyr Leu Leu Ala His Ser
1               5                   10

<210> SEQ ID NO 59
<211> LENGTH: 20
<212> TYPE: PRT
<213> ORGANISM: Betula verrucosa

<400> SEQUENCE: 59

Leu Phe Pro Lys Val Ala Pro Gln Ala Ile Ser Ser Val Glu Asn Ile
1               5                   10                  15

Glu Gly Asn Gly
            20

<210> SEQ ID NO 60
<211> LENGTH: 18
<212> TYPE: PRT
<213> ORGANISM: Betula verrucosa

<400> SEQUENCE: 60

Gly Pro Ile Gly Asp Thr Leu Glu Lys Ile Ser Asn Glu Ile Lys Ile
1               5                   10                  15

Val Ala

<210> SEQ ID NO 61
<211> LENGTH: 20
<212> TYPE: PRT
<213> ORGANISM: Betula verrucosa

<400> SEQUENCE: 61

Glu Val Asp His Thr Asn Phe Lys Tyr Asn Tyr Ser Val Ile Glu Gly
1               5                   10                  15

Gly Pro Ile Gly
            20

<210> SEQ ID NO 62
<211> LENGTH: 19
<212> TYPE: PRT
<213> ORGANISM: Betula verrucosa

<400> SEQUENCE: 62

Glu Val Asp His Thr Asn Phe Lys Tyr Asn Tyr Ser Val Ile Glu Gly
1               5                   10                  15

Gly Pro Ile

<210> SEQ ID NO 63
<211> LENGTH: 21
<212> TYPE: PRT
<213> ORGANISM: Betula verrucosa

<400> SEQUENCE: 63

Thr Pro Asp Gly Gly Ser Ile Leu Lys Ile Ser Asn Lys Tyr His Thr
1               5                   10                  15

Lys Gly Asp His Glu
            20
```

-continued

<210> SEQ ID NO 64
<211> LENGTH: 20
<212> TYPE: PRT
<213> ORGANISM: Betula verrucosa

<400> SEQUENCE: 64

Leu Phe Lys Ala Phe Ile Leu Asp Gly Asp Asn Leu Phe Pro Lys Val
1               5                   10                  15

Ala Pro Gln Ala
            20

<210> SEQ ID NO 65
<211> LENGTH: 19
<212> TYPE: PRT
<213> ORGANISM: Betula verrucosa

<400> SEQUENCE: 65

Leu Phe Lys Ala Phe Ile Leu Asp Gly Asp Asn Leu Phe Pro Lys Val
1               5                   10                  15

Ala Pro Gln

<210> SEQ ID NO 66
<211> LENGTH: 15
<212> TYPE: PRT
<213> ORGANISM: Betula verrucosa

<400> SEQUENCE: 66

Leu Phe Lys Ala Phe Ile Leu Asp Gly Asp Asn Leu Phe Pro Lys
1               5                   10                  15

<210> SEQ ID NO 67
<211> LENGTH: 14
<212> TYPE: PRT
<213> ORGANISM: Betula verrucosa

<400> SEQUENCE: 67

Leu Phe Lys Ala Phe Ile Leu Asp Gly Asp Asn Leu Phe Pro
1               5                   10

<210> SEQ ID NO 68
<211> LENGTH: 14
<212> TYPE: PRT
<213> ORGANISM: Betula verrucosa

<400> SEQUENCE: 68

Phe Lys Ala Phe Ile Leu Asp Gly Asp Asn Leu Phe Pro Lys
1               5                   10

<210> SEQ ID NO 69
<211> LENGTH: 21
<212> TYPE: PRT
<213> ORGANISM: Betula verrucosa

<400> SEQUENCE: 69

Thr Pro Asp Gly Gly Ser Ile Leu Lys Ile Ser Asn Lys Tyr His Thr
1               5                   10                  15

Lys Gly Asp His Glu
            20

<210> SEQ ID NO 70
<211> LENGTH: 19
<212> TYPE: PRT
<213> ORGANISM: Betula verrucosa

<400> SEQUENCE: 70

Leu Glu Lys Ile Ser Asn Glu Ile Lys Ile Val Ala Thr Pro Asp Gly
1               5                   10                  15

Gly Ser Ile

<210> SEQ ID NO 71
<211> LENGTH: 20
<212> TYPE: PRT
<213> ORGANISM: Betula verrucosa

<400> SEQUENCE: 71

Leu Phe Pro Lys Val Ala Pro Gln Ala Ile Ser Ser Val Glu Asn Ile
1               5                   10                  15

Glu Gly Asn Gly
            20

<210> SEQ ID NO 72
<211> LENGTH: 18
<212> TYPE: PRT
<213> ORGANISM: Betula verrucosa

<400> SEQUENCE: 72

Ala Pro Gln Ala Ile Ser Ser Val Glu Asn Ile Glu Gly Asn Gly Gly
1               5                   10                  15

Pro Gly

<210> SEQ ID NO 73
<211> LENGTH: 20
<212> TYPE: PRT
<213> ORGANISM: Betula verrucosa

<400> SEQUENCE: 73

Leu Phe Pro Lys Val Ala Pro Gln Ala Ile Ser Ser Val Glu Asn Ile
1               5                   10                  15

Glu Gly Asn Gly
            20

<210> SEQ ID NO 74
<211> LENGTH: 20
<212> TYPE: PRT
<213> ORGANISM: Betula verrucosa

<400> SEQUENCE: 74

Leu Phe Lys Ala Phe Ile Leu Asp Gly Asp Asn Leu Phe Pro Lys Val
1               5                   10                  15

Ala Pro Gln Ala
            20

<210> SEQ ID NO 75
<211> LENGTH: 19
<212> TYPE: PRT
<213> ORGANISM: Betula verrucosa

<400> SEQUENCE: 75

Leu Phe Lys Ala Phe Ile Leu Asp Gly Asp Asn Leu Phe Pro Lys Val
1               5                   10                  15

Ala Pro Gln

<210> SEQ ID NO 76
<211> LENGTH: 15

```
<212> TYPE: PRT
<213> ORGANISM: Betula verrucosa

<400> SEQUENCE: 76

Leu Phe Lys Ala Phe Ile Leu Asp Gly Asp Asn Leu Phe Pro Lys
1               5                   10                  15

<210> SEQ ID NO 77
<211> LENGTH: 14
<212> TYPE: PRT
<213> ORGANISM: Betula verrucosa

<400> SEQUENCE: 77

Leu Phe Lys Ala Phe Ile Leu Asp Gly Asp Asn Leu Phe Pro
1               5                   10

<210> SEQ ID NO 78
<211> LENGTH: 20
<212> TYPE: PRT
<213> ORGANISM: Betula verrucosa

<400> SEQUENCE: 78

Glu Val Asp His Thr Asn Phe Lys Tyr Asn Tyr Ser Val Ile Glu Gly
1               5                   10                  15

Gly Pro Ile Gly
            20

<210> SEQ ID NO 79
<211> LENGTH: 21
<212> TYPE: PRT
<213> ORGANISM: Betula verrucosa

<400> SEQUENCE: 79

Thr Pro Asp Gly Gly Ser Ile Leu Lys Ile Ser Asn Lys Tyr His Thr
1               5                   10                  15

Lys Gly Asp His Glu
            20

<210> SEQ ID NO 80
<211> LENGTH: 21
<212> TYPE: PRT
<213> ORGANISM: Betula verrucosa

<400> SEQUENCE: 80

Glu Asn Ile Glu Gly Asn Gly Gly Pro Gly Thr Ile Lys Lys Ile Ser
1               5                   10                  15

Phe Pro Glu Gly Phe
            20

<210> SEQ ID NO 81
<211> LENGTH: 24
<212> TYPE: PRT
<213> ORGANISM: Betula verrucosa

<400> SEQUENCE: 81

Asp Arg Val Asp Glu Val Asp His Thr Asn Phe Lys Tyr Asn Tyr Ser
1               5                   10                  15

Val Ile Glu Gly Gly Pro Ile Gly
            20

<210> SEQ ID NO 82
<211> LENGTH: 20
<212> TYPE: PRT
```

<213> ORGANISM: Betula verrucosa

<400> SEQUENCE: 82

Glu Val Asp His Thr Asn Phe Lys Tyr Asn Tyr Ser Val Ile Glu Gly
1               5                   10                  15

Gly Pro Ile Gly
            20

<210> SEQ ID NO 83
<211> LENGTH: 21
<212> TYPE: PRT
<213> ORGANISM: Betula verrucosa

<400> SEQUENCE: 83

Thr Pro Asp Gly Gly Ser Ile Leu Lys Ile Ser Asn Lys Tyr His Thr
1               5                   10                  15

Lys Gly Asp His Glu
            20

<210> SEQ ID NO 84
<211> LENGTH: 18
<212> TYPE: PRT
<213> ORGANISM: Betula verrucosa

<400> SEQUENCE: 84

Gly Gly Ser Ile Leu Lys Ile Ser Asn Lys Tyr His Thr Lys Gly Asp
1               5                   10                  15

His Glu

<210> SEQ ID NO 85
<211> LENGTH: 27
<212> TYPE: PRT
<213> ORGANISM: Betula verrucosa

<400> SEQUENCE: 85

Val Lys Ala Ser Lys Glu Met Gly Glu Thr Leu Leu Arg Ala Val Glu
1               5                   10                  15

Ser Tyr Leu Leu Ala His Ser Asp Ala Tyr Asn
            20                  25

<210> SEQ ID NO 86
<211> LENGTH: 25
<212> TYPE: PRT
<213> ORGANISM: Betula verrucosa

<400> SEQUENCE: 86

Val Lys Ala Ser Lys Glu Met Gly Glu Thr Leu Leu Arg Ala Val Glu
1               5                   10                  15

Ser Tyr Leu Leu Ala His Ser Asp Ala
            20                  25

<210> SEQ ID NO 87
<211> LENGTH: 23
<212> TYPE: PRT
<213> ORGANISM: Betula verrucosa

<400> SEQUENCE: 87

Ala Ser Lys Glu Met Gly Glu Thr Leu Leu Arg Ala Val Glu Ser Tyr
1               5                   10                  15

Leu Leu Ala His Ser Asp Ala
            20

<210> SEQ ID NO 88
<211> LENGTH: 20
<212> TYPE: PRT
<213> ORGANISM: Betula verrucosa

<400> SEQUENCE: 88

Glu Met

```
<211> LENGTH: 16
<212> TYPE: PRT
<213> ORGANISM: Betula verrucosa

<400> SEQUENCE: 94

Gly Glu Thr Leu Leu Arg Ala Val Glu Ser Tyr Leu Leu Ala His Ser
1               5                   10                  15

<210> SEQ ID NO 95
<211> LENGTH: 15
<212> TYPE: PRT
<213> ORGANISM: Betula verrucosa

<400> SEQUENCE: 95

Pro Glu Gly Phe Pro Phe Lys Tyr Val Lys Asp Arg Val Asp Glu
1               5                   10                  15

<210> SEQ ID NO 96
<211> LENGTH: 21
<212> TYPE: PRT
<213> ORGANISM: Betula verrucosa

<400> SEQUENCE: 96

Asn Ile Glu Gly Asn Gly Gly Pro Gly Thr Ile Lys Lys Ile Ser Phe
1               5                   10                  15

Pro Glu Gly Phe Pro
            20

<210> SEQ ID NO 97
<211> LENGTH: 27
<212> TYPE: PRT
<213> ORGANISM: Betula verrucosa

<400> SEQUENCE: 97

Val Lys Ala Ser Lys Glu Met Gly Glu Thr Leu Leu Arg Ala Val Glu
1               5                   10                  15

Ser Tyr Leu Leu Ala His Ser Asp Ala Tyr Asn
            20                  25

<210> SEQ ID NO 98
<211> LENGTH: 25
<212> TYPE: PRT
<213> ORGANISM: Betula verrucosa

<400> SEQUENCE: 98

Val Lys Ala Ser Lys Glu Met Gly Glu Thr Leu Leu Arg Ala Val Glu
1               5                   10                  15

Ser Tyr Leu Leu Ala His Ser Asp Ala
            20                  25

<210> SEQ ID NO 99
<211> LENGTH: 23
<212> TYPE: PRT
<213> ORGANISM: Betula verrucosa

<400> SEQUENCE: 99

Ala Ser Lys Glu Met Gly Glu Thr Leu Leu Arg Ala Val Glu Ser Tyr
1               5                   10                  15

Leu Leu Ala His Ser Asp Ala
            20

<210> SEQ ID NO 100
<211> LENGTH: 21
```

<212> TYPE: PRT
<213> ORGANISM: Betula verrucosa

<400> SEQUENCE: 100

Lys Glu Met Gly Glu Thr Leu Leu Arg Ala Val Glu Ser Tyr Leu Leu
1               5                   10                  15

Ala His Ser Asp Ala
            20

<210> SEQ ID NO 101
<211> LENGTH: 20
<212> TYPE: PRT
<213> ORGANISM: Betula verrucosa

<400> SEQUENCE: 101

Glu Met Gly Glu Thr Leu Leu Arg Ala Val Glu Ser Tyr Leu Leu Ala
1               5                   10                  15

His Ser Asp Ala
            20

<210> SEQ ID NO 102
<211> LENGTH: 19
<212> TYPE: PRT
<213> ORGANISM: Betula verrucosa

<400> SEQUENCE: 102

Glu Met Gly Glu Thr Leu Leu Arg Ala Val Glu Ser Tyr Leu Leu Ala
1               5                   10                  15

His Ser Asp

<210> SEQ ID NO 103
<211> LENGTH: 19
<212> TYPE: PRT
<213> ORGANISM: Betula verrucosa

<400> SEQUENCE: 103

Met Gly Glu Thr Leu Leu Arg Ala Val Glu Ser Tyr Leu Leu Ala His
1               5                   10                  15

Ser Asp Ala

<210> SEQ ID NO 104
<211> LENGTH: 18
<212> TYPE: PRT
<213> ORGANISM: Betula verrucosa

<400> SEQUENCE: 104

Met Gly Glu Thr Leu Leu Arg Ala Val Glu Ser Tyr Leu Leu Ala His
1               5                   10                  15

Ser Asp

<210> SEQ ID NO 105
<211> LENGTH: 18
<212> TYPE: PRT
<213> ORGANISM: Betula verrucosa

<400> SEQUENCE: 105

Gly Glu Thr Leu Leu Arg Ala Val Glu Ser Tyr Leu Leu Ala His Ser
1               5                   10                  15

Asp Ala

<210> SEQ ID NO 106

```
<211> LENGTH: 17
<212> TYPE: PRT
<213> ORGANISM: Betula verrucosa

<400> SEQUENCE: 106

Gly Glu Thr Leu Leu Arg Ala Val Glu Ser Tyr Leu Leu Ala His Ser
1               5                   10                  15
Asp

<210> SEQ ID NO 107
<211> LENGTH: 16
<212> TYPE: PRT
<213> ORGANISM: Betula verrucosa

<400> SEQUENCE: 107

Gly Glu Thr Leu Leu Arg Ala Val Glu Ser Tyr Leu Leu Ala His Ser
1               5                   10                  15

<210> SEQ ID NO 108
<211> LENGTH: 15
<212> TYPE: PRT
<213> ORGANISM: Betula verrucosa

<400> SEQUENCE: 108

Gly Glu Thr Leu Leu Arg Ala Val Glu Ser Tyr Leu Leu Ala His
1               5                   10                  15

<210> SEQ ID NO 109
<211> LENGTH: 17
<212> TYPE: PRT
<213> ORGANISM: Betula verrucosa

<400> SEQUENCE: 109

Glu Thr Leu Leu Arg Ala Val Glu Ser Tyr Leu Leu Ala His Ser Asp
1               5                   10                  15
Ala

<210> SEQ ID NO 110
<211> LENGTH: 16
<212> TYPE: PRT
<213> ORGANISM: Betula verrucosa

<400> SEQUENCE: 110

Glu Thr Leu Leu Arg Ala Val Glu Ser Tyr Leu Leu Ala His Ser Asp
1               5                   10                  15

<210> SEQ ID NO 111
<211> LENGTH: 15
<212> TYPE: PRT
<213> ORGANISM: Betula verrucosa

<400> SEQUENCE: 111

Glu Thr Leu Leu Arg Ala Val Glu Ser Tyr Leu Leu Ala His Ser
1               5                   10                  15

<210> SEQ ID NO 112
<211> LENGTH: 2332
<212> TYPE: PRT
<213> ORGANISM: Homo sapiens

<400> SEQUENCE: 112

Ala Thr Arg Arg Tyr Tyr Leu Gly Ala Val Glu Leu Ser Trp Asp Tyr
1               5                   10                  15
```

-continued

```
Met Gln Ser Asp Leu Gly Glu Leu Pro Val Asp Ala Arg Phe Pro Pro
             20                  25                  30

Arg Val Pro Lys Ser Phe Pro Phe Asn Thr Ser Val Val Tyr Lys Lys
             35                  40                  45

Thr Leu Phe Val Glu Phe Thr Asp His Leu Phe Asn Ile Ala Lys Pro
 50                  55                  60

Arg Pro Pro Trp Met Gly Leu Leu Gly Pro Thr Ile Gln Ala Glu Val
 65                  70                  75                  80

Tyr Asp Thr Val Val Ile Thr Leu Lys Asn Met Ala Ser His Pro Val
                 85                  90                  95

Ser Leu His Ala Val Gly Val Ser Tyr Trp Lys Ala Ser Glu Gly Ala
             100                 105                 110

Glu Tyr Asp Asp Gln Thr Ser Gln Arg Glu Lys Glu Asp Asp Lys Val
             115                 120                 125

Phe Pro Gly Gly Ser His Thr Tyr Val Trp Gln Val Leu Lys Glu Asn
 130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                 165                 170                 175

Leu Val Cys Arg Glu Gly Ser Leu Ala Lys Glu Lys Thr Gln Thr Leu
             180                 185                 190

His Lys Phe Ile Leu Leu Phe Ala Val Phe Asp Glu Gly Lys Ser Trp
             195                 200                 205

His Ser Glu Thr Lys Asn Ser Leu Met Gln Asp Arg Asp Ala Ala Ser
             210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                 245                 250                 255

Val Ile Gly Met Gly Thr Thr Pro Glu Val His Ser Ile Phe Leu Glu
             260                 265                 270

Gly His Thr Phe Leu Val Arg Asn His Arg Gln Ala Ser Leu Glu Ile
             275                 280                 285

Ser Pro Ile Thr Phe Leu Thr Ala Gln Thr Leu Leu Met Asp Leu Gly
 290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                 325                 330                 335

Met Lys Asn Asn Glu Glu Ala Glu Asp Tyr Asp Asp Asp Leu Thr Asp
             340                 345                 350

Ser Glu Met Asp Val Val Arg Phe Asp Asp Asp Asn Ser Pro Ser Phe
             355                 360                 365

Ile Gln Ile Arg Ser Val Ala Lys Lys His Pro Lys Thr Trp Val His
 370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                 405                 410                 415

Gln Arg Ile Gly Arg Lys Tyr Lys Lys Val Arg Phe Met Ala Tyr Thr
             420                 425                 430

Asp Glu Thr Phe Lys Thr Arg Glu Ala Ile Gln His Glu Ser Gly Ile
```

-continued

```
              435                 440                 445
Leu Gly Pro Leu Leu Tyr Gly Glu Val Gly Asp Thr Leu Leu Ile Ile
450                 455                 460
Phe Lys Asn Gln Ala Ser Arg Pro Tyr Asn Ile Tyr Pro His Gly Ile
465                 470                 475                 480
Thr Asp Val Arg Pro Leu Tyr Ser Arg Arg Leu Pro Lys Gly Val Lys
                485                 490                 495
His Leu Lys Asp Phe Pro Ile Leu Pro Gly Glu Ile Phe Lys Tyr Lys
                500                 505                 510
Trp Thr Val Thr Val Glu Asp Gly Pro Thr Lys Ser Asp Pro Arg Cys
                515                 520                 525
Leu Thr Arg Tyr Tyr Ser Ser Phe Val Asn Met Glu Arg Asp Leu Ala
530                 535                 540
Ser Gly Leu Ile Gly Pro Leu Leu Ile Cys Tyr Lys Glu Ser Val Asp
545                 550                 555                 560
Gln Arg Gly Asn Gln Ile Met Ser Asp Lys Arg Asn Val Ile Leu Phe
                565                 570                 575
Ser Val Phe Asp Glu Asn Arg Ser Trp Tyr Leu Thr Glu Asn Ile Gln
                580                 585                 590
Arg Phe Leu Pro Asn Pro Ala Gly Val Gln Leu Glu Asp Pro Glu Phe
                595                 600                 605
Gln Ala Ser Asn Ile Met His Ser Ile Asn Gly Tyr Val Phe Asp Ser
                610                 615                 620
Leu Gln Leu Ser Val Cys Leu His Glu Val Ala Tyr Trp Tyr Ile Leu
625                 630                 635                 640
Ser Ile Gly Ala Gln Thr Asp Phe Leu Ser Val Phe Phe Ser Gly Tyr
                645                 650                 655
Thr Phe Lys His Lys Met Val Tyr Glu Asp Thr Leu Thr Leu Phe Pro
                660                 665                 670
Phe Ser Gly Glu Thr Val Phe Met Ser Met Glu Asn Pro Gly Leu Trp
                675                 680                 685
Ile Leu Gly Cys His Asn Ser Asp Phe Arg Asn Arg Gly Met Thr Ala
                690                 695                 700
Leu Leu Lys Val Ser Ser Cys Asp Lys Asn Thr Gly Asp Tyr Tyr Glu
705                 710                 715                 720
Asp Ser Tyr Glu Asp Ile Ser Ala Tyr Leu Leu Ser Lys Asn Asn Ala
                725                 730                 735
Ile Glu Pro Arg Ser Phe Ser Gln Asn Ser Arg His Pro Ser Thr Arg
                740                 745                 750
Gln Tyr Gln Phe Asn Ala Thr Thr Ile Pro Glu Asn Asp Ile Glu Lys
                755                 760                 765
Thr Asp Pro Trp Phe Ala His Arg Thr Pro Met Pro Lys Ile Gln Asn
                770                 775                 780
Val Ser Ser Ser Asp Leu Leu Met Leu Leu Arg Gln Ser Pro Thr Pro
785                 790                 795                 800
His Gly Leu Ser Leu Ser Asp Leu Gln Glu Ala Lys Tyr Glu Thr Phe
                805                 810                 815
Ser Asp Asp Pro Ser Pro Gly Ala Ile Asp Ser Asn Asn Ser Leu Ser
                820                 825                 830
Glu Met Thr His Phe Arg Pro Gln Leu His His Ser Gly Asp Met Val
                835                 840                 845
Phe Thr Pro Glu Ser Gly Leu Gln Leu Arg Leu Asn Glu Lys Leu Gly
850                 855                 860
```

```
Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
            885                 890                 895

Gly Thr Asp Asn Thr Ser Ser Leu Gly Pro Pro Ser Met Pro Val His
        900                 905                 910

Tyr Asp Ser Gln Leu Asp Thr Thr Leu Phe Gly Lys Lys Ser Ser Pro
            915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Gly Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
            980                 985                 990

Val Ser Ile Ser Leu Leu Lys Thr Asn Lys Thr Ser Asn Asn Ser Ala
        995                 1000                1005

Thr Asn Arg Lys Thr His Ile Asp Gly Pro Ser Leu Leu Ile Glu
1010                1015                1020

Asn Ser Pro Ser Val Trp Gln Asn Ile Leu Glu Ser Asp Thr Glu
1025                1030                1035

Phe Lys Lys Val Thr Pro Leu Ile His Asp Arg Met Leu Met Asp
1040                1045                1050

Lys Asn Ala Thr Ala Leu Arg Leu Asn His Met Ser Asn Lys Thr
1055                1060                1065

Thr Ser Ser Lys Asn Met Glu Met Val Gln Gln Lys Lys Glu Gly
1070                1075                1080

Pro Ile Pro Pro Asp Ala Gln Asn Pro Asp Met Ser Phe Phe Lys
1085                1090                1095

Met Leu Phe Leu Pro Glu Ser Ala Arg Trp Ile Gln Arg Thr His
1100                1105                1110

Gly Lys Asn Ser Leu Asn Ser Gly Gln Gly Pro Ser Pro Lys Gln
1115                1120                1125

Leu Val Ser Leu Gly Pro Glu Lys Ser Val Glu Gly Gln Asn Phe
1130                1135                1140

Leu Ser Glu Lys Asn Lys Val Val Val Gly Lys Gly Glu Phe Thr
1145                1150                1155

Lys Asp Val Gly Leu Lys Glu Met Val Phe Pro Ser Ser Arg Asn
1160                1165                1170

Leu Phe Leu Thr Asn Leu Asp Asn Leu His Glu Asn Asn Thr His
1175                1180                1185

Asn Gln Glu Lys Lys Ile Gln Glu Glu Ile Glu Lys Lys Glu Thr
1190                1195                1200

Leu Ile Gln Glu Asn Val Val Leu Pro Gln Ile His Thr Val Thr
1205                1210                1215

Gly Thr Lys Asn Phe Met Lys Asn Leu Phe Leu Leu Ser Thr Arg
1220                1225                1230

Gln Asn Val Glu Gly Ser Tyr Glu Gly Ala Tyr Ala Pro Val Leu
1235                1240                1245

Gln Asp Phe Arg Ser Leu Asn Asp Ser Thr Asn Arg Thr Lys Lys
1250                1255                1260
```

-continued

His Thr Ala His Phe Ser Lys Lys Gly Glu Glu Glu Asn Leu Glu
1265                1270                    1275

Gly Leu Gly Asn Gln Thr Lys Gln Ile Val Glu Lys Tyr Ala Cys
1280                1285                    1290

Thr Thr Arg Ile Ser Pro Asn Thr Ser Gln Gln Asn Phe Val Thr
1295                1300                    1305

Gln Arg Ser Lys Arg Ala Leu Lys Gln Phe Arg Leu Pro Leu Glu
1310                1315                    1320

Glu Thr Glu Leu Glu Lys Arg Ile Ile Val Asp Asp Thr Ser Thr
1325                1330                    1335

Gln Trp Ser Lys Asn Met Lys His Leu Thr Pro Ser Thr Leu Thr
1340                1345                    1350

Gln Ile Asp Tyr Asn Glu Lys Glu Lys Gly Ala Ile Thr Gln Ser
1355                1360                    1365

Pro Leu Ser Asp Cys Leu Thr Arg Ser His Ser Ile Pro Gln Ala
1370                1375                    1380

Asn Arg Ser Pro Leu Pro Ile Ala Lys Val Ser Ser Phe Pro Ser
1385                1390                    1395

Ile Arg Pro Ile Tyr Leu Thr Arg Val Leu Phe Gln Asp Asn Ser
1400                1405                    1410

Ser His Leu Pro Ala Ala Ser Tyr Arg Lys Lys Asp Ser Gly Val
1415                1420                    1425

Gln Glu Ser Ser His Phe Leu Gln Gly Ala Lys Lys Asn Asn Leu
1430                1435                    1440

Ser Leu Ala Ile Leu Thr Leu Glu Met Thr Gly Asp Gln Arg Glu
1445                1450                    1455

Val Gly Ser Leu Gly Thr Ser Ala Thr Asn Ser Val Thr Tyr Lys
1460                1465                    1470

Lys Val Glu Asn Thr Val Leu Pro Lys Pro Asp Leu Pro Lys Thr
1475                1480                    1485

Ser Gly Lys Val Glu Leu Leu Pro Lys Val His Ile Tyr Gln Lys
1490                1495                    1500

Asp Leu Phe Pro Thr Glu Thr Ser Asn Gly Ser Pro Gly His Leu
1505                1510                    1515

Asp Leu Val Glu Gly Ser Leu Leu Gln Gly Thr Glu Gly Ala Ile
1520                1525                    1530

Lys Trp Asn Glu Ala Asn Arg Pro Gly Lys Val Pro Phe Leu Arg
1535                1540                    1545

Val Ala Thr Glu Ser Ser Ala Lys Thr Pro Ser Lys Leu Leu Asp
1550                1555                    1560

Pro Leu Ala Trp Asp Asn His Tyr Gly Thr Gln Ile Pro Lys Glu
1565                1570                    1575

Glu Trp Lys Ser Gln Glu Lys Ser Pro Glu Lys Thr Ala Phe Lys
1580                1585                    1590

Lys Lys Asp Thr Ile Leu Ser Leu Asn Ala Cys Glu Ser Asn His
1595                1600                    1605

Ala Ile Ala Ala Ile Asn Glu Gly Gln Asn Lys Pro Glu Ile Glu
1610                1615                    1620

Val Thr Trp Ala Lys Gln Gly Arg Thr Glu Arg Leu Cys Ser Gln
1625                1630                    1635

Asn Pro Pro Val Leu Lys Arg His Gln Arg Glu Ile Thr Arg Thr
1640                1645                    1650

Thr Leu Gln Ser Asp Gln Glu Glu Ile Asp Tyr Asp Asp Thr Ile

-continued

```
          1655                1660                1665

Ser Val Glu Met Lys Lys Glu Asp Phe Asp Ile Tyr Asp Glu Asp
    1670                1675                1680

Glu Asn Gln Ser Pro Arg Ser Phe Gln Lys Lys Thr Arg His Tyr
    1685                1690                1695

Phe Ile Ala Ala Val Glu Arg Leu Trp Asp Tyr Gly Met Ser Ser
    1700                1705                1710

Ser Pro His Val Leu Arg Asn Arg Ala Gln Ser Gly Ser Val Pro
    1715                1720                1725

Gln Phe Lys Lys Val Val Phe Gln Glu Phe Thr Asp Gly Ser Phe
    1730                1735                1740

Thr Gln Pro Leu Tyr Arg Gly Glu Leu Asn Glu His Leu Gly Leu
    1745                1750                1755

Leu Gly Pro Tyr Ile Arg Ala Glu Val Glu Asp Asn Ile Met Val
    1760                1765                1770

Thr Phe Arg Asn Gln Ala Ser Arg Pro Tyr Ser Phe Tyr Ser Ser
    1775                1780                1785

Leu Ile Ser Tyr Glu Glu Asp Gln Arg Gln Gly Ala Glu Pro Arg
    1790                1795                1800

Lys Asn Phe Val Lys Pro Asn Glu Thr Lys Thr Tyr Phe Trp Lys
    1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055
```

```
Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205

Arg Leu His Leu Gln Gly Arg Ser Asn Ala Trp Arg Pro Gln Val
    2210                2215                2220

Asn Asn Pro Lys Glu Trp Leu Gln Val Asp Phe Gln Lys Thr Met
    2225                2230                2235

Lys Val Thr Gly Val Thr Thr Gln Gly Val Lys Ser Leu Leu Thr
    2240                2245                2250

Ser Met Tyr Val Lys Glu Phe Leu Ile Ser Ser Ser Gln Asp Gly
    2255                2260                2265

His Gln Trp Thr Leu Phe Phe Gln Asn Gly Lys Val Lys Val Phe
    2270                2275                2280

Gln Gly Asn Gln Asp Ser Phe Thr Pro Val Val Asn Ser Leu Asp
    2285                2290                2295

Pro Pro Leu Leu Thr Arg Tyr Leu Arg Ile His Pro Gln Ser Trp
    2300                2305                2310

Val His Gln Ile Ala Leu Arg Met Glu Val Leu Gly Cys Glu Ala
    2315                2320                2325

Gln Asp Leu Tyr
    2330

<210> SEQ ID NO 113
<211> LENGTH: 180
<212> TYPE: PRT
<213> ORGANISM: Phleum pratense

<400> SEQUENCE: 113

Ile Pro Lys Val Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
                20                  25                  30

Gly Pro Lys Asp Asn Gly Gly Ala Cys Gly Tyr Lys Asp Val Asp Lys
                35                  40                  45

Pro Pro Phe Ser Gly Met Thr Gly Cys Gly Asn Thr Pro Ile Phe Lys
        50                  55                  60

Ser Gly Arg Gly Cys Gly Ser Cys Phe Glu Ile Lys Cys Thr Lys Pro
```

```
                65                  70                  75                  80
Glu Ala Cys Ser Gly Glu Pro Val Val His Ile Thr Asp Asp Asn
                    85                  90                  95
Glu Glu Pro Ile Ala Pro Tyr His Phe Asp Leu Ser Gly His Ala Phe
                100                 105                 110
Gly Ala Met Ala Lys Lys Gly Asp Glu Gln Lys Leu Arg Ser Ala Gly
                115                 120                 125
Glu Leu Glu Leu Gln Phe Arg Arg Val Lys Cys Lys Tyr Pro Glu Gly
            130                 135                 140
Thr Lys Val Thr Phe His Val Glu Lys Gly Ser Asn Pro Asn Tyr Leu
145                 150                 155                 160
Ala Leu Leu Val Lys Tyr Val Asn Gly Asp Gly Asp Val Val Ala Val
                165                 170                 175
Asp Ile Lys Glu
            180

<210> SEQ ID NO 114
<211> LENGTH: 16
<212> TYPE: PRT
<213> ORGANISM: Betula verrucosa

<400> SEQUENCE: 114

Arg Leu Phe Lys Ala Phe Ile Leu Asp Gly Asp Asn Leu Phe Pro Lys
1               5                   10                  15

<210> SEQ ID NO 115
<211> LENGTH: 15
<212> TYPE: PRT
<213> ORGANISM: Betula verrucosa

<400> SEQUENCE: 115

Leu Phe Lys Ala Phe Ile Leu Asp Gly Asp Asn Leu Phe Pro Lys
1               5                   10                  15

<210> SEQ ID NO 116
<211> LENGTH: 16
<212> TYPE: PRT
<213> ORGANISM: Betula verrucosa

<400> SEQUENCE: 116

Leu Phe Lys Ala Phe Ile Leu Asp Gly Asp Asn Leu Phe Pro Lys Val
1               5                   10                  15

<210> SEQ ID NO 117
<211> LENGTH: 17
<212> TYPE: PRT
<213> ORGANISM: Betula verrucosa

<400> SEQUENCE: 117

Leu Phe Lys Ala Phe Ile Leu Asp Gly Asp Asn Leu Phe Pro Lys Val
1               5                   10                  15

Ala

<210> SEQ ID NO 118
<211> LENGTH: 18
<212> TYPE: PRT
<213> ORGANISM: Betula verrucosa

<400> SEQUENCE: 118

Leu Phe Lys Ala Phe Ile Leu Asp Gly Asp Asn Leu Phe Pro Lys Val
1               5                   10                  15
```

Ala Pro

<210> SEQ ID NO 119
<211> LENGTH: 19
<212> TYPE: PRT
<213> ORGANISM: Betula verrucosa

<400> SEQUENCE: 119

Leu Phe Lys Ala Phe Ile Leu Asp Gly Asp Asn Leu Phe Pro Lys Val
1               5                   10                  15

Ala Pro Gln

<210> SEQ ID NO 120
<211> LENGTH: 20
<212> TYPE: PRT
<213> ORGANISM: Betula verrucosa

<400> SEQUENCE: 120

Leu Phe Lys Ala Phe Ile Leu Asp Gly Asp Asn Leu Phe Pro Lys Val
1               5                   10                  15

Ala Pro Gln Ala
            20

<210> SEQ ID NO 121
<211> LENGTH: 26
<212> TYPE: PRT
<213> ORGANISM: Betula verrucosa

<400> SEQUENCE: 121

Leu Phe Lys Ala Phe Ile Leu Asp Gly Asp Asn Leu Phe Pro Lys Val
1               5                   10                  15

Ala Pro Gln Ala Ile Ser Ser Val Glu Asn
            20                  25

<210> SEQ ID NO 122
<211> LENGTH: 30
<212> TYPE: PRT
<213> ORGANISM: Betula verrucosa

<400> SEQUENCE: 122

Leu Phe Lys Ala Phe Ile Leu Asp Gly Asp Asn Leu Phe Pro Lys Val
1 5 10 15

Ala Pro Gln Ala Ile Ser Ser Val Glu Asn Ile Glu Gly Asn
20 25 30

<210> SEQ ID NO 123
<211> LENGTH: 14
<212> TYPE: PRT
<213> ORGANISM: Betula verrucosa

<400> SEQUENCE: 123

Phe Lys Ala Phe Ile Leu Asp Gly Asp Asn Leu Phe Pro Lys
1 5 10

<210> SEQ ID NO 124
<211> LENGTH: 13
<212> TYPE: PRT
<213> ORGANISM: Betula verrucosa

<400> SEQUENCE: 124

Lys Ala Phe Ile Leu Asp Gly Asp Asn Leu Phe Pro Lys
1 5 10

<210> SEQ ID NO 125
<211> LENGTH: 17
<212> TYPE: PRT
<213> ORGANISM: Betula verrucosa

<400> SEQUENCE: 125

Lys Ala Phe Ile Leu Asp Gly Asp Asn Leu Phe Pro Lys Val Ala Pro
1               5                   10                  15

Gln

<210> SEQ ID NO 126
<211> LENGTH: 12
<212> TYPE: PRT
<213> ORGANISM: Betula verrucosa

<400> SEQUENCE: 126

Ala Phe Ile Leu Asp Gly Asp Asn Leu Phe Pro Lys
1               5                   10

<210> SEQ ID NO 127
<211> LENGTH: 16
<212> TYPE: PRT
<213> ORGANISM: Betula verrucosa

<400> SEQUENCE: 127

Gly Gly Ser Ile Leu Lys Ile Ser Asn Lys Tyr His Thr Lys Gly Asp
1               5                   10                  15

<210> SEQ ID NO 128
<211> LENGTH: 18
<212> TYPE: PRT
<213> ORGANISM: Betula verrucosa

<400> SEQUENCE: 128

Gly Gly Ser Ile Leu Lys Ile Ser Asn Lys Tyr His Thr Lys Gly Asp
1               5                   10                  15

His Glu

<210> SEQ ID NO 129
<211> LENGTH: 14
<212> TYPE: PRT
<213> ORGANISM: Betula verrucosa

<400> SEQUENCE: 129

Gly Ser Ile Leu Lys Ile Ser Asn Lys Tyr His Thr Lys Gly
1               5                   10

<210> SEQ ID NO 130
<211> LENGTH: 21
<212> TYPE: PRT
<213> ORGANISM: Betula verrucosa

<400> SEQUENCE: 130

Lys Glu Met Gly Glu Thr Leu Leu Arg Ala Val Glu Ser Tyr Leu Leu
1               5                   10                  15

Ala His Ser Asp Ala
                20

<210> SEQ ID NO 131
<211> LENGTH: 15
<212> TYPE: PRT
<213> ORGANISM: Betula verrucosa

```
<400> SEQUENCE: 131

Gly Glu Thr Leu Leu Arg Ala Val Glu Ser Tyr Leu Leu Ala His
1               5                   10                  15

<210> SEQ ID NO 132
<211> LENGTH: 19
<212> TYPE: PRT
<213> ORGANISM: Betula verrucosa

<400> SEQUENCE: 132

Val Ala Pro Gln Ala Ile Ser Ser Val Glu Asn Ile Glu Gly Asn Gly
1               5                   10                  15

Gly Pro Gly

<210> SEQ ID NO 133
<211> LENGTH: 21
<212> TYPE: PRT
<213> ORGANISM: Artificial Sequence
<220> FEATURE:
<223> OTHER INFORMATION: A partial peptide of Infliximab Heavy Chain

<400> SEQUENCE: 133

Arg Asp Asp Ser Lys Ser Ala Val Tyr Leu Gln Met Thr Asp Leu Arg
1               5                   10                  15

Thr Glu Asp Thr Gly
            20

<210> SEQ ID NO 134
<211> LENGTH: 20
<212> TYPE: PRT
<213> ORGANISM: Artificial Sequence
<220> FEATURE:
<223> OTHER INFORMATION: A partial peptide of Infliximab Heavy Chain

<400> SEQUENCE: 134

Arg Asp Asp Ser Lys Ser Ala Val Tyr Leu Gln Met Thr Asp Leu Arg
1               5                   10                  15

Thr Glu Asp Thr
            20

<210> SEQ ID NO 135
<211> LENGTH: 19
<212> TYPE: PRT
<213> ORGANISM: Artificial Sequence
<220> FEATURE:
<223> OTHER INFORMATION: A partial peptide of Infliximab Heavy Chain

<400> SEQUENCE: 135

Arg Asp Asp Ser Lys Ser Ala Val Tyr Leu Gln Met Thr Asp Leu Arg
1               5                   10                  15

Thr Glu Asp

<210> SEQ ID NO 136
<211> LENGTH: 20
<212> TYPE: PRT
<213> ORGANISM: Artificial Sequence
<220> FEATURE:
<223> OTHER INFORMATION: A partial peptide of Infliximab Heavy Chain

<400> SEQUENCE: 136

Asp Asp Ser Lys Ser Ala Val Tyr Leu Gln Met Thr Asp Leu Arg Thr
1               5                   10                  15
```

Glu Asp Thr Gly
            20

<210> SEQ ID NO 137
<211> LENGTH: 19
<212> TYPE: PRT
<213> ORGANISM: Artificial Sequence
<220> FEATURE:
<223> OTHER INFORMATION: A partial peptide of Infliximab Heavy Chain

<400> SEQUENCE: 137

Asp Asp Ser Lys Ser Ala Val Tyr Leu Gln Met Thr Asp Leu Arg Thr
1               5                   10                  15

Glu Asp Thr

<210> SEQ ID NO 138
<211> LENGTH: 19
<212> TYPE: PRT
<213> ORGANISM: Artificial Sequence
<220> FEATURE:
<223> OTHER INFORMATION: A partial peptide of Infliximab Heavy Chain

<400> SEQUENCE: 138

Asp Ser Lys Ser Ala Val Tyr Leu Gln Met Thr Asp Leu Arg Thr Glu
1               5                   10                  15

Asp Thr Gly

<210> SEQ ID NO 139
<211> LENGTH: 18
<212> TYPE: PRT
<213> ORGANISM: Artificial Sequence
<220> FEATURE:
<223> OTHER INFORMATION: A partial peptide of Infliximab Heavy Chain

<400> SEQUENCE: 139

Ser Lys Ser Ala Val Tyr Leu Gln Met Thr Asp Leu Arg Thr Glu Asp
1               5                   10                  15

Thr Gly

<210> SEQ ID NO 140
<211> LENGTH: 17
<212> TYPE: PRT
<213> ORGANISM: Artificial Sequence
<220> FEATURE:
<223> OTHER INFORMATION: A partial peptide of Infliximab Heavy Chain

<400> SEQUENCE: 140

Ser Lys Ser Ala Val Tyr Leu Gln Met Thr Asp Leu Arg Thr Glu Asp
1               5                   10                  15

Thr

<210> SEQ ID NO 141
<211> LENGTH: 16
<212> TYPE: PRT
<213> ORGANISM: Artificial Sequence
<220> FEATURE:
<223> OTHER INFORMATION: A partial peptide of Infliximab Heavy Chain

<400> SEQUENCE: 141

Ser Lys Ser Ala Val Tyr Leu Gln Met Thr Asp Leu Arg Thr Glu Asp
1               5                   10                  15

<210> SEQ ID NO 142
<211> LENGTH: 17

```
<212> TYPE: PRT
<213> ORGANISM: Artificial Sequence
<220> FEATURE:
<223> OTHER INFORMATION: A partial peptide of Infliximab Heavy Chain

<400> SEQUENCE: 142

Lys Ser Ala Val Tyr Leu Gln Met Thr Asp Leu Arg Thr Glu Asp Thr
1               5                   10                  15

Gly

<210> SEQ ID NO 143
<211> LENGTH: 16
<212> TYPE: PRT
<213> ORGANISM: Artificial Sequence
<220> FEATURE:
<223> OTHER INFORMATION: A partial peptide of Infliximab Heavy Chain

<400> SEQUENCE: 143

Lys Ser Ala Val Tyr Leu Gln Met Thr Asp Leu Arg Thr Glu Asp Thr
1               5                   10                  15

<210> SEQ ID NO 144
<211> LENGTH: 15
<212> TYPE: PRT
<213> ORGANISM: Artificial Sequence
<220> FEATURE:
<223> OTHER INFORMATION: A partial peptide of Infliximab Heavy Chain

<400> SEQUENCE: 144

Lys Ser Ala Val Tyr Leu Gln Met Thr Asp Leu Arg Thr Glu Asp
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: A partial peptide of Infliximab Heavy Chain

<400> SEQUENCE: 145

Ser Ala Val Tyr Leu Gln Met Thr Asp Leu Arg Thr Glu Asp Thr Gly
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: A partial peptide of Infliximab Heavy Chain

<400> SEQUENCE: 146

Ser Ala Val Tyr Leu Gln Met Thr Asp Leu Arg Thr Glu Asp Thr
1               5                   10                  15

<210> SEQ ID NO 147
<211> LENGTH: 14
<212> TYPE: PRT
<213> ORGANISM: Artificial Sequence
<220> FEATURE:
<223> OTHER INFORMATION: A partial peptide of Infliximab Heavy Chain

<400> SEQUENCE: 147

Ser Ala Val Tyr Leu Gln Met Thr Asp Leu Arg Thr Glu Asp
1               5                   10

<210> SEQ ID NO 148
```

```
<211> LENGTH: 13
<212> TYPE: PRT
<213> ORGANISM: Artificial Sequence
<220> FEATURE:
<223> OTHER INFORMATION: A partial peptide of Infliximab Heavy Chain

<400> SEQUENCE: 148

Ser Ala Val Tyr Leu Gln Met Thr Asp Leu Arg Thr Glu
1               5                   10

<210> SEQ ID NO 149
<211> LENGTH: 17
<212> TYPE: PRT
<213> ORGANISM: Artificial Sequence
<220> FEATURE:
<223> OTHER INFORMATION: A partial peptide of Infliximab Heavy Chain

<400> SEQUENCE: 149

Leu Val Lys Asp Tyr Phe Pro Glu Pro Val Thr Val Ser Trp Asn Ser
1               5                   10                  15

Gly

<210> SEQ ID NO 150
<211> LENGTH: 27
<212> TYPE: PRT
<213> ORGANISM: Artificial Sequence
<220> FEATURE:
<223> OTHER INFORMATION: A partial peptide of Infliximab Heavy Chain

<400> SEQUENCE: 150

Thr Val Pro Ser Ser Ser Leu Gly Thr Gln Thr Tyr Ile Cys Asn Val
1               5                   10                  15

Asn His Lys Pro Ser Asn Thr Lys Val Asp Lys
            20                  25

<210> SEQ ID NO 151
<211> LENGTH: 15
<212> TYPE: PRT
<213> ORGANISM: Artificial Sequence
<220> FEATURE:
<223> OTHER INFORMATION: A partial peptide of Infliximab Light Chain

<400> SEQUENCE: 151

Gln Ser Pro Ala Ile Leu Ser Val Ser Pro Gly Glu Arg Val Ser
1               5                   10                  15

<210> SEQ ID NO 152
<211> LENGTH: 15
<212> TYPE: PRT
<213> ORGANISM: Artificial Sequence
<220> FEATURE:
<223> OTHER INFORMATION: A partial peptide of Infliximab Heavy Chain

<400> SEQUENCE: 152

Leu Val Gln Pro Gly Gly Ser Met Lys Leu Ser Cys Val Ala Ser
1               5                   10                  15

<210> SEQ ID NO 153
<211> LENGTH: 17
<212> TYPE: PRT
<213> ORGANISM: Artificial Sequence
<220> FEATURE:
<223> OTHER INFORMATION: A partial peptide of Infliximab Heavy Chain

<400> SEQUENCE: 153

Leu Val Lys Asp Tyr Phe Pro Glu Pro Val Thr Val Ser Trp Asn Ser
```

1               5                   10                  15

Gly

<210> SEQ ID NO 154
<211> LENGTH: 24
<212> TYPE: PRT
<213> ORGANISM: Homo sapiens

<400> SEQUENCE: 154

Gly Pro Thr Ile Gln Ala Glu Val Tyr Asp Thr Val Val Ile Thr Leu
1               5                   10                  15

Lys Asn Met Ala Ser His Pro Val
            20

<210> SEQ ID NO 155
<211> LENGTH: 25
<212> TYPE: PRT
<213> ORGANISM: Homo sapiens

<400> SEQUENCE: 155

Gly Pro Thr Ile Gln Ala Glu Val Tyr Asp Thr Val Val Ile Thr Leu
1               5                   10                  15

Lys Asn Met Ala Ser His Pro Val Ser
            20                  25

<210> SEQ ID NO 156
<211> LENGTH: 18
<212> TYPE: PRT
<213> ORGANISM: Homo sapiens

<400> SEQUENCE: 156

Glu Val Tyr Asp Thr Val Val Ile Thr Leu Lys Asn Met Ala Ser His
1               5                   10                  15

Pro Val

<210> SEQ ID NO 157
<211> LENGTH: 19
<212> TYPE: PRT
<213> ORGANISM: Homo sapiens

<400> SEQUENCE: 157

Glu Val Tyr Asp Thr Val Val Ile Thr Leu Lys Asn Met Ala Ser His
1               5                   10                  15

Pro Val Ser

<210> SEQ ID NO 158
<211> LENGTH: 17
<212> TYPE: PRT
<213> ORGANISM: Homo sapiens

<400> SEQUENCE: 158

Val Tyr Asp Thr Val Val Ile Thr Leu Lys Asn Met Ala Ser His Pro
1               5                   10                  15

Val

<210> SEQ ID NO 159
<211> LENGTH: 18
<212> TYPE: PRT
<213> ORGANISM: Homo sapiens

<400> SEQUENCE: 159

Val Tyr Asp Thr Val Val Ile Thr Leu Lys Asn Met Ala Ser His Pro
1               5                   10                  15

Val Ser

<210> SEQ ID NO 160
<211> LENGTH: 16
<212> TYPE: PRT
<213> ORGANISM: Homo sapiens

<400> SEQUENCE: 160

Tyr Asp Thr Val Val Ile Thr Leu Lys Asn Met Ala Ser His Pro Val
1               5                   10                  15

<210> SEQ ID NO 161
<211> LENGTH: 17
<212> TYPE: PRT
<213> ORGANISM: Homo sapiens

<400> SEQUENCE: 161

Tyr Asp Thr Val Val Ile Thr Leu Lys Asn Met Ala Ser His Pro Val
1               5                   10                  15

Ser

<210> SEQ ID NO 162
<211> LENGTH: 15
<212> TYPE: PRT
<213> ORGANISM: Homo sapiens

<400> SEQUENCE: 162

Asp Thr Val Val Ile Thr Leu Lys Asn Met Ala Ser His Pro Val
1               5                   10                  15

<210> SEQ ID NO 163
<211> LENGTH: 14
<212> TYPE: PRT
<213> ORGANISM: Homo sapiens

<400> SEQUENCE: 163

Thr Val Val Ile Thr Leu Lys Asn Met Ala Ser His Pro Val
1               5                   10

<210> SEQ ID NO 164
<211> LENGTH: 15
<212> TYPE: PRT
<213> ORGANISM: Homo sapiens

<400> SEQUENCE: 164

Thr Val Val Ile Thr Leu Lys Asn Met Ala Ser His Pro Val Ser
1               5                   10                  15

<210> SEQ ID NO 165
<211> LENGTH: 14
<212> TYPE: PRT
<213> ORGANISM: Homo sapiens

<400> SEQUENCE: 165

Val Val Ile Thr Leu Lys Asn Met Ala Ser His Pro Val Ser
1               5                   10

<210> SEQ ID NO 166
<211> LENGTH: 18
<212> TYPE: PRT
<213> ORGANISM: Homo sapiens

```
<400> SEQUENCE: 166

Glu Lys Glu Asp Asp Lys Val Phe Pro Gly Gly Ser His Thr Tyr Val
1               5                   10                  15

Trp Gln

<210> SEQ ID NO 167
<211> LENGTH: 13
<212> TYPE: PRT
<213> ORGANISM: Homo sapiens

<400> SEQUENCE: 167

Ser Pro Ser Phe Ile Gln Ile Arg Ser Val Ala Lys Lys
1               5                   10

<210> SEQ ID NO 168
<211> LENGTH: 14
<212> TYPE: PRT
<213> ORGANISM: Homo sapiens

<400> SEQUENCE: 168

Ser Pro Ser Phe Ile Gln Ile Arg Ser Val Ala Lys Lys His
1               5                   10

<210> SEQ ID NO 169
<211> LENGTH: 16
<212> TYPE: PRT
<213> ORGANISM: Homo sapiens

<400> SEQUENCE: 169

Ser Pro Ser Phe Ile Gln Ile Arg Ser Val Ala Lys Lys His Pro Lys
1               5                   10                  15

<210> SEQ ID NO 170
<211> LENGTH: 17
<212> TYPE: PRT
<213> ORGANISM: Homo sapiens

<400> SEQUENCE: 170

Ser Pro Ser Phe Ile Gln Ile Arg Ser Val Ala Lys Lys His Pro Lys
1               5                   10                  15

Thr

<210> SEQ ID NO 171
<211> LENGTH: 20
<212> TYPE: PRT
<213> ORGANISM: Homo sapiens

<400> SEQUENCE: 171

Gly Glu Val Gly Asp Thr Leu Leu Ile Ile Phe Lys Asn Gln Ala Ser
1               5                   10                  15

Arg Pro Tyr Asn
            20

<210> SEQ ID NO 172
<211> LENGTH: 18
<212> TYPE: PRT
<213> ORGANISM: Homo sapiens

<400> SEQUENCE: 172

Glu Val Gly Asp Thr Leu Leu Ile Ile Phe Lys Asn Gln Ala Ser Arg
1               5                   10                  15

Pro Tyr
```

<210> SEQ ID NO 173
<211> LENGTH: 19
<212> TYPE: PRT
<213> ORGANISM: Homo sapiens

<400> SEQUENCE: 173

Glu Val Gly Asp Thr Leu Leu Ile Ile Phe Lys Asn Gln Ala Ser Arg
1               5                   10                  15

Pro Tyr Asn

<210> SEQ ID NO 174
<211> LENGTH: 20
<212> TYPE: PRT
<213> ORGANISM: Homo sapiens

<400> SEQUENCE: 174

Glu Val Gly Asp Thr Leu Leu Ile Ile Phe Lys Asn Gln Ala Ser Arg
1               5                   10                  15

Pro Tyr Asn Ile
            20

<210> SEQ ID NO 175
<211> LENGTH: 23
<212> TYPE: PRT
<213> ORGANISM: Homo sapiens

<400> SEQUENCE: 175

Glu Val Gly Asp Thr Leu Leu Ile Ile Phe Lys Asn Gln Ala Ser Arg
1               5                   10                  15

Pro Tyr Asn Ile Tyr Pro His
            20

<210> SEQ ID NO 176
<211> LENGTH: 24
<212> TYPE: PRT
<213> ORGANISM: Homo sapiens

<400> SEQUENCE: 176

Glu Val Gly Asp Thr Leu Leu Ile Ile Phe Lys Asn Gln Ala Ser Arg
1               5                   10                  15

Pro Tyr Asn Ile Tyr Pro His Gly
            20

<210> SEQ ID NO 177
<211> LENGTH: 17
<212> TYPE: PRT
<213> ORGANISM: Homo sapiens

<400> SEQUENCE: 177

Val Gly Asp Thr Leu Leu Ile Ile Phe Lys Asn Gln Ala Ser Arg Pro
1               5                   10                  15

Tyr

<210> SEQ ID NO 178
<211> LENGTH: 18
<212> TYPE: PRT
<213> ORGANISM: Homo sapiens

<400> SEQUENCE: 178

Val Gly Asp Thr Leu Leu Ile Ile Phe Lys Asn Gln Ala Ser Arg Pro
1               5                   10                  15

Tyr Asn

<210> SEQ ID NO 179
<211> LENGTH: 19
<212> TYPE: PRT
<213> ORGANISM: Homo sapiens

<400> SEQUENCE: 179

Val Gly Asp Thr Leu Leu Ile Ile Phe Lys Asn Gln Ala Ser Arg Pro
1               5                   10                  15

Tyr Asn Ile

<210> SEQ ID NO 180
<211> LENGTH: 16
<212> TYPE: PRT
<213> ORGANISM: Homo sapiens

<400> SEQUENCE: 180

Gly Asp Thr Leu Leu Ile Ile Phe Lys Asn Gln Ala Ser Arg Pro Tyr
1               5                   10                  15

<210> SEQ ID NO 181
<211> LENGTH: 17
<212> TYPE: PRT
<213> ORGANISM: Homo sapiens

<400> SEQUENCE: 181

Gly Asp Thr Leu Leu Ile Ile Phe Lys Asn Gln Ala Ser Arg Pro Tyr
1               5                   10                  15

Asn

<210> SEQ ID NO 182
<211> LENGTH: 15
<212> TYPE: PRT
<213> ORGANISM: Homo sapiens

<400> SEQUENCE: 182

Asp Thr Leu Leu Ile Ile Phe Lys Asn Gln Ala Ser Arg Pro Tyr
1               5                   10                  15

<210> SEQ ID NO 183
<211> LENGTH: 16
<212> TYPE: PRT
<213> ORGANISM: Homo sapiens

<400> SEQUENCE: 183

Asp Thr Leu Leu Ile Ile Phe Lys Asn Gln Ala Ser Arg Pro Tyr Asn
1               5                   10                  15

<210> SEQ ID NO 184
<211> LENGTH: 13
<212> TYPE: PRT
<213> ORGANISM: Homo sapiens

<400> SEQUENCE: 184

Leu Ile Ile Phe Lys Asn Gln Ala Ser Arg Pro Tyr Asn
1               5                   10

<210> SEQ ID NO 185
<211> LENGTH: 12
<212> TYPE: PRT
<213> ORGANISM: Homo sapiens

```
<400> SEQUENCE: 185

Ile Ile Phe Lys Asn Gln Ala Ser Arg Pro Tyr Asn
1               5                   10

<210> SEQ ID NO 186
<211> LENGTH: 16
<212> TYPE: PRT
<213> ORGANISM: Homo sapiens

<400> SEQUENCE: 186

Asp Ile Ser Ala Tyr Leu Leu Ser Lys Asn Asn Ala Ile Glu Pro Arg
1               5                   10                  15

<210> SEQ ID NO 187
<211> LENGTH: 15
<212> TYPE: PRT
<213> ORGANISM: Homo sapiens

<400> SEQUENCE: 187

Gln Glu Ala Lys Tyr Glu Thr Phe Ser Asp Asp Pro Ser Pro Gly
1               5                   10                  15

<210> SEQ ID NO 188
<211> LENGTH: 6
<212> TYPE: PRT
<213> ORGANISM: Homo sapiens

<400> SEQUENCE: 188

Met Ser Phe Phe Lys Met
1               5

<210> SEQ ID NO 189
<211> LENGTH: 27
<212> TYPE: PRT
<213> ORGANISM: Homo sapiens

<400> SEQUENCE: 189

Asn Ser Leu Asn Ser Gly Gln Gly Pro Ser Pro Lys Gln Leu Val Ser
1               5                   10                  15

Leu Gly Pro Glu Lys Ser Val Glu Gly Gln Asn
            20                  25

<210> SEQ ID NO 190
<211> LENGTH: 26
<212> TYPE: PRT
<213> ORGANISM: Homo sapiens

<400> SEQUENCE: 190

Ser Leu Asn Ser Gly Gln Gly Pro Ser Pro Lys Gln Leu Val Ser Leu
1               5                   10                  15

Gly Pro Glu Lys Ser Val Glu Gly Gln Asn
            20                  25

<210> SEQ ID NO 191
<211> LENGTH: 25
<212> TYPE: PRT
<213> ORGANISM: Homo sapiens

<400> SEQUENCE: 191

Leu Asn Ser Gly Gln Gly Pro Ser Pro Lys Gln Leu Val Ser Leu Gly
1               5                   10                  15

Pro Glu Lys Ser Val Glu Gly Gln Asn
            20                  25
```

<210> SEQ ID NO 192
<211> LENGTH: 24
<212> TYPE: PRT
<213> ORGANISM: Homo sapiens

<400> SEQUENCE: 192

Asn Ser Gly Gln Gly Pro Ser Pro Lys Gln Leu Val Ser Leu Gly Pro
1               5                   10                  15

Glu Lys Ser Val Glu Gly Gln Asn
            20

<210> SEQ ID NO 193
<211> LENGTH: 19
<212> TYPE: PRT
<213> ORGANISM: Homo sapiens

<400> SEQUENCE: 193

Gln Gly Pro Ser Pro Lys Gln Leu Val Ser Leu Gly Pro Glu Lys Ser
1               5                   10                  15

Val Glu Gly

<210> SEQ ID NO 194
<211> LENGTH: 21
<212> TYPE: PRT
<213> ORGANISM: Homo sapiens

<400> SEQUENCE: 194

Gln Gly Pro Ser Pro Lys Gln Leu Val Ser Leu Gly Pro Glu Lys Ser
1               5                   10                  15

Val Glu Gly Gln Asn
            20

<210> SEQ ID NO 195
<211> LENGTH: 22
<212> TYPE: PRT
<213> ORGANISM: Homo sapiens

<400> SEQUENCE: 195

Gln Gly Pro Ser Pro Lys Gln Leu Val Ser Leu Gly Pro Glu Lys Ser
1               5                   10                  15

Val Glu Gly Gln Asn Phe
            20

<210> SEQ ID NO 196
<211> LENGTH: 23
<212> TYPE: PRT
<213> ORGANISM: Homo sapiens

<400> SEQUENCE: 196

Gln Gly Pro Ser Pro Lys Gln Leu Val Ser Leu Gly Pro Glu Lys Ser
1               5                   10                  15

Val Glu Gly Gln Asn Phe Leu
            20

<210> SEQ ID NO 197
<211> LENGTH: 24
<212> TYPE: PRT
<213> ORGANISM: Homo sapiens

<400> SEQUENCE: 197

Gln Gly Pro Ser Pro Lys Gln Leu Val Ser Leu Gly Pro Glu Lys Ser
1               5                   10                  15

```
                1               5                  10                  15
Val Glu Gly Gln Asn Phe Leu Ser
            20

<210> SEQ ID NO 198
<211> LENGTH: 27
<212> TYPE: PRT
<213> ORGANISM: Homo sapiens

<400> SEQUENCE: 198

Gln Gly Pro Ser Pro Lys Gln Leu Val Ser Leu Gly Pro Glu Lys Ser
1               5                  10                  15

Val Glu Gly Gln Asn Phe Leu Ser Glu Lys Asn
            20                  25

<210> SEQ ID NO 199
<211> LENGTH: 15
<212> TYPE: PRT
<213> ORGANISM: Homo sapiens

<400> SEQUENCE: 199

Gly Pro Ser Pro Lys Gln Leu Val Ser Leu Gly Pro Glu Lys Ser
1               5                  10                  15

<210> SEQ ID NO 200
<211> LENGTH: 18
<212> TYPE: PRT
<213> ORGANISM: Homo sapiens

<400> SEQUENCE: 200

Gly Pro Ser Pro Lys Gln Leu Val Ser Leu Gly Pro Glu Lys Ser Val
1               5                  10                  15

Glu Gly

<210> SEQ ID NO 201
<211> LENGTH: 19
<212> TYPE: PRT
<213> ORGANISM: Homo sapiens

<400> SEQUENCE: 201

Gly Pro Ser Pro Lys Gln Leu Val Ser Leu Gly Pro Glu Lys Ser Val
1               5                  10                  15

Glu Gly Gln

<210> SEQ ID NO 202
<211> LENGTH: 20
<212> TYPE: PRT
<213> ORGANISM: Homo sapiens

<400> SEQUENCE: 202

Gly Pro Ser Pro Lys Gln Leu Val Ser Leu Gly Pro Glu Lys Ser Val
1               5                  10                  15

Glu Gly Gln Asn
            20

<210> SEQ ID NO 203
<211> LENGTH: 21
<212> TYPE: PRT
<213> ORGANISM: Homo sapiens

<400> SEQUENCE: 203

Gly Pro Ser Pro Lys Gln Leu Val Ser Leu Gly Pro Glu Lys Ser Val
```

```
1               5                  10                 15
Glu Gly Gln Asn Phe
            20

<210> SEQ ID NO 204
<211> LENGTH: 22
<212> TYPE: PRT
<213> ORGANISM: Homo sapiens

<400> SEQUENCE: 204

Gly Pro Ser Pro Lys Gln Leu Val Ser Leu Gly Pro Glu Lys Ser Val
1               5                   10                  15

Glu Gly Gln Asn Phe Leu
            20

<210> SEQ ID NO 205
<211> LENGTH: 24
<212> TYPE: PRT
<213> ORGANISM: Homo sapiens

<400> SEQUENCE: 205

Gly Pro Ser Pro Lys Gln Leu Val Ser Leu Gly Pro Glu Lys Ser Val
1               5                   10                  15

Glu Gly Gln Asn Phe Leu Ser Glu
            20

<210> SEQ ID NO 206
<211> LENGTH: 26
<212> TYPE: PRT
<213> ORGANISM: Homo sapiens

<400> SEQUENCE: 206

Gly Pro Ser Pro Lys Gln Leu Val Ser Leu Gly Pro Glu Lys Ser Val
1               5                   10                  15

Glu Gly Gln Asn Phe Leu Ser Glu Lys Asn
            20                  25

<210> SEQ ID NO 207
<211> LENGTH: 16
<212> TYPE: PRT
<213> ORGANISM: Homo sapiens

<400> SEQUENCE: 207

Arg Ser Pro Leu Pro Ile Ala Lys Val Ser Ser Phe Pro Ser Ile Arg
1               5                   10                  15

<210> SEQ ID NO 208
<211> LENGTH: 19
<212> TYPE: PRT
<213> ORGANISM: Homo sapiens

<400> SEQUENCE: 208

Arg Ser Pro Leu Pro Ile Ala Lys Val Ser Ser Phe Pro Ser Ile Arg
1               5                   10                  15

Pro Ile Tyr

<210> SEQ ID NO 209
<211> LENGTH: 20
<212> TYPE: PRT
<213> ORGANISM: Homo sapiens

<400> SEQUENCE: 209
```

```
Arg Ser Pro Leu Pro Ile Ala Lys Val Ser Ser Phe Pro Ser Ile Arg
1               5                   10                  15

Pro Ile Tyr Leu
            20

<210> SEQ ID NO 210
<211> LENGTH: 17
<212> TYPE: PRT
<213> ORGANISM: Homo sapiens

<400> SEQUENCE: 210

Ser Pro Leu Pro Ile Ala Lys Val Ser Ser Phe Pro Ser Ile Arg Pro
1               5                   10                  15

Ile

<210> SEQ ID NO 211
<211> LENGTH: 18
<212> TYPE: PRT
<213> ORGANISM: Homo sapiens

<400> SEQUENCE: 211

Ser Pro Leu Pro Ile Ala Lys Val Ser Ser Phe Pro Ser Ile Arg Pro
1               5                   10                  15

Ile Tyr

<210> SEQ ID NO 212
<211> LENGTH: 15
<212> TYPE: PRT
<213> ORGANISM: Homo sapiens

<400> SEQUENCE: 212

Leu Pro Ile Ala Lys Val Ser Ser Phe Pro Ser Ile Arg Pro Ile
1               5                   10                  15

<210> SEQ ID NO 213
<211> LENGTH: 27
<212> TYPE: PRT
<213> ORGANISM: Homo sapiens

<400> SEQUENCE: 213

Thr Tyr Lys Lys Val Glu Asn Thr Val Leu Pro Lys Pro Asp Leu Pro
1               5                   10                  15

Lys Thr Ser Gly Lys Val Glu Leu Leu Pro Lys
            20                  25

<210> SEQ ID NO 214
<211> LENGTH: 18
<212> TYPE: PRT
<213> ORGANISM: Homo sapiens

<400> SEQUENCE: 214

Gly Lys Val Pro Phe Leu Arg Val Ala Thr Glu Ser Ser Ala Lys Thr
1               5                   10                  15

Pro Ser

<210> SEQ ID NO 215
<211> LENGTH: 17
<212> TYPE: PRT
<213> ORGANISM: Homo sapiens

<400> SEQUENCE: 215

Lys Val Pro Phe Leu Arg Val Ala Thr Glu Ser Ser Ala Lys Thr Pro
```

<210> SEQ ID NO 216
<211> LENGTH: 17
<212> TYPE: PRT
<213> ORGANISM: Homo sapiens

<400> SEQUENCE: 216

Lys Lys Lys Asp Thr Ile Leu Ser Leu Asn Ala Cys Glu Ser Asn His
1               5                   10                  15
Ala

<210> SEQ ID NO 217
<211> LENGTH: 16
<212> TYPE: PRT
<213> ORGANISM: Homo sapiens

<400> SEQUENCE: 217

Lys Lys Asp Thr Ile Leu Ser Leu Asn Ala Cys Glu Ser Asn His Ala
1               5                   10                  15

<210> SEQ ID NO 218
<211> LENGTH: 16
<212> TYPE: PRT
<213> ORGANISM: Homo sapiens

<400> SEQUENCE: 218

Thr Ile Leu Ser Leu Asn Ala Cys Glu Ser Asn His Ala Ile Ala Ala
1               5                   10                  15

<210> SEQ ID NO 219
<211> LENGTH: 15
<212> TYPE: PRT
<213> ORGANISM: Homo sapiens

<400> SEQUENCE: 219

Ile Leu Ser Leu Asn Ala Cys Glu Ser Asn His Ala Ile Ala Ala
1               5                   10                  15

<210> SEQ ID NO 220
<211> LENGTH: 18
<212> TYPE: PRT
<213> ORGANISM: Homo sapiens

<400> SEQUENCE: 220

Glu Val Glu Asp Asn Ile Met Val Thr Phe Arg Asn Gln Ala Ser Arg
1               5                   10                  15
Pro Tyr

<210> SEQ ID NO 221
<211> LENGTH: 19
<212> TYPE: PRT
<213> ORGANISM: Homo sapiens

<400> SEQUENCE: 221

Glu Val Glu Asp Asn Ile Met Val Thr Phe Arg Asn Gln Ala Ser Arg
1               5                   10                  15
Pro Tyr Ser

<210> SEQ ID NO 222
<211> LENGTH: 16

<212> TYPE: PRT
<213> ORGANISM: Homo sapiens

<400> SEQUENCE: 222

Val Glu Asp Asn Ile Met Val Thr Phe Arg Asn Gln Ala Ser Arg Pro
1               5                   10                  15

<210> SEQ ID NO 223
<211> LENGTH: 17
<212> TYPE: PRT
<213> ORGANISM: Homo sapiens

<400> SEQUENCE: 223

Val Glu Asp Asn Ile Met Val Thr Phe Arg Asn Gln Ala Ser Arg Pro
1               5                   10                  15

Tyr

<210> SEQ ID NO 224
<211> LENGTH: 18
<212> TYPE: PRT
<213> ORGANISM: Homo sapiens

<400> SEQUENCE: 224

Val Glu Asp Asn Ile Met Val Thr Phe Arg Asn Gln Ala Ser Arg Pro
1               5                   10                  15

Tyr Ser

<210> SEQ ID NO 225
<211> LENGTH: 19
<212> TYPE: PRT
<213> ORGANISM: Homo sapiens

<400> SEQUENCE: 225

Val Glu Asp Asn Ile Met Val Thr Phe Arg Asn Gln Ala Ser Arg Pro
1               5                   10                  15

Tyr Ser Phe

<210> SEQ ID NO 226
<211> LENGTH: 15
<212> TYPE: PRT
<213> ORGANISM: Homo sapiens

<400> SEQUENCE: 226

Glu Asp Asn Ile Met Val Thr Phe Arg Asn Gln Ala Ser Arg Pro
1               5                   10                  15

<210> SEQ ID NO 227
<211> LENGTH: 16
<212> TYPE: PRT
<213> ORGANISM: Homo sapiens

<400> SEQUENCE: 227

Glu Asp Asn Ile Met Val Thr Phe Arg Asn Gln Ala Ser Arg Pro Tyr
1               5                   10                  15

<210> SEQ ID NO 228
<211> LENGTH: 17
<212> TYPE: PRT
<213> ORGANISM: Homo sapiens

<400> SEQUENCE: 228

Glu Asp Asn Ile Met Val Thr Phe Arg Asn Gln Ala Ser Arg Pro Tyr
1               5                   10                  15

Ser

<210> SEQ ID NO 229
<211> LENGTH: 14
<212> TYPE: PRT
<213> ORGANISM: Homo sapiens

<400> SEQUENCE: 229

Asp Asn Ile Met Val Thr Phe Arg Asn Gln Ala Ser Arg Pro
1               5                   10

<210> SEQ ID NO 230
<211> LENGTH: 15
<212> TYPE: PRT
<213> ORGANISM: Homo sapiens

<400> SEQUENCE: 230

Asp Asn Ile Met Val Thr Phe Arg Asn Gln Ala Ser Arg Pro Tyr
1               5                   10                  15

<210> SEQ ID NO 231
<211> LENGTH: 16
<212> TYPE: PRT
<213> ORGANISM: Homo sapiens

<400> SEQUENCE: 231

Asp Asn Ile Met Val Thr Phe Arg Asn Gln Ala Ser Arg Pro Tyr Ser
1               5                   10                  15

<210> SEQ ID NO 232
<211> LENGTH: 14
<212> TYPE: PRT
<213> ORGANISM: Homo sapiens

<400> SEQUENCE: 232

Asn Ile Met Val Thr Phe Arg Asn Gln Ala Ser Arg Pro Tyr
1               5                   10

<210> SEQ ID NO 233
<211> LENGTH: 9
<212> TYPE: PRT
<213> ORGANISM: Homo sapiens

<400> SEQUENCE: 233

Phe Arg Asn Gln Ala Ser Arg Pro Tyr
1               5

<210> SEQ ID NO 234
<211> LENGTH: 16
<212> TYPE: PRT
<213> ORGANISM: Homo sapiens

<400> SEQUENCE: 234

Leu Ala Pro Met Ile Ile His Gly Ile Lys Thr Gln Gly Ala Arg Gln
1               5                   10                  15

<210> SEQ ID NO 235
<211> LENGTH: 15
<212> TYPE: PRT
<213> ORGANISM: Homo sapiens

<400> SEQUENCE: 235

Ala Pro Met Ile Ile His Gly Ile Lys Thr Gln Gly Ala Arg Gln
1               5                   10                  15

```
<210> SEQ ID NO 236
<211> LENGTH: 16
<212> TYPE: PRT
<213> ORGANISM: Homo sapiens

<400> SEQUENCE: 236

Ala Pro Met Ile Ile His Gly Ile Lys Thr Gln Gly Ala Arg Gln Lys
1               5                   10                  15

<210> SEQ ID NO 237
<211> LENGTH: 16
<212> TYPE: PRT
<213> ORGANISM: Homo sapiens

<400> SEQUENCE: 237

Tyr Ile Ser Gln Phe Ile Ile Met Tyr Ser Leu Asp Gly Lys Lys Trp
1               5                   10                  15

<210> SEQ ID NO 238
<211> LENGTH: 15
<212> TYPE: PRT
<213> ORGANISM: Homo sapiens

<400> SEQUENCE: 238

Ile Ser Gln Phe Ile Ile Met Tyr Ser Leu Asp Gly Lys Lys Trp
1               5                   10                  15

<210> SEQ ID NO 239
<211> LENGTH: 16
<212> TYPE: PRT
<213> ORGANISM: Homo sapiens

<400> SEQUENCE: 239

Ile Ser Gln Phe Ile Ile Met Tyr Ser Leu Asp Gly Lys Lys Trp Gln
1               5                   10                  15

<210> SEQ ID NO 240
<211> LENGTH: 7
<212> TYPE: PRT
<213> ORGANISM: Homo sapiens

<400> SEQUENCE: 240

Tyr Ser Leu Asp Gly Lys Lys
1               5

<210> SEQ ID NO 241
<211> LENGTH: 8
<212> TYPE: PRT
<213> ORGANISM: Homo sapiens

<400> SEQUENCE: 241

Tyr Ser Leu Asp Gly Lys Lys Trp
1               5

<210> SEQ ID NO 242
<211> LENGTH: 16
<212> TYPE: PRT
<213> ORGANISM: Homo sapiens

<400> SEQUENCE: 242

Tyr Val Lys Glu Phe Leu Ile Ser Ser Ser Gln Asp Gly His Gln Trp
1               5                   10                  15
```

```
<210> SEQ ID NO 243
<211> LENGTH: 17
<212> TYPE: PRT
<213> ORGANISM: Homo sapiens

<400> SEQUENCE: 243

Tyr Val Lys Glu Phe Leu Ile Ser Ser Ser Gln Asp Gly His Gln Trp
1               5                   10                  15

Thr

<210> SEQ ID NO 244
<211> LENGTH: 14
<212> TYPE: PRT
<213> ORGANISM: Homo sapiens

<400> SEQUENCE: 244

Lys Glu Phe Leu Ile Ser Ser Ser Gln Asp Gly His Gln Trp
1               5                   10

<210> SEQ ID NO 245
<211> LENGTH: 16
<212> TYPE: PRT
<213> ORGANISM: Homo sapiens

<400> SEQUENCE: 245

Gly Asn Gln Asp Ser Phe Thr Pro Val Val Asn Ser Leu Asp Pro Pro
1               5                   10                  15

<210> SEQ ID NO 246
<211> LENGTH: 17
<212> TYPE: PRT
<213> ORGANISM: Homo sapiens

<400> SEQUENCE: 246

Gly Asn Gln Asp Ser Phe Thr Pro Val Val Asn Ser Leu Asp Pro Pro
1               5                   10                  15

Leu

<210> SEQ ID NO 247
<211> LENGTH: 15
<212> TYPE: PRT
<213> ORGANISM: Homo sapiens

<400> SEQUENCE: 247

Asn Gln Asp Ser Phe Thr Pro Val Val Asn Ser Leu Asp Pro Pro
1               5                   10                  15

<210> SEQ ID NO 248
<211> LENGTH: 16
<212> TYPE: PRT
<213> ORGANISM: Homo sapiens

<400> SEQUENCE: 248

Asn Gln Asp Ser Phe Thr Pro Val Val Asn Ser Leu Asp Pro Pro Leu
1               5                   10                  15

<210> SEQ ID NO 249
<211> LENGTH: 14
<212> TYPE: PRT
<213> ORGANISM: Homo sapiens

<400> SEQUENCE: 249

Gln Asp Ser Phe Thr Pro Val Val Asn Ser Leu Asp Pro Pro
1               5                   10
```

```
<210> SEQ ID NO 250
<211> LENGTH: 13
<212> TYPE: PRT
<213> ORGANISM: Homo sapiens

<400> SEQUENCE: 250

Asp Ser Phe Thr Pro Val Val Asn Ser Leu Asp Pro Pro
1               5                   10

<210> SEQ ID NO 251
<211> LENGTH: 29
<212> TYPE: PRT
<213> ORGANISM: Phleum pratense

<400> SEQUENCE: 251

Pro Lys Asp Asn Gly Gly Ala Cys Gly Tyr Lys Asp Val Asp Lys Pro
1               5                   10                  15

Pro Phe Ser Gly Met Thr Gly Cys Gly Asn Thr Pro Ile
            20                  25

<210> SEQ ID NO 252
<211> LENGTH: 15
<212> TYPE: PRT
<213> ORGANISM: Phleum pratense

<400> SEQUENCE: 252

Glu Glu Pro Ile Ala Pro Tyr His Phe Asp Leu Ser Gly His Ala
1               5                   10                  15

<210> SEQ ID NO 253
<211> LENGTH: 11
<212> TYPE: PRT
<213> ORGANISM: Phleum pratense

<400> SEQUENCE: 253

Gly Thr Lys Val Thr Phe His Val Glu Lys Gly
1               5                   10
```